US011896368B2

(12) United States Patent
Narasimha Rao et al.

(10) Patent No.: US 11,896,368 B2
(45) Date of Patent: Feb. 13, 2024

(54) SYSTEMS AND METHODS FOR DETERMINING SWIMMING METRICS

(71) Applicant: Apple Inc., Cupertino, CA (US)

(72) Inventors: Bharath Narasimha Rao, Mountain View, CA (US); Craig H. Mermel, San Jose, CA (US); Karthik Jayaraman Raghuram, Mountain View, CA (US); Hung A. Pham, Oakland, CA (US); Adam S. Howell, Oakland, CA (US); Rami Y. Hindiyeh, Pacifica, CA (US); James P. Ochs, San Francisco, CA (US); Vinay R. Majjigi, Mountain View, CA (US); Alexander Singh Alvarado, Sunnyvale, CA (US); Sunny K. Chow, Santa Clara, CA (US); Umamahesh Srinivas, Milpitas, CA (US); Xing Tan, San Jose, CA (US); Ronald K. Huang, San Jose, CA (US); Edith Merle Arnold, San Francisco, CA (US); Robin T. Guers, Cupertino, CA (US); Gunes Dervisoglu, Cupertino, CA (US); Adeeti Ullal, Mountain View, CA (US)

(73) Assignee: Apple Inc., Cupertino, CA (US)

( * ) Notice: Subject to any disclaimer, the term of this patent is extended or adjusted under 35 U.S.C. 154(b) by 729 days.

(21) Appl. No.: 15/691,245

(22) Filed: Aug. 30, 2017

(65) Prior Publication Data
US 2018/0056128 A1 Mar. 1, 2018

Related U.S. Application Data

(60) Provisional application No. 62/381,843, filed on Aug. 31, 2016, provisional application No. 62/381,846, (Continued)

(51) Int. Cl.
A61B 5/11 (2006.01)
A63B 24/00 (2006.01)
(Continued)

(52) U.S. Cl.
CPC .......... *A61B 5/1112* (2013.01); *A61B 5/0205* (2013.01); *A61B 5/02438* (2013.01);
(Continued)

(58) Field of Classification Search
CPC ........ A63B 24/0062; A63B 2024/0071; A61B 5/02438; A61B 5/1112; G01C 22/006; G01P 15/14; H04W 4/027
See application file for complete search history.

(56) References Cited

U.S. PATENT DOCUMENTS 4,566,461 A 1/1986 Lubell et al.
4,740,009 A 4/1988 Hoelzl
(Continued)

FOREIGN PATENT DOCUMENTS

AU 2008100295 A4 5/2008
CN 102481479 A 5/2012
(Continued)

OTHER PUBLICATIONS

Novatel, "IMU Error and Their Effects", Novatel Application Notes APN-064 Rev A p. 1-6, Feb. 21, 2014.
(Continued)

*Primary Examiner* — Manuel A Rivera Vargas
(74) *Attorney, Agent, or Firm* — Fish & Richardson P.C.

(57) ABSTRACT

The present disclosure relates to methods and systems of determining swimming metrics of a user during a swimming session. The method can include receiving, by a processor circuit of a user device, motion information from one or more motion sensors of the user device; determining, by the processor circuit using the motion information, a first set of
(Continued)

rotational data of the user device, wherein the first set of rotational data is expressed in a first frame of reference; converting, by the processor circuit, the first set of rotational data into a second set of rotational data, wherein the second set of rotational data is expressed in a second frame of reference; determining, by the processor circuit, one or more swimming metrics of the user; and outputting the one or more swimming metrics.

20 Claims, 40 Drawing Sheets

Related U.S. Application Data filed on Aug. 31, 2016, provisional application No. 62/381,988, filed on Aug. 31, 2016, provisional application No. 62/381,989, filed on Aug. 31, 2016, provisional application No. 62/381,641, filed on Aug. 31, 2016, provisional application No. 62/381,640, filed on Aug. 31, 2016.

(51) Int. Cl.
| | |
|---|---|
| *A61B 5/00* | (2006.01) |
| *A61B 5/024* | (2006.01) |
| *G01C 22/00* | (2006.01) |
| *H04W 4/02* | (2018.01) |
| *G01P 15/14* | (2013.01) |
| *A61B 5/0205* | (2006.01) |
| *G06V 40/20* | (2022.01) |
| *G06F 18/2135* | (2023.01) |
| *G06F 18/2411* | (2023.01) |

(52) U.S. Cl.
CPC ........... *A61B 5/1114* (2013.01); *A61B 5/1118* (2013.01); *A61B 5/1122* (2013.01); *A61B 5/681* (2013.01); *A63B 24/0062* (2013.01); *G01C 22/00* (2013.01); *G01C 22/006* (2013.01); *G01P 15/14* (2013.01); *G06F 18/2135* (2023.01); *G06F 18/2411* (2023.01); *G06V 40/23* (2022.01); *H04W 4/027* (2013.01); *A63B 2024/0071* (2013.01)

(56) References Cited

U.S. PATENT DOCUMENTS

| | | | |
|---|---|---|---|
| 5,158,093 | A | 10/1992 | Shvartz et al. |
| 5,663,897 | A | 9/1997 | Geiser |
| 5,664,499 | A | 9/1997 | Kingsmill |
| 6,013,008 | A | 1/2000 | Fukushima |
| 6,059,724 | A | 5/2000 | Campell et al. |
| 6,582,380 | B2 | 6/2003 | Kazlausky et al. |
| 6,687,535 | B2 | 2/2004 | Hautala et al. |
| 6,837,827 | B1 | 1/2005 | Lee et al. |
| 6,862,525 | B1 | 3/2005 | Beason et al. |
| 6,868,338 | B1 | 3/2005 | Elliott |
| 6,876,947 | B1 | 4/2005 | Darley et al. |
| 7,254,516 | B2 | 8/2007 | Case, Jr. et al. |
| 7,311,675 | B2 | 12/2007 | Peifer et al. |
| 7,377,180 | B2 | 5/2008 | Cunningham |
| 7,387,029 | B2 | 6/2008 | Cunningham |
| 7,467,060 | B2 | 12/2008 | Kulach et al. |
| 7,534,206 | B1 | 5/2009 | Lovitt et al. |
| 7,647,196 | B2 | 1/2010 | Kahn et al. |
| 7,690,556 | B1 | 4/2010 | Kahn et al. |
| 7,771,320 | B2 | 8/2010 | Riley et al. |
| 7,805,149 | B2 | 9/2010 | Werner et al. |
| 7,841,967 | B1 | 11/2010 | Kahn et al. |
| 8,290,480 | B2 | 10/2012 | Abramson et al. |
| 8,483,775 | B2 | 7/2013 | Buck et al. |
| 8,531,180 | B2 | 9/2013 | Piemonte et al. |
| 8,589,174 | B2 | 11/2013 | Nelson et al. |
| 8,638,320 | B2 | 1/2014 | Harley et al. |
| 8,653,956 | B2 | 2/2014 | Berkobin et al. |
| 8,784,271 | B2 | 7/2014 | Brumback et al. |
| 8,890,854 | B2 | 11/2014 | Tenuta et al. |
| 8,892,391 | B2 | 11/2014 | Tu et al. |
| 8,894,576 | B2 | 11/2014 | Alwan et al. |
| 8,911,329 | B2 | 12/2014 | Lin et al. |
| 8,928,635 | B2 | 1/2015 | Harley et al. |
| 9,195,305 | B2 | 11/2015 | Markovic et al. |
| 9,264,862 | B2 | 2/2016 | Tu et al. |
| 9,413,871 | B2 | 8/2016 | Nixon et al. |
| 9,448,250 | B2 | 9/2016 | Pham et al. |
| 9,526,430 | B2 | 12/2016 | Srinivas et al. |
| 9,704,412 | B2 | 7/2017 | Wells et al. |
| 9,737,761 | B1 | 8/2017 | Sivaraj |
| 9,788,794 | B2 | 10/2017 | Le Boeuf et al. |
| 9,817,948 | B2 | 11/2017 | Swank et al. |
| 9,918,646 | B2 | 3/2018 | Alvarado et al. |
| 9,998,864 | B2 | 6/2018 | Kumar et al. |
| 10,098,549 | B2 | 10/2018 | Tan et al. |
| 10,154,789 | B2 | 12/2018 | Raghuram et al. |
| 10,188,347 | B2 | 1/2019 | Self et al. |
| 10,206,627 | B2 | 2/2019 | Le Boeuf et al. |
| 10,219,708 | B2 | 3/2019 | Altini |
| 10,244,948 | B2 | 4/2019 | Pham et al. |
| 10,290,260 | B2 | 5/2019 | Wu et al. |
| 10,292,606 | B2 | 5/2019 | Wisbey et al. |
| 10,512,406 | B2 | 12/2019 | Martinez et al. |
| 10,524,670 | B2 | 1/2020 | Raghuram et al. |
| 10,620,232 | B2 | 4/2020 | Tu et al. |
| 10,687,707 | B2 | 6/2020 | Tan et al. |
| 10,687,752 | B2 | 6/2020 | Pham et al. |
| 10,694,994 | B2 | 6/2020 | Alvarado et al. |
| 10,699,594 | B2 | 6/2020 | Mermel et al. |
| 10,617,912 | B2 | 7/2020 | Narasimha Rao et al. |
| 10,709,933 | B2 | 7/2020 | Tan et al. |
| 11,051,720 | B2 | 7/2021 | Perry et al. |
| 11,103,749 | B2 | 8/2021 | Mermel et al. |
| 11,278,765 | B2 | 3/2022 | Mohrman et al. |
| 11,517,789 | B2 * | 12/2022 | Xie ................. A61B 5/725 |
| 2001/0022828 | A1 | 9/2001 | Pyles |
| 2002/0019585 | A1 | 2/2002 | Dickinson |
| 2003/0032460 | A1 | 2/2003 | Cannon et al. |
| 2003/0138763 | A1 | 7/2003 | Roncalez et al. |
| 2004/0064061 | A1 | 4/2004 | Nissila |
| 2005/0065443 | A1 | 3/2005 | Ternes |
| 2005/0107723 | A1 | 5/2005 | Wehman et al. |
| 2005/0124906 | A1 | 6/2005 | Childre et al. |
| 2005/0212701 | A1 | 9/2005 | Nimmo |
| 2006/0064277 | A1 | 3/2006 | Jung |
| 2006/0136173 | A1 | 6/2006 | Case et al. |
| 2006/0190217 | A1 | 8/2006 | Lee et al. |
| 2006/0217231 | A1 | 9/2006 | Parks et al. |
| 2007/0100666 | A1 | 5/2007 | Stivoric et al. |
| 2007/0150229 | A1 | 6/2007 | Fujiwara |
| 2007/0219059 | A1 | 9/2007 | Schwartz et al. |
| 2007/0275825 | A1 | 11/2007 | O'Brien |
| 2007/0276271 | A1 | 11/2007 | Chan |
| 2008/0096726 | A1 | 4/2008 | Riley et al. |
| 2008/0214360 | A1 | 9/2008 | Stirling et al. |
| 2009/0009320 | A1 | 1/2009 | O'Connor et al. |
| 2009/0024332 | A1 | 1/2009 | Karlov et al. |
| 2009/0043531 | A1 | 2/2009 | Kahn et al. |
| 2009/0063099 | A1 | 3/2009 | Counts et al. |
| 2009/0143199 | A1 | 6/2009 | Nishibayashi |
| 2009/0240461 | A1 | 9/2009 | Makino et al. |
| 2009/0319221 | A1 | 12/2009 | Kahn et al. |
| 2010/0030350 | A1 | 2/2010 | House et al. |
| 2010/0030482 | A1 * | 2/2010 | Li ................. A61B 5/1118 702/19 |
| 2010/0130890 | A1 | 5/2010 | Matsumura et al. |
| 2010/0184564 | A1 | 7/2010 | Molyneux et al. |
| 2010/0204952 | A1 | 8/2010 | Irlam et al. |
| 2010/0210953 | A1 | 8/2010 | Sholder et al. |
| 2010/0210975 | A1 | 8/2010 | Anthony, III et al. |
| 2010/0217099 | A1 | 8/2010 | Leboeuf et al. |
| 2010/0274102 | A1 | 10/2010 | Teixeira |
| 2010/0298656 | A1 | 11/2010 | McCombie et al. |

(56) References Cited

U.S. PATENT DOCUMENTS

| | | |
|---|---|---|
| 2011/0040193 A1 | 2/2011 | Seppanen et al. |
| 2011/0054359 A1 | 3/2011 | Sazonov et al. |
| 2011/0082008 A1 | 4/2011 | Cheung et al. |
| 2011/0131012 A1 | 6/2011 | Czaja et al. |
| 2011/0152695 A1 | 6/2011 | Granqvist et al. |
| 2011/0195707 A1 | 8/2011 | Faerber et al. |
| 2011/0238485 A1 | 9/2011 | Haumont et al. |
| 2011/0301436 A1 | 12/2011 | Teixeira |
| 2012/0006112 A1 | 1/2012 | Lee et al. |
| 2012/0083715 A1 | 4/2012 | Friedman |
| 2012/0172677 A1 | 7/2012 | Beith |
| 2012/0238832 A1 | 9/2012 | Hwang |
| 2012/0296455 A1 | 11/2012 | Ohnemus et al. |
| 2012/0322621 A1 | 12/2012 | Bingham et al. |
| 2013/0006522 A1 | 1/2013 | Vellaikal et al. |
| 2013/0023739 A1 | 1/2013 | Russel |
| 2013/0041590 A1 | 2/2013 | Burich et al. |
| 2013/0053990 A1 | 2/2013 | Ackland |
| 2013/0073255 A1* | 3/2013 | Yuen .................. A63B 24/0062 702/160 |
| 2013/0085861 A1 | 4/2013 | Dunlap |
| 2013/0096943 A1 | 4/2013 | Carey et al. |
| 2013/0135097 A1 | 5/2013 | Doezema |
| 2013/0158686 A1 | 6/2013 | Zhang et al. |
| 2013/0178335 A1 | 7/2013 | Lin et al. |
| 2013/0197377 A1 | 8/2013 | Takahiko et al. |
| 2013/0218053 A1 | 8/2013 | Kaiser et al. |
| 2013/0267794 A1 | 10/2013 | Fernstrom et al. |
| 2013/0326137 A1 | 12/2013 | Bilange et al. |
| 2013/0340287 A1 | 12/2013 | Stewart |
| 2014/0071082 A1 | 3/2014 | Singh et al. |
| 2014/0073486 A1 | 3/2014 | Ahmed et al. |
| 2014/0087708 A1 | 3/2014 | Kalita et al. |
| 2014/0088444 A1 | 3/2014 | Saalasti et al. |
| 2014/0107932 A1 | 4/2014 | Luna |
| 2014/0109390 A1 | 4/2014 | Manning |
| 2014/0121471 A1 | 5/2014 | Walker |
| 2014/0167973 A1 | 6/2014 | Letchner et al. |
| 2014/0172238 A1 | 6/2014 | Craine |
| 2014/0172361 A1 | 6/2014 | Chiang et al. |
| 2014/0197946 A1 | 7/2014 | Park et al. |
| 2014/0200906 A1 | 7/2014 | Bentley et al. |
| 2014/0207264 A1 | 7/2014 | Quy |
| 2014/0213920 A1 | 7/2014 | Lee et al. |
| 2014/0221854 A1 | 8/2014 | Wai |
| 2014/0228649 A1 | 8/2014 | Rayner et al. |
| 2014/0244071 A1 | 8/2014 | Czaja et al. |
| 2014/0266160 A1 | 9/2014 | Coza |
| 2014/0266789 A1 | 9/2014 | Matus |
| 2014/0276127 A1 | 9/2014 | Ferdosi et al. |
| 2014/0278139 A1 | 9/2014 | Hong et al. |
| 2014/0278229 A1 | 9/2014 | Hong et al. |
| 2014/0279123 A1 | 9/2014 | Harkey et al. |
| 2014/0316305 A1 | 10/2014 | Venkatraman et al. |
| 2014/0348367 A1 | 11/2014 | Vavrus et al. |
| 2015/0066526 A1 | 3/2015 | Cheng et al. |
| 2015/0072712 A1 | 3/2015 | Huang et al. |
| 2015/0087929 A1 | 3/2015 | Rapoport et al. |
| 2015/0088006 A1 | 3/2015 | Rapoport et al. |
| 2015/0100141 A1 | 4/2015 | Hughes |
| 2015/0105096 A1 | 4/2015 | Chowdhury et al. |
| 2015/0119728 A1 | 4/2015 | Blackadar et al. |
| 2015/0147734 A1 | 5/2015 | Flores et al. |
| 2015/0148632 A1 | 5/2015 | Benaron |
| 2015/0173631 A1* | 6/2015 | Richards .............. A61B 5/7282 600/479 |
| 2015/0182149 A1 | 7/2015 | Rapoport et al. |
| 2015/0250417 A1 | 9/2015 | Cheng et al. |
| 2015/0256689 A1 | 9/2015 | Erkkila et al. |
| 2015/0260514 A1 | 9/2015 | Menelas et al. |
| 2015/0294440 A1* | 10/2015 | Roberts .................... G06T 3/40 345/666 |
| 2015/0327804 A1 | 11/2015 | Lefever et al. |
| 2015/0328523 A1 | 11/2015 | Heling et al. |
| 2015/0338926 A1 | 11/2015 | Park et al. |
| 2015/0345985 A1 | 12/2015 | Fung et al. |
| 2015/0357048 A1 | 12/2015 | Goldstein |
| 2015/0374240 A1 | 12/2015 | Lee |
| 2016/0021238 A1 | 1/2016 | Abramson et al. |
| 2016/0038083 A1 | 2/2016 | Ding et al. |
| 2016/0054449 A1 | 2/2016 | Pekonen et al. |
| 2016/0057372 A1 | 3/2016 | Raghuram et al. |
| 2016/0058302 A1 | 3/2016 | Raghuram et al. |
| 2016/0058329 A1 | 3/2016 | Srinivas et al. |
| 2016/0058332 A1 | 3/2016 | Tan et al. |
| 2016/0058333 A1 | 3/2016 | Arnold et al. |
| 2016/0058356 A1 | 3/2016 | Raghuram et al. |
| 2016/0058370 A1 | 3/2016 | Raghuram et al. |
| 2016/0058371 A1 | 3/2016 | Singh Alvarado et al. |
| 2016/0058372 A1 | 3/2016 | Raghuram et al. |
| 2016/0059079 A1 | 3/2016 | Watterson |
| 2016/0066859 A1 | 3/2016 | Crawford et al. |
| 2016/0069679 A1 | 3/2016 | Jackson et al. |
| 2016/0084869 A1 | 3/2016 | Yuen et al. |
| 2016/0143579 A1* | 5/2016 | Martikka .............. A61B 5/0205 600/301 |
| 2016/0147319 A1 | 5/2016 | Agarwal et al. |
| 2016/0166178 A1 | 6/2016 | Fuss et al. |
| 2016/0170998 A1 | 6/2016 | Frank et al. |
| 2016/0206248 A1 | 7/2016 | Sartor et al. |
| 2016/0223578 A1 | 8/2016 | Klosinski, Jr. et al. |
| 2016/0242646 A1 | 8/2016 | Obma |
| 2016/0256058 A1 | 9/2016 | Pham et al. |
| 2016/0263435 A1* | 9/2016 | Venkatraman ....... A61B 5/1123 |
| 2016/0269572 A1 | 9/2016 | Erkkila et al. |
| 2016/0287177 A1 | 10/2016 | Huppert et al. |
| 2016/0301581 A1 | 10/2016 | Carter et al. |
| 2016/0314633 A1 | 10/2016 | Bonanni et al. |
| 2016/0361020 A1 | 12/2016 | LeBoeuf et al. |
| 2016/0363449 A1 | 12/2016 | Metzler et al. |
| 2016/0374614 A1 | 12/2016 | Cavallaro et al. |
| 2017/0007166 A1 | 1/2017 | Roover et al. |
| 2017/0061817 A1 | 3/2017 | Mettler May |
| 2017/0074897 A1 | 3/2017 | Mermel et al. |
| 2017/0082649 A1 | 3/2017 | Tu et al. |
| 2017/0094450 A1 | 3/2017 | Tu et al. |
| 2017/0111768 A1 | 4/2017 | Smith et al. |
| 2017/0181644 A1 | 6/2017 | Meer et al. |
| 2017/0188893 A1 | 7/2017 | Venkatraman et al. |
| 2017/0202486 A1 | 7/2017 | Martikka et al. |
| 2017/0211936 A1 | 7/2017 | Howell et al. |
| 2017/0242499 A1 | 8/2017 | Shah et al. |
| 2017/0242500 A1 | 8/2017 | Shah et al. |
| 2017/0251972 A1 | 9/2017 | Jayaraman et al. |
| 2017/0259116 A1 | 9/2017 | Mestas |
| 2017/0269734 A1 | 9/2017 | Graff |
| 2017/0269785 A1 | 9/2017 | Abdollahian et al. |
| 2017/0273619 A1 | 9/2017 | Alvarado et al. |
| 2017/0347885 A1 | 12/2017 | Tan et al. |
| 2017/0367658 A1 | 12/2017 | LeBoeuf et al. |
| 2017/0368413 A1 | 12/2017 | Shavit |
| 2018/0028863 A1 | 2/2018 | Matsuda |
| 2018/0043210 A1 | 2/2018 | Niehaus et al. |
| 2018/0049694 A1 | 2/2018 | Singh Alvarado et al. |
| 2018/0050235 A1 | 2/2018 | Tan et al. |
| 2018/0055375 A1 | 3/2018 | Martinez et al. |
| 2018/0055439 A1 | 3/2018 | Pham et al. |
| 2018/0056123 A1 | 3/2018 | Narasimha Rao et al. |
| 2018/0056128 A1 | 3/2018 | Narasimha Rao et al. |
| 2018/0056129 A1 | 3/2018 | Narasimha Rao et al. |
| 2018/0279914 A1 | 10/2018 | Patek et al. |
| 2018/0303381 A1 | 10/2018 | Todd et al. |
| 2018/0344217 A1 | 12/2018 | Perry et al. |
| 2019/0038938 A1 | 2/2019 | Nagasaka et al. |
| 2019/0076063 A1 | 3/2019 | Kent et al. |
| 2019/0090087 A1 | 3/2019 | Taylor et al. |
| 2019/0184230 A1 | 6/2019 | Lee et al. |
| 2019/0360813 A1 | 11/2019 | Zhao et al. |
| 2020/0232796 A1 | 7/2020 | Lee et al. |
| 2021/0068689 A1 | 3/2021 | Ochs et al. |
| 2021/0068712 A1 | 3/2021 | Humblet et al. |
| 2021/0068713 A1 | 3/2021 | Dervisoglu et al. |
| 2021/0093917 A1 | 4/2021 | Dervisoglu et al. |

(56) References Cited

U.S. PATENT DOCUMENTS

| | | | |
|---|---|---|---|
| 2021/0093918 | A1 | 4/2021 | Dervisoglu et al. |
| 2022/0241641 | A1 | 8/2022 | Mermel et al. |
| 2023/0232861 | A1* | 7/2023 | McClements ............ A23J 3/227 426/46 |

FOREIGN PATENT DOCUMENTS

| | | | |
|---|---|---|---|
| CN | 104218976 | A | 12/2014 |
| CN | 105031905 | A | 11/2015 |
| CN | 105068656 | A | 11/2015 |
| GB | 2465824 | | 6/2010 |
| IN | 259/KOL/2015 | | 12/2015 |
| JP | 2004089317 | | 3/2004 |
| JP | 2010-051333 | A | 3/2010 |
| JP | 2013-039316 | A | 2/2013 |
| JP | 2014-042757 | A | 3/2014 |
| JP | 2016-150018 | A | 8/2016 |
| JP | 2018-000543 | A | 1/2018 |
| JP | 2018-015187 | A | 2/2018 |
| JP | 2019028796 | | 2/2019 |
| JP | 2020148558 | | 9/2020 |
| RO | 122807 | B1 | 2/2010 |
| WO | 03/61779 | A1 | 7/2003 |
| WO | 2010090867 | | 8/2010 |
| WO | 2011/105914 | A1 | 9/2011 |
| WO | 2015/126182 | A1 | 8/2015 |
| WO | 2015/200900 | A1 | 12/2015 |
| WO | 2016/044831 | A1 | 3/2016 |
| WO | 2016/073620 | A1 | 5/2016 |
| WO | WO 2016142246 | | 9/2016 |
| WO | WO 2018117914 | | 6/2018 |

OTHER PUBLICATIONS

Le, et al., "Sensor-based Training Optimization of a Cyclist Group", Seventh International Conference on Hybrid Intelligent Systems, IEEE 2007, pp. 265-270.
International Search Report and Written Opinion received for PCT Patent Application No. PCT/US2018/047290, dated Nov. 8, 2018, 14 pages.
Kyle, Chester R., "Reduction of Wind Resistance and Power Output of Racing Cyclists and Runners Traveiiing in Groups", Ergonomics, vol. 22, No. 4, 1979, pp. 387-397.
LE et al., "Sensor Based Training Optimization of a Cyclist Group", Seventh International Conference on Hybrid Intelligent Systems, 2007, pp. 265-270.
KINprof, May 31, 2011, Predictive VO2max tests, Web Video, Retrieved from: https://www.youtube.com/watch?v=_9e3HcY1sm8.
PCT International Application No. PCT/US2017/049693, International Search Report dated Aug. 12, 2017, 3 pages.
Yamaji, et al., "Relationship Between Heart Rate and Relative Oxygen Intake in Male Subjects Aged 10 to 27 Years", J. Human Ergol., 7:29-39, Jan. 27, 1978.
Your Fitness FAQ, Why is it important to warm up and cool down in a workout?, 2012, Web, Retrieved from: http://www.yourfitnessfaq.com/whyisitimportanttowarmupandcooldowninaworkout.html.
Vella et al, Exercise After-Burn: Research Update, 2005, Web, Retrieved from: http://www.unm.edu/~lkravitz/Article%20folder/epocarticle.html.
Song et al., "Training Activity Recognition Systems Online Using Real-Time Crowdsourcing", University of Rochester Computer Science, UbiCom' 12, Sep. 5-8, 2012 (2 pages).
Rowlands et al., "Assessing Sedentary Behavior with the GENEActiv: Introducing the Sedentary Sphere". Medicine and science in sports and exercise 46.6 (2014): 1235-1247.
Hasson et al., "Accuracy of four resting metabolic rate production equations: Effects of sex, body mass index, age, and race/ethnicity", Journal of Science and Medicine in Sport, 2011, vol. 14, p. 344-351.
Lucas et al., "Mechanisms of orthostatic intolerance following very prolonged exercise", 2008, J Appl Physiol, 105: 213-225.

Kunze et al., "Where am i: Recognizing on-body positions of wearable sensors." Location-and context-awareness. Springer Berlin Heidelberg, 2005. 264-275.
Keytel et al., "Prediction of energy expenditure from heart rate monitoring during submaximal exercise", 2005, Journal of Sports Sciences, 23(3):289-97.
Sabatini, Kalman-filter-based orientation determination using inertial/magnetic sensors: observability analysis and performance evaluation, Sep. 27, 2011, Sensors 2011, 11, 9182-9206.
Jackson et al., "Prediction of functional aerobic capacity without exercise testing", Medicine and Science in Sports and Exercise, 22(6), 863-870, 1990.
Isaacs et al., "Modeling energy expenditure and oxygen consumption in human exposure models: accounting for fatigue and EPOC", 2008, Journal of Exposure Science and Environmental Epidemiology, 18: 289-298.
Human Kinetics, Aerobic Workout Components, 2011, Web, Retrieved from: http://www.humankinetics.com/excerpts/excerpts/aerobicworkoutcomponentsexcerpt.
Gao et al., "Evaluation of accelerometer based multi-sensor versus single-sensor activity recognition systems." Medical engineering & physics 36.6 (2014): 779-785.
Frankenfield et al., "Comparison of Predictive Equations for Resting Metabolic Rate in Healthy Nonobese and Obese adults: A systematic review". Journal of the American Dietetic Association. May 2005, vol. 105, No. 5, p. 775-789.
Chu, "In-Vehicle Driver Detection Using Mobile Phone Sensors", Submitted for Graduation with departmental Distinction In Electrical and Computer Engineering, Apirl 20, 2011, pp. 1-21.
Bo et al., "TEXIVE: Detecting Drivers Using Personal Smart Phones by Leveraging Inertial Sensors", Department of Computer Science, Illinois Institute of Technology, Chicago IL, Dec. 7, 2014, pp. 1-12.
Brooks, G.A. et al., "Exercise Physiology: Human Bioenergetics and Its Applications," Fourth Edition, McGraw Hill, ISBN 0-07-255642-0, Chapter 2: Bioenergetics, Chapter 10: Metabolic Response to Exercise: Lactate Metabolism During Exercise and Recovery, Excess Postexercise O2 Consumption (EPOC), O2 Deficit, O2 Debt, and the Anaerobic Threshold, Chapter 16: Cardiovascular Dynamics During Exercise, Chapter 21: Principles of Endurance Conditioning, Chapter 27: Exercise Testing and Prescription, 141 pages (2004).
Bruce, R.A. et al., "Exercising testing in adult normal subjects and cardiac patients," Pediatrics, vol. 32, No. Suppl., pp. 742-756 (Oct. 1963).
Bruce, R.A. et al., "Maximal oxygen intake and nomographic assessment of functional aerobic impairment in cardiovascular disease," American Heart Journal, vol. 85, Issue 4, pp. 546-562 (Apr. 1973).
Burke, Edmund R., "High-Tech Cycling," Second Edition, Human Kinetics, Chapter 4: Optimizing the Crank Cycle and Pedaling Cadence, Chapter 5: Cycling Biomechanics, Chapter 6: Cycling Power, Chapter 10: Physiology of Professional Road Cycling, Chapter 11: Physiology of Mountain Biking, 131 pages (2003).
Cavanagh, P.R. et al., "The effect of stride length variation on oxygen uptake during distance running," Medicine and Science in Sports and Exercise, vol. 14, No. 1, pp. 30-35 (1982).
Earnest, C.P. et al., "Cross-sectional association between maximal estimated cardiorespiratory fitness, cardiometabolic risk factors and metabolic syndrome for men and women in the Aerobics Center Longitudinal Study," Mayo Clin Proceedings, vol. 88, No. 3, pp. 259-270, 20 pages (Mar. 2013).
Fox, S.M. et al., "Physical Activity and the Prevention of Coronary Heart Disease," Bull. N.Y. Acad. Med., vol. 44, No. 8, pp. 950-967 (Aug. 1968).
Glass, S., et al., "ACSM's Metabolic Calculations Handbook," Lippincott Williams & Wilkins, 124 pages (2007).
Lavie, C.J. et al., "Impact of cardiorespiratory fitness on the obesity paradox in patients with heart failure," Mayo Clinic Proceedings, vol. 88, No. 3, pp. 251-258 (Mar. 2013).
Margaria, R. et al., "Energy cost of running," Journal of Applied Physiology, vol. 18, No. 2, pp. 367-370 (Mar. 1, 1963).

(56) References Cited

OTHER PUBLICATIONS

McArdle, W.D. et al., "Exercise Physiology: Nutrition, Energy and Human Performance," Seventh Edition, Lippincott Williams & Wilkins, Chapter 5: Introduction to Energy Transfer, Chapter 6: Energy Transfer in the Body, Chapter 7: Energy Transfer During Exercise, Chapter 8: Measurement of Human Energy Expenditure, Chapter 9: Human Energy Expenditure During Rest and Physical Activity, Chapter 10: Energy Expenditure During Walking, Jogging, Running and Swimming, Chapter 11: Individual Differences and Measurement of Energy Capacities, Chapter 21: Training for.
Myers, J. et al., "Exercise Capacity and Mortality Among Men Referred for Exercise Testing," The New England Journal of Medicine, vol. 346, No. 11, pp. 793-801 (Mar. 14, 2002).
Noakes, Timothy D., "Lore of Running," Fourth Edition, Human Kinetics, Chapter 2: Oxygen Transport and Running Economy, Chapter 3: Energy Systems and Running Performance, 157 pages (2002).
Rapoport, Benjamin I., "Metabolic Factors Limiting Performance in Marathon Runners," PLoS Computational Biology, vol. 6, Issue 10, 13 pages (Oct. 2010).
Tanaka, H. et al., "Age-predicted maximal heart rate revisited," Journal of the American College of Cardiology, vol. 37, Issue 1, pp. 153-156 (Jan. 2001).
Wang, L. et al., "Time constant of heart rate recovery after low level exercise as a useful measure of cardiovascular fitness," Conf. Proc. IEEE Eng. Med. Biol. Soc., vol. 1, pp. 1799-1802 (2006).
U.S. Appl. No. 17/015,912, filed Sep. 9, 2020, Humblet et al.
U.S. Appl. No. 17/015,965, filed Sep. 9, 2020, Dervisoglu et al.
U.S. Appl. No. 17/016,020, filed Sep. 9, 2020, Ochs et al.
Alexander, "Energetics and Optimization of Human Walking and Running," Am J Human Biology, Mar. 20, 2002, 14:641-648.
Lasecki, "Real-Time Crowd Labeling for Deployable Activity Recognition," University of Rochester Computer Science, Feb. 23, 2013, 10 pages.
Latt et al., "Walking speed, cadence and step length are selected to optimize the stability of head and pelvis accelerations," Experimental Brain Research, Aug. 24, 2007, 184: 201-209.
Morgan et al., "Effect of step length optimization on the aerobic demand of miming," Journal of Applied Physiology, 1994, 245-251.
PCT International Preliminary Report on Patentability in International Appln. No. PCT/US2017/049693, dated Mar. 5, 2019, 8 pages.
PCT International Preliminary Report on Patentability in International Appln. No. PCT/US2018/047290, dated Mar. 17, 2020, 9 pages.
Pfitzinger.com "Optimal Marathon Training Sessions, Distance Coach.com, Intelligent Training for Distance Runners," archived May 15, 2012, <https://web.archive.org/web/20120515081237/http://www.pfitzinger.com/marathontraining.shtml>, printed Jan. 20, 2017, 3 pages.
Romijn et al., "Regulation of endogenous fat and carbohydrate metabolism in relation to exercise intensity and duration," Am. J. Physiol., 1993, 6:1-13.
Triendurance.com "Running with a Higher Cadence, Triendurance," Oct. 23, 2021, retrieved from <https://web.archive.org/web/20080228162904/http://www.trienduranee.com/Related.asp?PageID=14&NavID=7>, 2 pages.
Zhao, "New Developments of the Typical MEMS and Wearable Sensor Technologies," Micronanoelectronic Technology, Jan. 2015, 52(1):1-13 (with English abstract).
Zhou et al., "Development of the Technical Monitoring System for Swimming Competition," China Sport Science and Technology, Aug. 2008, 44(4):84-86 (with English abstract).
Mattfeld et al., "A New Dataset for Evaluating Pedometer Performance," IEEE International Conference on Bioinformatics and Biomedicine (BIBM), Nov. 2017, pp. 865-869.
Shen et al., "MiLift: Efficient Smartwatch-Based Workout Tracking Using Automatic Segmentation," Jul. 2018, 17(7):1609-1622.
Unuma et al., JP2007093433, published on Apr. 12, 2007, 27 pages (machine translated English version).

* cited by examiner

SYSTEMS AND METHODS FOR DETERMINING SWIMMING METRICS

PRIORITY CLAIM

This application claims priority to and the benefit of U.S. Provisional Patent Application No. 62/381,640, titled "Systems and Methods for Detecting Turns," which is filed on Aug. 31, 2016 and is incorporated by reference herein in its entirety.

This application claims priority to and the benefit of U.S. Provisional Patent Application No. 62/381,641, titled "Systems and Methods for Detecting Breaths While Swimming," which is filed on Aug. 31, 2016 and is incorporated by reference herein in its entirety.

This application claims priority to and the benefit of U.S. Provisional Patent Application No. 62/381,988, titled "Systems and Methods for Counting Laps," which is filed on Aug. 31, 2016 and is incorporated by reference herein in its entirety.

This application claims priority to and the benefit of U.S. Provisional Patent Application No. 62/381,989, titled "Systems and Methods for Determining Swimming Pool Length," which is filed on Aug. 31, 2016 and is incorporated by reference herein in its entirety.

This application claims priority to and the benefit of U.S. Provisional Patent Application No. 62/381,846, titled "Systems and Methods of Counting Swim Strokes," which is filed on Aug. 31, 2016 and is incorporated by reference herein in its entirety.

This application claims priority to and the benefit of U.S. Provisional Patent Application No. 62/381,843, titled "Systems and Methods for Detecting Swim Activity Using Inertial Sensors", which is filed on Aug. 31, 2016 and is incorporated by reference herein in its entirety.

CROSS-REFERENCE TO RELATED APPLICATIONS

This application relates to U.S. patent application Ser. No. 15/692,726, titled "Systems and Methods of Swimming Analysis," which is filed on Aug. 31, 2017 and is incorporated by reference herein in its entirety.

This application relates to U.S. patent application Ser. No. 15/692,237, titled "Systems and Methods of Swimming Calorimetry," which is filed on Aug. 31, 2017 and is incorporated by reference herein in its entirety.

FIELD

The present disclosure relates generally to detecting swim activity using inertial sensors.

BACKGROUND

When a user is doing exercise or making movements, it is oftentimes useful to detect when the user makes a change in direction. Keeping track of the user's turns or changes in direction can be useful in many applications. As an example, when the user is swimming, detecting a turn made by the user may imply the user completes a lap. As another example, when the user is walking and/or running, knowing the user makes a turn or changes in direction can be useful in tracking the user's location. It is sometimes, however, not easy or practical for the user to keep track of the changes in direction made by him or her. For example, when the user is swimming, he or she may not want to mentally keep track of the number of turns made by him or her. Accordingly, it is desirable to provide methods and systems of detecting turns while swimming.

When a user is swimming, there is often a need to detect when and how frequently the user is taking a breath. For example, this information can be used to detect exertion, level of effort, general fitness, and/or swimming ability. It is generally, however, not practical for the user to keep track of the breaths taken by him or her. Accordingly, it is desirable to provide methods and systems of detecting user's breaths while swimming.

When a user is doing activities that includes multiple types of motions, there is often a need to classify the types of motions. As an example, when a user is swimming laps, the user can switch between two types of motions: swimming and turning. As another example, when a user is running, the user can switch between running and walking. Knowing which type of motions a user is doing is useful in many applications including estimating energy expenditure of the user. Accordingly, it is desirable to provide methods and systems of determining a user's types of motions, including how many strokes the user has taken while swimming.

When a user is swimming, there is often a need to determine the number of laps a user swims during a swimming session. Keeping track of the number of laps the user swims can be useful in many applications, such as to calculate the total distance a user swims and/or the energy expenditure associated with a swimming session. Accordingly, it is desirable to provide methods and systems of determining the number of laps a user swims during a swimming session.

When a user is performing a swimming session, the user may transition from periods of swimming to periods of rest. While it is reasonable to expect that a user tracking his/her swim metrics (e.g., lap count, lap speed, strokes per lap, time splits, distance, calories, etc.) via a wearable device will indicate the start and end of the workout through interaction with the device, it is not always practical to do so. In a typical swim workout, periods of continuous swimming are interspersed with varying durations of rest. Accordingly, it is desirable to detect periods of lap swimming for the purpose of accurate swim metric evaluation.

When a user is swimming in a pool, there is often a need to know the length of the swimming pool. Information of the length of a swimming pool can be used to calculate the total distance a user swims and the energy expenditure associated with a swimming session. The pool length information, however, is not always readily available to users. Additionally, users may not be able to accurately estimate the pool length. Accordingly, it is desirable to provide methods and systems of determining a length of a swimming pool.

SUMMARY

The present disclosure relates to a method for improving an accuracy of a wearable device while determining swimming metrics of a user during a swimming session. In some embodiments, the method can include: receiving, by a processor circuit of the wearable device, motion data from one or more motion sensors of the wearable device; determining, by the processor circuit using the motion data, a first set of rotational data of the wearable device, wherein the first set of rotational data is expressed in a first frame of reference; converting, by the processor circuit, the first set of rotational data into a second set of rotational data, wherein the second set of rotational data is expressed in a second frame of reference; determining, by the processor circuit, one or more swimming metrics of the user based on the second set of rotational data, wherein the one or more swimming metrics comprise at least one of turns, breaths, laps, swimming styles, and swimming strokes; and outputting, by the processor circuit, the one or more swimming metrics of the user.

In some embodiments, the first frame of reference can include a body-fixed frame of reference with respect to the wearable device. In some embodiments, the second frame of reference can include an inertial frame of reference.

In some embodiments, the method can include: determining, by the processor circuit, yaw rotational data from the second set of rotational data; determining, by the processor circuit, one or more turns of the user based on the yaw rotational data. In some embodiments, the method can include: determining unfiltered yaw rotational data, wherein the unfiltered yaw rotational data are part of the second set of rotational data; and filtering the unfiltered yaw rotational data. In some embodiments, the method can include: determining a time constant proportional to a period which the user needs to complete a stroke; and filtering the unfiltered yaw rotational data based on the time constant.

In some embodiments, the method can include: determining a pitch angle from the second set of rotational data; comparing the pitch angle with a threshold angle; and determining one or more breaths of the user based upon comparing the pitch angle with the threshold angle. In some embodiments, the threshold angle can be associated with a swimming style of the user, wherein the swimming style is at least one of freestyle, butterfly, or breast stroke. In some embodiments, the threshold can be associated with a swimming skill level of the user.

In some embodiments, the method can include: converting the second set of rotational data to a set of two-dimensional rotational data; adding one or more constraints to the set of two-dimensional rotational data; and counting, by the processor circuit, one or more swimming strokes from the constrained two-dimensional rotational data. In some embodiments, the method can include: determining a primary axis of rotation based on the second set of rotational data; projecting the second set of three-dimensional rotational data to a two-dimensional space based on the primary axis of rotation; and determining the set of two-dimensional rotational data based on the projection. In some embodiments, the one or more constraints comprises at least one of accelerometer energy, moment arm calculations, or rotational direction. In some embodiments, the method can include counting revolutions of circles in the constrained two-dimensional rotational data. In some embodiments, the method can include counting revolutions of semi-circles in the constrained two-dimensional rotational data.

In some embodiments, the method can include: detecting a number of turns and a number of strokes of the user during the swimming session based on the received motion data; determining a stroke range per lap based on the number of turns and the number of strokes; determining whether a turn is not detected; inserting a missing turn in response to a determination that a turn is not detected; determining a variance of strokes per lap; adjusting the detected number of turns to reduce the variance of strokes per lap; and determining a lap count of the user based on the adjusted number of turns.

In some embodiment, the method can include: determining whether the number of strokes of the user converges in the swimming session; or determining whether the number of strokes made by the user converges in a historical swimming session. In some embodiments, the method can include: determining a standard deviation of the number of strokes among consecutive turns; and comparing the standard deviation with a threshold. In some embodiments, threshold can be 1.5 strokes.

In some embodiments, the method can include: comparing the number of strokes between two consecutive turns with the determined stroke range per lap. In some embodiments, the method can include: comparing the number of strokes between two consecutive turns with a threshold, wherein the threshold is determined by multiplying a mean value of the number of strokes per lap with a ratio.

In some embodiments, the method can include: determining a stroke rate of the user; classifying a stroke style for the user based on the motion data; determining a confidence value based on the stroke rate and the stroke style; determining a motion signature of the user, wherein the motion signature is swimming; and determining the user is swimming based on the confidence value and the motion signature. In some embodiments, the stroke style comprises at least one of freestyle, backstroke, breaststroke, or butterfly.

In some embodiments, the method can include: receiving an input from the user whether to calibrate a length of the swimming pool; if the input indicates that the user selects to calibrate the length of the swimming pool: prompting the user to perform an activity along an edge of the swimming pool, wherein the edge is parallel with a direction the user swims, receiving distance data associated with the activity, calculating the length of the swimming pool based on the distance data, and determining the one or more swimming metrics based on the calculated length of the swimming pool; and if the input indicates that the user does not select to calibrate the length of the swimming pool: counting a number of swimming strokes per lap, and calculating the length of the swimming pool based on the number of strokes per lap and a default stroke length, and determining the one or more swimming metrics based on the calculated length of the swimming pool.

In some embodiments, the method can include: receiving, by the processor circuit, a number of steps associated with the activity from a pedometer of the wearable device, wherein the activity comprises at least one of walking or running. In some embodiments, the method can include: receiving, by the processor circuit, location data from a GPS sensor of the wearable device.

The present disclosure also relates to a system for improving an accuracy of a wearable device while determining one or more swimming metrics of a user during a swimming session. In some embodiments, the system can include: one or more motion sensors configured to collect motion data; and a processor circuit coupled to the one or more motion sensors and configured to execute instructions causing the processor to: determine a first set of rotational data, wherein the first set of rotational data is expressed in a first frame of reference; convert the first set of rotational data into a second set of rotational data, wherein the second set of rotational data is expressed in a second frame of reference; determine one or more swimming metrics of the user based on the second set of rotational data; and output the one or more swimming metrics of the user.

Other features and advantages will become apparent from the following detailed description and drawings.

BRIEF DESCRIPTION OF THE DRAWINGS

Various objects, features, and advantages of the present disclosure can be more fully appreciated with reference to the following detailed description of the present disclosure when considered in connection with the following drawings, in which like reference numerals identify like elements.

DETAILED DESCRIPTION

The present disclosure relates to a method and system for detecting swim activity based on motion sensor signals obtained from a wearable device. Generally, user arm movement when swimming has distinct periodic signatures, unlike periods of rest which are typified by random user behavior.

The wearable device can include one or more motion sensors to collect data about the wearable device's position and orientation in space and to track changes to the wearable device's position and orientation over time.

Figure 1:
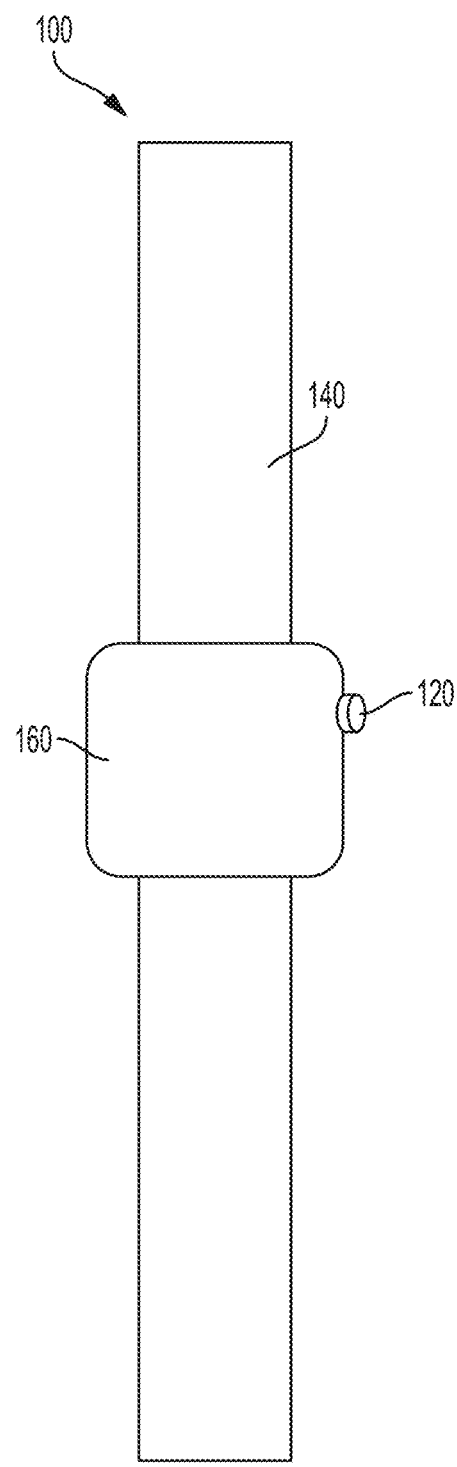
FIG. 1 illustrates a wearable device (or a "user device") according to some embodiments of the present disclosure.

FIG. 1 shows an example of a wearable device (or a "user device") 100 according to some embodiments of the present disclosure. In some embodiments, wearable device 100 may be any suitable wearable device, such as a watch and/or a fitness band configured to be worn around an individual's wrist.

Figure 2:
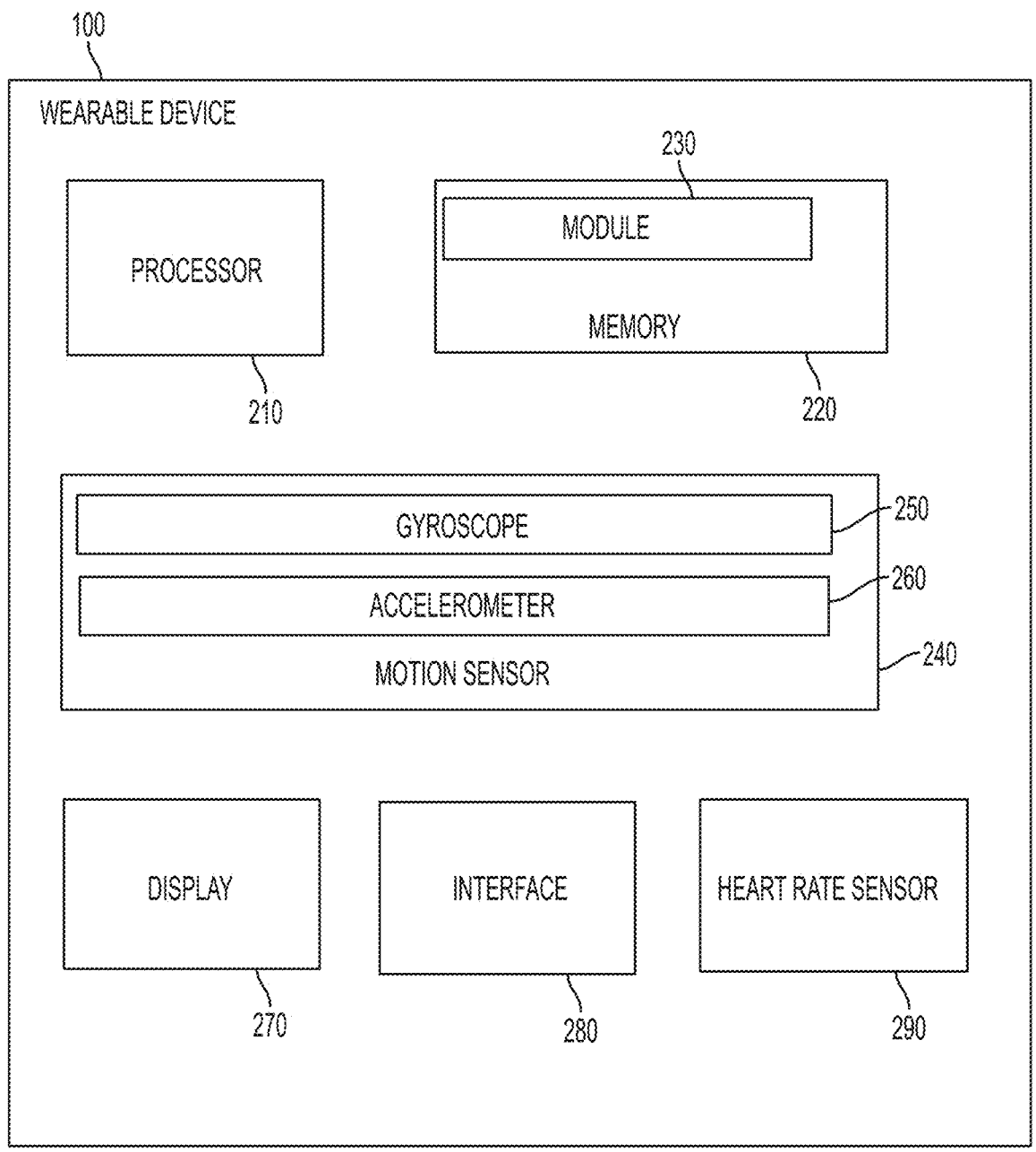
FIG. 2 illustrates a block diagram of a wearable device according to some embodiments of the present disclosure.

FIG. 2 depicts a block diagram of exemplary components that may be found within wearable device 100 according to some embodiments of the present disclosure. In some embodiments, wearable device 100 can include a processor 210, a memory 220, one or more motion sensors 240, a display 270, an interface 280, and a heart rate sensor 290. Wearable device 100 may include additional modules, fewer modules, or any other suitable combination of modules that perform any suitable operation or combination of operations.

In some embodiments, processor 210 can include one or more cores and can accommodate one or more threads to run various applications and modules. Software can run on processor 210 capable of executing computer instructions or computer code. Processor 210 can also be implemented in hardware using an application specific integrated circuit (ASIC), programmable logic array (PLA), field programmable gate array (FPGA), or any other integrated circuit.

Memory 220 can be a non-transitory computer readable medium, flash memory, a magnetic disk drive, an optical drive, a programmable read-only memory (PROM), a read-only memory (ROM), or any other memory or combination of memories. Memory 220 can include one or more modules 230.

Processor 210 can be configured to run module 230 stored in memory 220 that is configured to cause processor 210 to perform various steps that are discussed throughout the present disclosure, such as, for example, the methods described in connection with FIG. 5. In some embodiments, wearable device 100 can include one or more motion sensors 240. For example, motion sensors 240 can include a gyroscope 250 and an accelerometer 260. In some embodiments, accelerometer 260 may be a three-axes accelerometer that measures linear acceleration in up to three-dimensions (for example, x-axis, y-axis, and z-axis). In some embodiments, gyroscope 250 may be a three-axes gyroscope that measures rotational data, such as rotational movement and/or angular velocity, in up to three-dimension (for example, yaw, pitch, and roll). In some embodiments, accelerometer 260 may be a microelectromechanical system (MEMS) accelerometer, and gyroscope 250 may be an MEMS gyroscope. Processor 210 of wearable device 100 may receive motion information from one or more motion sensors 240 to track acceleration, rotation, position, orientation or gravity information of wearable device 100 in six degrees of freedom through three-dimensional space.

The motion information received from one or more motion sensors 240 may be expressed in a body-fixed frame of reference with respect to wearable device 100. In some embodiments, the motion information can be converted from the body fixed frame of reference to the inertial frame of reference. Conversion of sensor data to the inertial frame of reference is a necessary process prior to stroke detection, as well as stroke counting, turn detection, stroke phase classification and in some aspects of stroke classification, as described in the respective applications referenced above, and incorporated by reference herein in their entirety.

In some embodiments, wearable device 100 may include other types of sensors in addition to accelerometer 260 and gyroscope 250. For example, wearable device 100 may include an altimeter or barometer, or other types of location sensors, such as a GPS sensor. Wearable device 100 may also include display 270. Display 270 may be a screen, such as a crystalline (e.g., sapphire) or glass touchscreen, configured to provide output to the user as well as receive input from the user via touch. For example, display 270 may be configured to display a current heart rate or daily average energy expenditure. Display 270 may receive input from the user to select, for example, which information should be displayed, or whether the user is beginning a physical activity (e.g., starting a session) or ending a physical activity (e.g., ending a session), such as a swimming session, a running session, a weight lifting session, a walking session or a cycling session. In some embodiments, wearable device 100 may present output to the user in other ways, such as by producing sound with a speaker (not shown), and wearable device 100 may receive input from the user in other ways, such as by receiving voice commands via a microphone (not shown).

In some embodiments, wearable device 100 may communicate with external devices via interface 280, including a configuration to present output to a user or receive input from a user. Interface 280 may be a wireless interface. The wireless interface may be a standard Bluetooth (IEEE 802.15) interface, such as Bluetooth v4.0, also known as "Bluetooth low energy." In other embodiments, the interface may operate according to a cellphone network protocol such as Long Term Evolution (LTE) or a Wi-Fi (IEEE 802.11) protocol. In other embodiments, interface 280 may include wired interfaces, such as a headphone jack or bus connector (e.g., Lightning, Thunderbolt, USB, etc.).

Wearable device 100 can measure an individual's current heart rate from heart rate sensor 290. Heart rate sensor 290 may also be configured to determine a confidence level indicating a relative likelihood of an accuracy of a given heart rate measurement. In other embodiments, a traditional heart rate monitor may be used and may communicate with wearable device 100 through a near field communication method (e.g., Bluetooth).

Wearable device 100 may be configured to communicate with a companion device 300 (FIG. 3), such as a smartphone, as described in more detail herein. In some embodiments, wearable device 100 may be configured to communicate with other external devices, such as a notebook or desktop computer, tablet, headphones, Bluetooth headset, etc.

The modules described above are examples, and embodiments of wearable device 100 may include other modules not shown. For example, some embodiments of wearable device 100 may include a rechargeable battery (e.g., a lithium-ion battery), a microphone or a microphone array, one or more cameras, one or more speakers, a watchband, water-resistant casing or coating, etc. In some embodiments, all modules within wearable device 100 can be electrically and/or mechanically coupled together. In some embodiments, processor 210 can coordinate the communication among each module.

Figure 3:
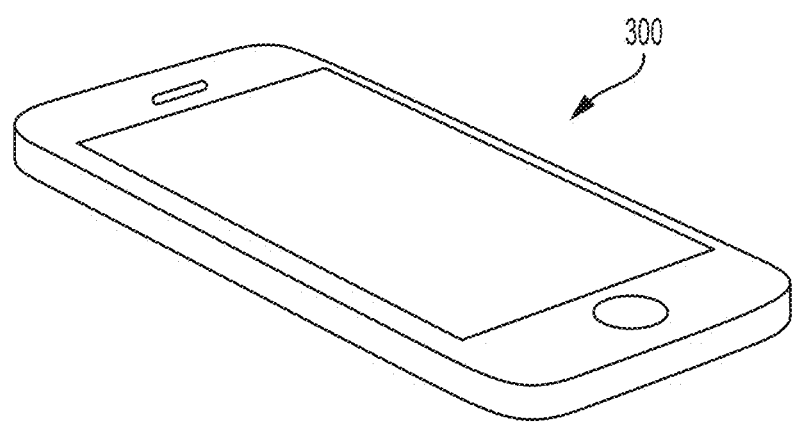
FIG. 3 illustrates a companion device according to some embodiments of the present disclosure.

FIG. 3 shows an example of a companion device 300 according to some embodiments of the present disclosure. Wearable device 100 may be configured to communicate with companion device 300 via a wired or wireless communication channel (e.g., Bluetooth, Wi-Fi, etc.). In some embodiments, companion device 300 may be a smartphone, tablet computer, or similar portable computing device. Companion device 300 may be carried by the user, stored in the user's pocket, strapped to the user's arm with an armband or similar device, placed in a mounting device, or otherwise positioned within communicable range of wearable device 100. In some embodiments, companion device 300 may include a variety of sensors, such as location and motion sensors (not shown). When companion device 300 is available for communication with wearable device 100, wearable device 100 may receive additional data from companion device 300 to improve or supplement its calibration or calorimetry processes. For example, in some embodiments, wearable device 100 may not include a GPS sensor as opposed to an alternative embodiment in which wearable device 100 may include a GPS sensor. In the case where wearable device 100 may not include a GPS sensor, a GPS sensor of companion device 300 may collect GPS location information, and wearable device 100 may receive the GPS location information via interface 280 (FIG. 2) from companion device 300.

In another example, wearable device 100 may not include an altimeter or barometer, as opposed to an alternative embodiment in which wearable device 100 may include an altimeter or barometer. In the case where wearable device 100 may not include an altimeter or barometer, an altimeter or barometer of companion device 300 may collect altitude or relative altitude information, and wearable device 100 may receive the altitude or relative altitude information via interface 280 (FIG. 2) from the companion device 300.

In another example, wearable device 100 may receive motion information from companion device 300. Wearable device 100 may compare the motion information from companion device 300 with motion information from one or more motion sensors 240 of wearable device 100. Motion information such as data from accelerometer 260 and/or gyroscope 250 may be filtered (e.g. by a high-pass, low-pass, band-pass, or band-stop filter) in order to improve the quality of motion information. For example, a low-pass filter may be used to remove some ambient noise.

Wearable device 100 may use sensed and collected motion information to predict a user's activity. Examples of activities may include, but are not limited to, swimming, walking, running, cycling, weight lifting etc. Wearable device 100 may also be able to predict or otherwise detect when a user is sedentary (e.g., sleeping, sitting, standing still, driving or otherwise controlling a vehicle, etc.) Wearable device 100 may use a variety of motion information, including, in some embodiments, motion information from a companion device. In some embodiments, information from one or more of accelerometers, gyroscopes, global positioning (GPS) devices, and heart rate sensors can be used to determine whether a user is engaging in swimming.

Figure 4A:
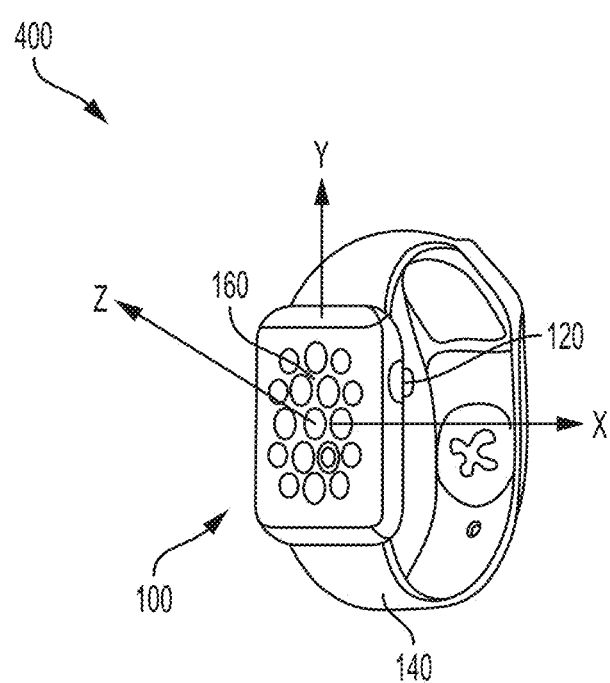
FIGS. 4A-4D illustrate examples of a body-fixed frame of reference according to some embodiments of the present disclosure.

FIG. 4A illustrates an example of a body-fixed frame of reference 500 according to some embodiments of the present disclosure. In FIG. 5A, the rotational axes of body-fixed frame of reference 400 are with respect to wearable device 100. For example, the z-axis is perpendicular to the display surface 160 of wearable device 100. The x-axis and the y-axis can be chosen relatively arbitrarily as long as the three axes are perpendicular to each other. In FIG. 4A, the x-axis is parallel with the direction pointed by crown 120 of wearable device 100, and the y-axis is parallel with the direction of band 140 of wearable device 100 (assuming the direction pointed by crown 120 of wearable device 100 is perpendicular to the direction of band 140 of wearable device 100).

Figure 4B:
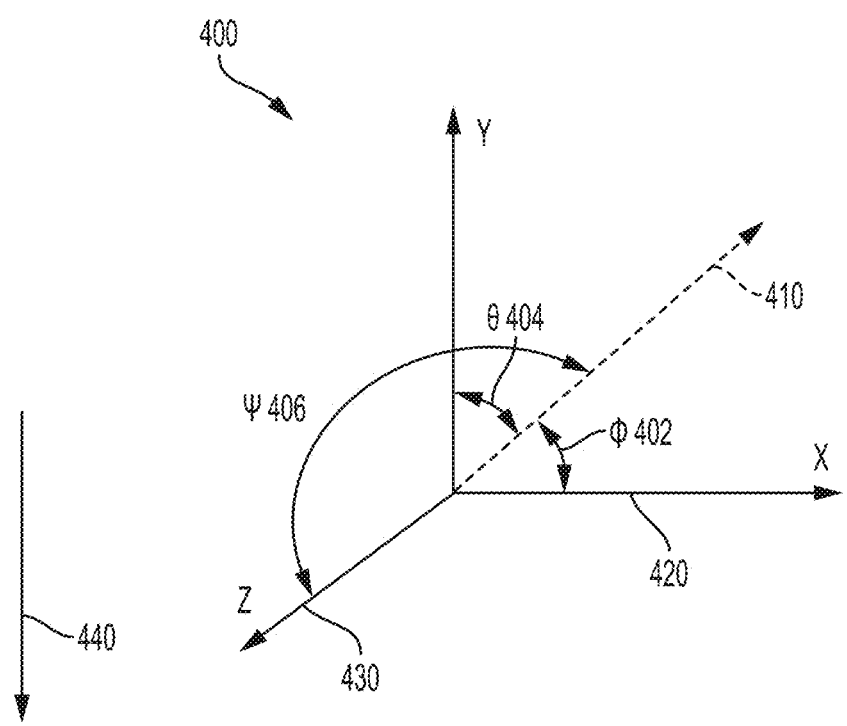
Figure 4C:
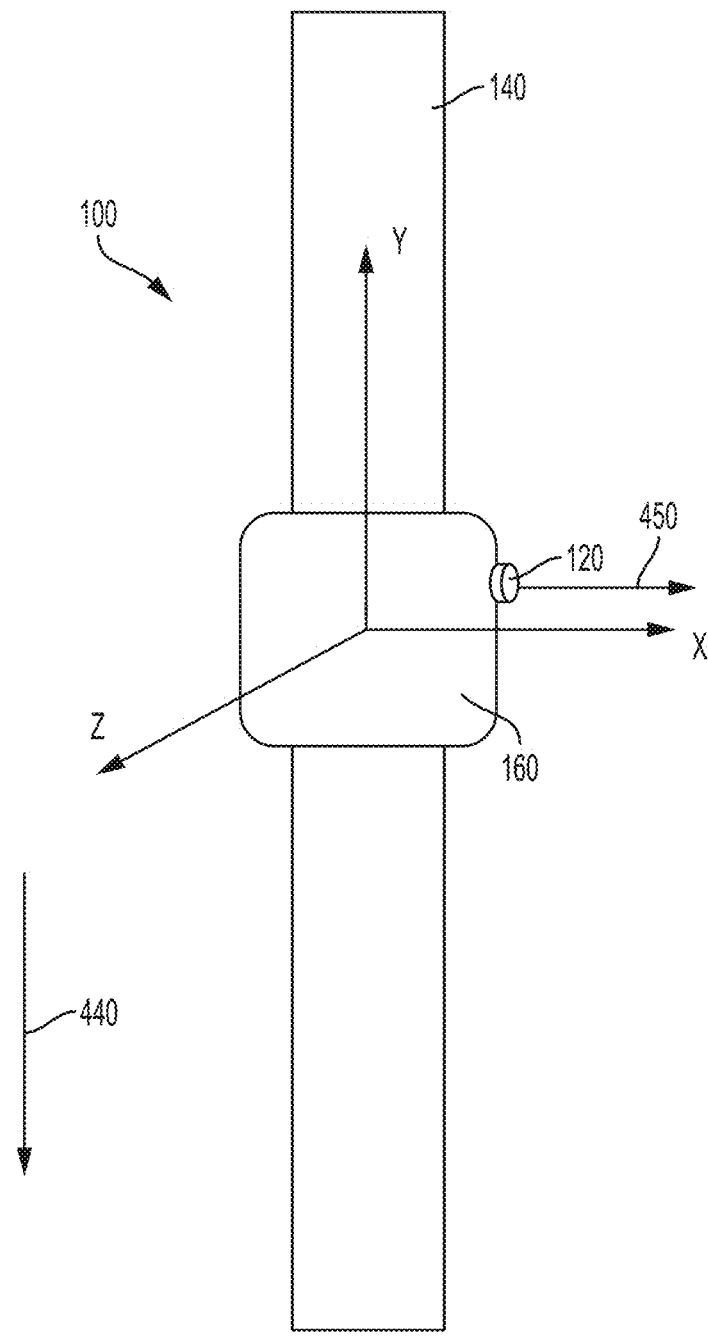
Figure 4D:
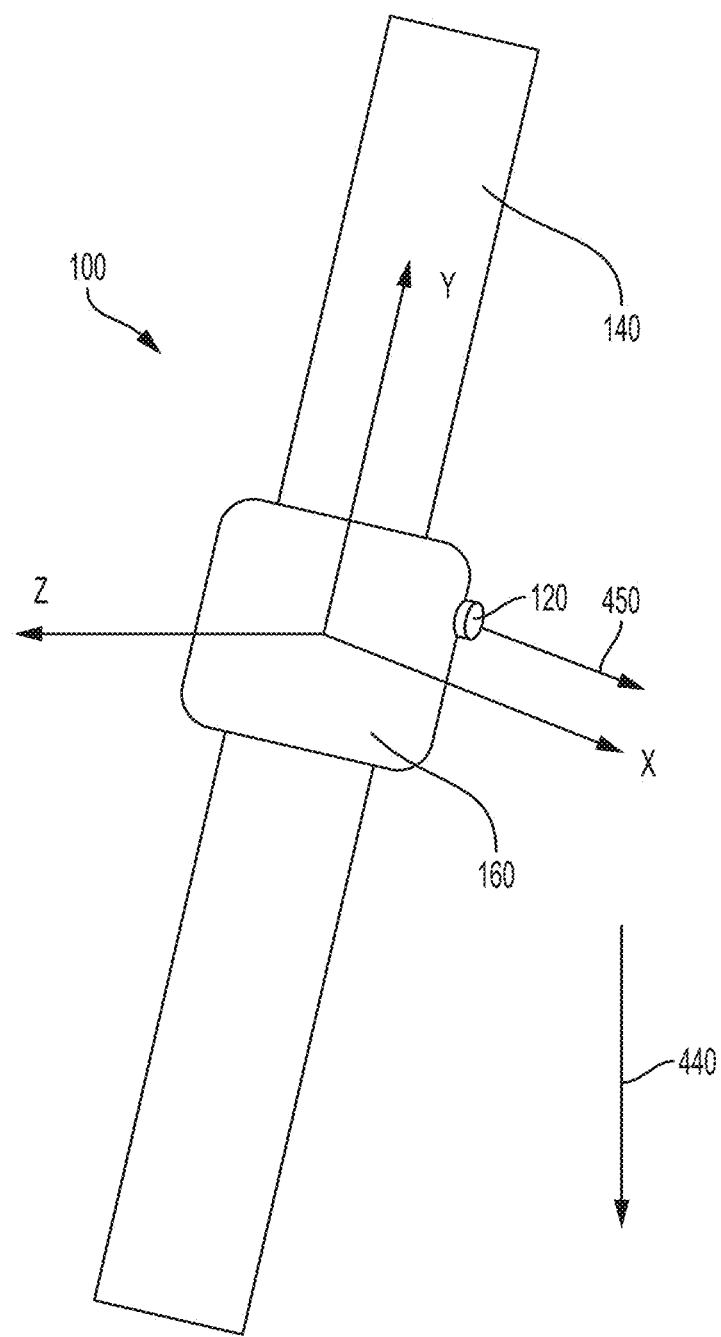

FIG. 4B-4D illustrates examples to express one or more orientations in body-fixed frame of reference 500 according to some embodiments of the present disclosure. In FIG. 4B, an orientation/direction 410 has an angle ($\varphi$) 402 with respect to the positive x-axis, an angle ($\theta$) 404 with respect to the positive y-axis, and an angle ($\psi$) 406 with respect to the positive z-axis. The direction 410 can be expressed in body-fixed frame of reference 400 as [cos($\varphi$), cos($\theta$), cos($\psi$)], which is a non-limiting example/format of the first set of rotational data. For example, direction 420 in FIG. 4B is parallel with and pointing toward the positive x-axis, so the angle ($\varphi$) between direction 420 and the positive x-axis is 0-degree; the angle ($\theta$) between direction 420 and the positive y-axis is 90-degree; and the angle ($\psi$) between direction 420 and the positive z-axis is 90-degree. Therefore, direction 420 can be expressed as [cos(0), cos(90), cos(90)], which is [1, 0, 0]. As another example, direction 430 in FIG. 4B is parallel with and pointing toward the positive z-axis, so the angle ($\varphi$) between direction 430 and the positive x-axis is 90-degree; the angle ($\theta$) between direction 430 and the positive y-axis is 90-degree; and the angle ($\psi$) between direction 430 and the positive z-axis is 0-degree. Therefore, direction 430 can be expressed as [cos(90), cos(90), cos(0)], which is [0, 0, 1]. As yet another example, direction 440 represents direction of gravity in FIG. 4B and is parallel with and pointing toward the negative y-axis, so the angle ($\varphi$) between direction 440 and the positive x-axis is 90-degree; the angle ($\theta$) between direction 440 and the positive y-axis is 180-degree; and the angle ($\psi$) between direction 440 and the positive z-axis is 90-degree. Therefore, direction 440 can be expressed as [cos(90), cos(180), cos(90)], which is [0, −1, 0].

In FIG. 4C, wearable device 100 is held vertically. As discussed earlier, the x-axis is parallel with direction pointed by crown 120, the y-axis is parallel with band 140, and the z-axis is perpendicular to display surface 160. Direction 450 in FIG. 4C represents the direction pointed by crown 120, so the angle ($\varphi$) between direction 450 and the positive x-axis is 0-degree; the angle ($\theta$) between direction 450 and the positive y-axis is 90-degree; and the angle ($\psi$) between direction 450 and the positive z-axis is 90-degree. Therefore, direction 450 can be expressed as [cos(0), cos(90), cos(90)], which is [1, 0, 0]. As another example, direction 440 represents direction of gravity in FIG. 4C and is parallel with and pointing toward the negative y-axis, so the angle ($\varphi$) between direction 440 and the positive x-axis is 90-degree; the angle ($\theta$) between direction 440 and the positive y-axis is 180-degree; and the angle ($\psi$) between direction 440 and the positive z-axis is 90-degree. Therefore, direction 440 in FIG. 4C can be expressed as [cos(90), cos(180), cos(90)], which is [0, −1, 0].

In FIG. 4D, wearable device 100 is rotated 45-degree clockwise compared with FIG. 4C. As discussed earlier, the x-axis is parallel with direction pointed by crown 120, the y-axis is parallel with band 140, and the z-axis is perpendicular to display surface 160. Direction 450 in FIG. 4D represents the direction pointed by crown 120, so the angle ($\varphi$) between direction 450 and the positive x-axis is 0-degree; the angle ($\theta$) between direction 450 and the positive y-axis is 90-degree; and the angle ($\psi$) between direction 450 and the positive z-axis is 90-degree. Therefore, direction 450 can be expressed as [cos(0), cos(90), cos(90)], which is [1, 0, 0]. As another example, direction 440 represents direction of gravity in FIG. 4D. The angle ($\varphi$) between direction 440 and the positive x-axis is 45-degree; the angle ($\theta$) between direction 440 and the positive y-axis is 135-degree; and the angle ($\psi$) between direction 440 and the positive z-axis is 90-degree. Therefore, direction 440 in FIG. 4D can be expressed as [cos(45), cos(135), cos(0)], which is [0.707, −0.707, 0].

It is noted that the expression of direction 450 is the same in FIG. 4C and FIG. 4D even though wearable device 100 has rotated. This is because the body-fixed frame of reference 400 is always fixed with respect to wearable device 100. As a result, when position of wearable device 100 changes, the three axes in body-fixed frame of reference 400 and direction 450 change too, and relative position between direction 450 and the three axes remain the same. On the other hand, although direction of gravity 440 does not change in an "absolute" sense, it does not rotate together with wearable device 100. Therefore, the expression of gravity direction 440 can be changed in the body-fixed frame of reference 500 when wearable device changes position.

Figure 5:
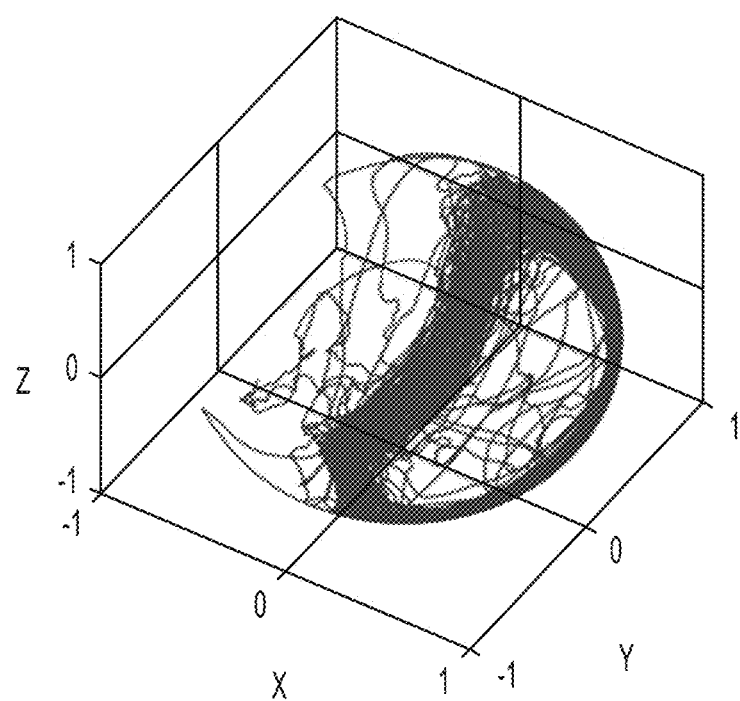
FIG. 5 illustrates a set of rotational data of a wearable device in a body-fixed frame of reference according to some embodiments of the present disclosure.

FIG. 5 illustrates a first set of rotational data of wearable device 100 according to some embodiments of the present disclosure. Specifically, FIG. 5 illustrates estimation of the gravity in the body-fixed frame of reference 400. The x-axis shows cos($\varphi$) where $\varphi$ is the angle between gravity and the positive x-axis in the body-fixed frame of reference 400. The y-axis shows cos($\theta$), where $\theta$ is the angle between gravity and the positive y-axis in the body-fixed frame of reference 400. The z-axis shows cos($\psi$), where $\psi$ is the angle between gravity and the positive z-axis in the body-fixed frame of reference 400. For example, if at a moment wearable device 100 is facing up toward the sky, and display surface is parallel with the ground, then the gravity direction can be expressed as [0, 0, −1]. As another example, if crown is pointed towards the ground, then the gravity direction can be expressed as [1, 0, 0]. Gravity estimation in body-fixed frame of reference can help indicate when wearable device 100 is making a pitch and/or roll movement. For example, as discussed above, when a user's wrist was in a position such that crown is pointed towards the ground, the gravity direction is [1, 0, 0]. If the user then is rolling his or her wrist up for 90-degree, then display surface of wearable device 100 is facing up toward the sky, and display surface is parallel with the ground, then the gravity direction is expressed as [0, 0, −1]. If the user then is pitching his or her wrist up for 90-degree, then crown of wearable device 100 is facing up toward the sky, and the gravity direction is expressed as [−1, 0, 0]. These examples illustrate that gravity direction in the body-fixed frame of reference 400 can change in response to pitch and/or roll movement. In some embodiments, the gravity estimation in body-fixed frame of reference 400 can be used together with accelerometer 260 to estimate gravity. However, the gravity direction in the body-fixed frame of reference 400 does not change in response to yaw movement. For example, if wearable device 100 is facing up toward the sky, and display surface is parallel with the ground, then the gravity direction is expressed as [0, 0, −1]; then if the user making yaw movement along the horizon plane, the gravity direction remains as [0, 0, −1]. Also, as discussed above, because wearable device 100 is rotating the same as the body-fixed frame of reference 400, the directions of wearable device 100 and components thereof are fixed. For example, no matter whether crown is pointing up, straight, or down, the crown direction is always expressed in body-fixed frame of reference 400 as [1, 0, 0]. Therefore, in some embodiments, it is more suitable to express the positions of wearable device 100 in a frame of reference that is not body-fixed in order to more readily indicate the movements of wearable device 100 with respect to external references.

Figure 6:
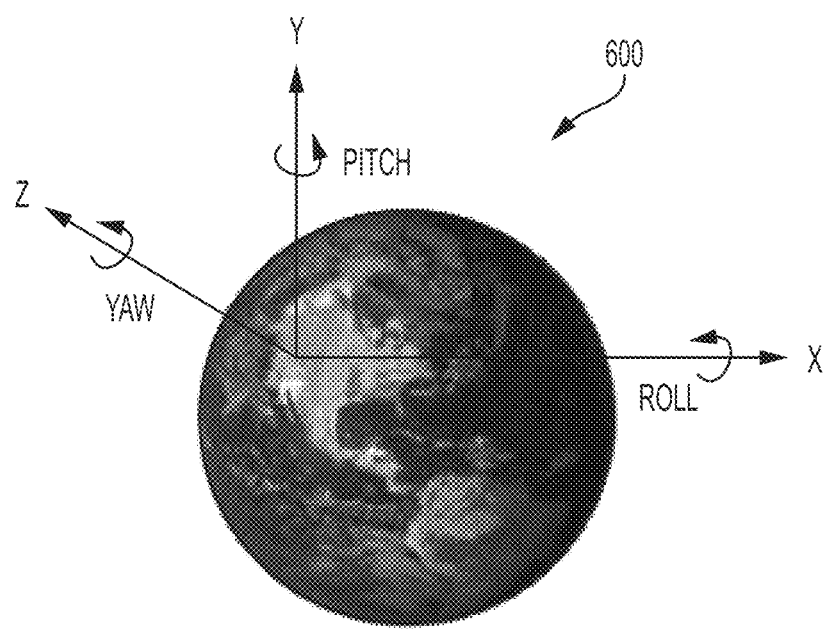
FIG. 6 illustrates an example of an inertial frame of reference according to some embodiments of the present disclosure.

FIG. 6 illustrates an inertial frame of reference 600 according to some embodiments of the present disclosure. In FIG. 6, the z-axis (or the yaw axis) is based on the direction of gravity. The x-axis (or the roll axis) and the y-axis (or the pitch axis) can be chosen relatively arbitrarily as long as the three axes are perpendicular to each other.

Figure 7A:
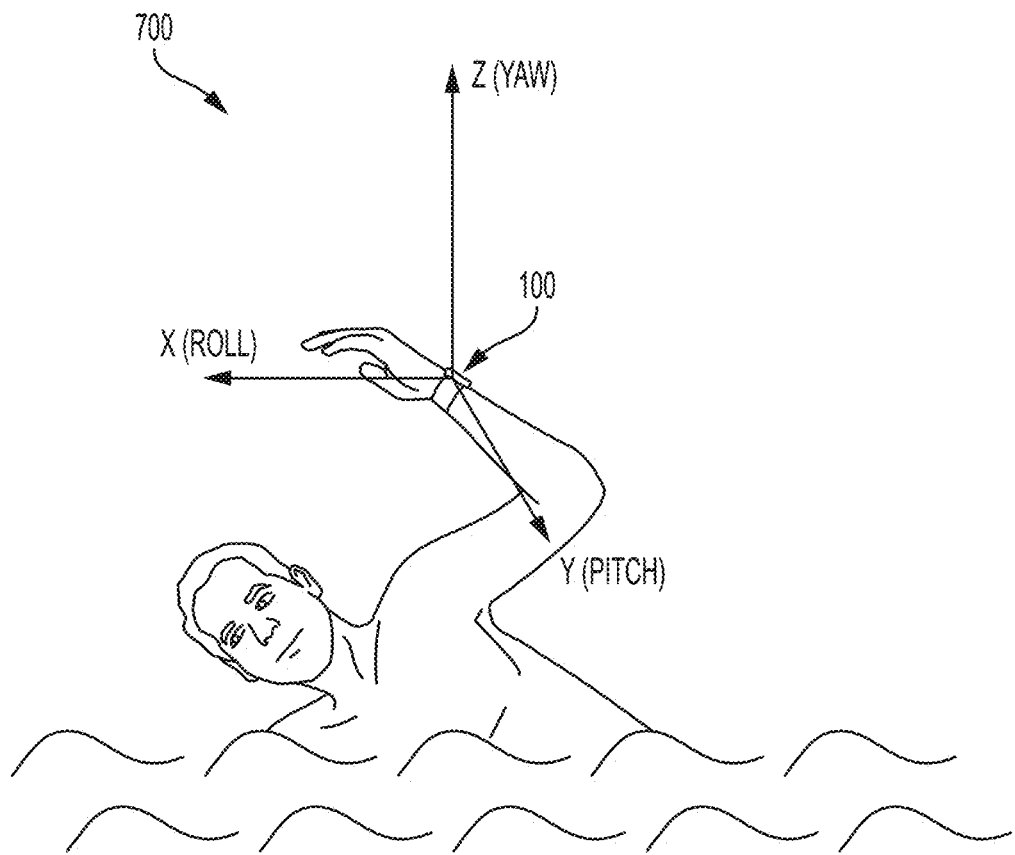
FIGS. 7A-7D illustrate examples of an inertial frame of reference according to some embodiments of the present disclosure.

FIGS. 7A-7D illustrate an example of an inertial frame of reference 700 according to some embodiments of the present disclosure. FIG. 7A depicts inertial frame of reference 700 in a context where a user is swimming. In FIG. 7A, the user wears wearable device 100. But the z-axis (or the yaw axis) in the inertial frame of reference is based on the direction of gravity rather than the wearable device itself. Additionally, assuming the user is swimming laps, the x-axis (or the roll axis) is substantially parallel to the direction of the laps, and the y-axis (or the pitch axis) is perpendicular to the other two axes. In some embodiments, the x-axis (or the roll axis) and the y-axis (or the pitch axis) can be chosen relatively arbitrarily as long as the three axes are perpendicular to each other. In FIG. 7A, the z-axis is also referred to as yaw axis because any yaw movement rotates around the z-axis. Similarly, the x-axis is also referred to as roll axis because any roll movement rotates around the x-axis. And the y-axis is also referred to as pitch axis because any pitch movement rotates around the y-axis. By knowing the difference between the three-axis in the fixed-body frame of reference 400 and the three-axis in the inertial frame of reference 700, the rotational data expressed in the fixed-body frame of reference 400 can be converted into the rotational data expressed in the inertial frame of reference 700 using techniques appreciated by people skilled in the art such as the one discussed in Sabatini.

Figure 7B:
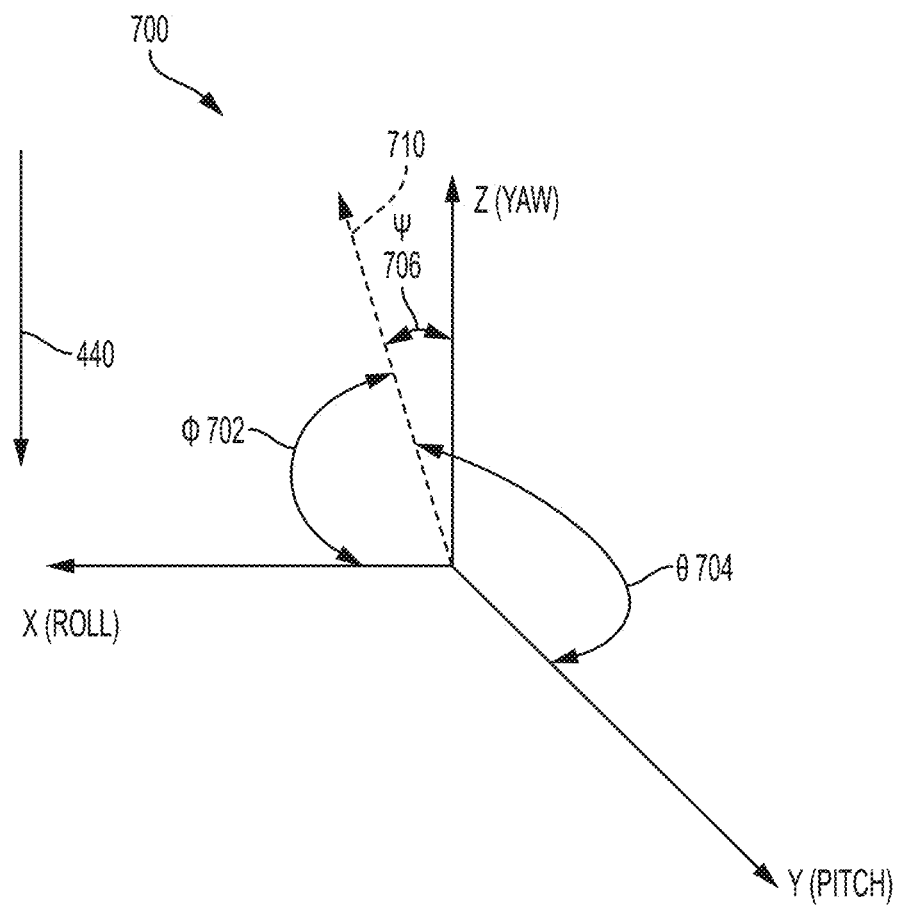

FIG. 7B illustrates that wearable device 100 can make rotational movement with respect to inertial frame of reference 700. In FIG. 7B, an orientation/direction 710 has an angle ($\varphi$) 702 with respect to the positive x-axis, an angle ($\theta$) 704 with respect to the positive y-axis, and an angle ($\psi$) 706 with respect to the positive z-axis. The direction 710 can be expressed in body-fixed frame of reference 700 as [cos($\varphi$), cos($\theta$), cos($\psi$)], which is a non-limiting example/format of the second set of rotational data.

Figure 7C:
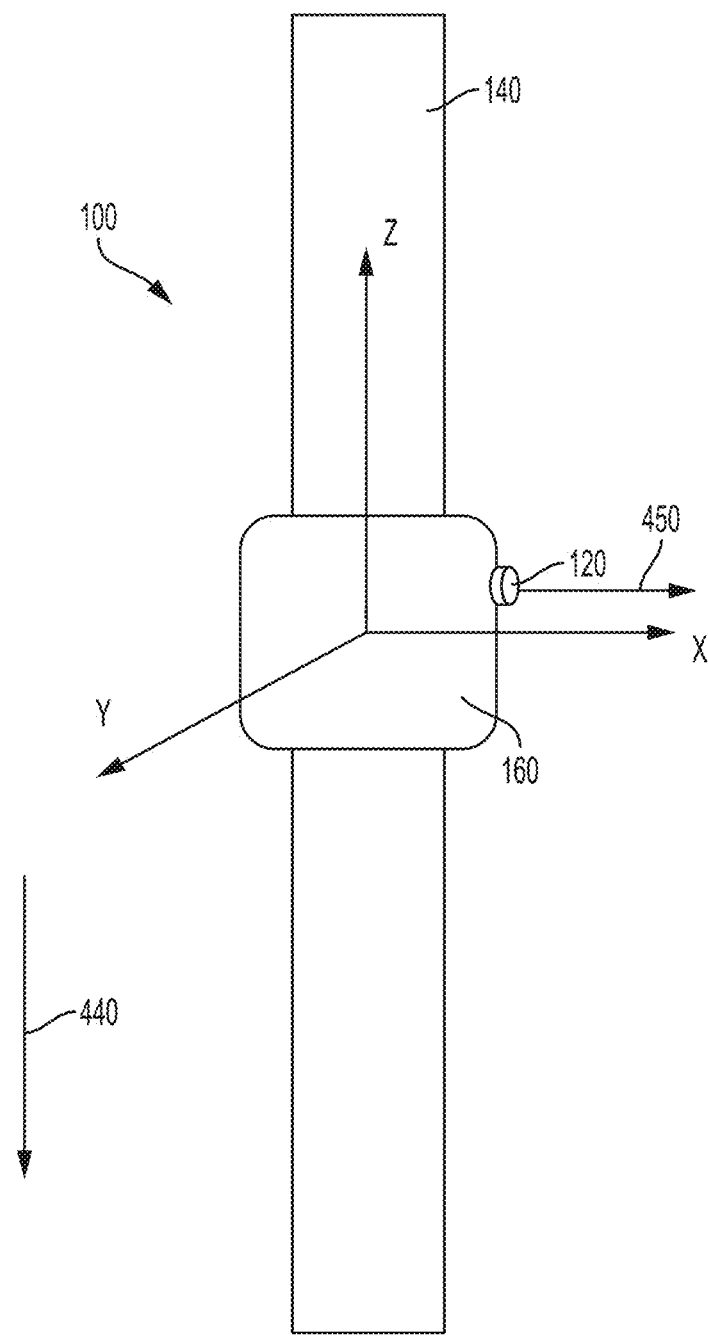
Figure 7D:
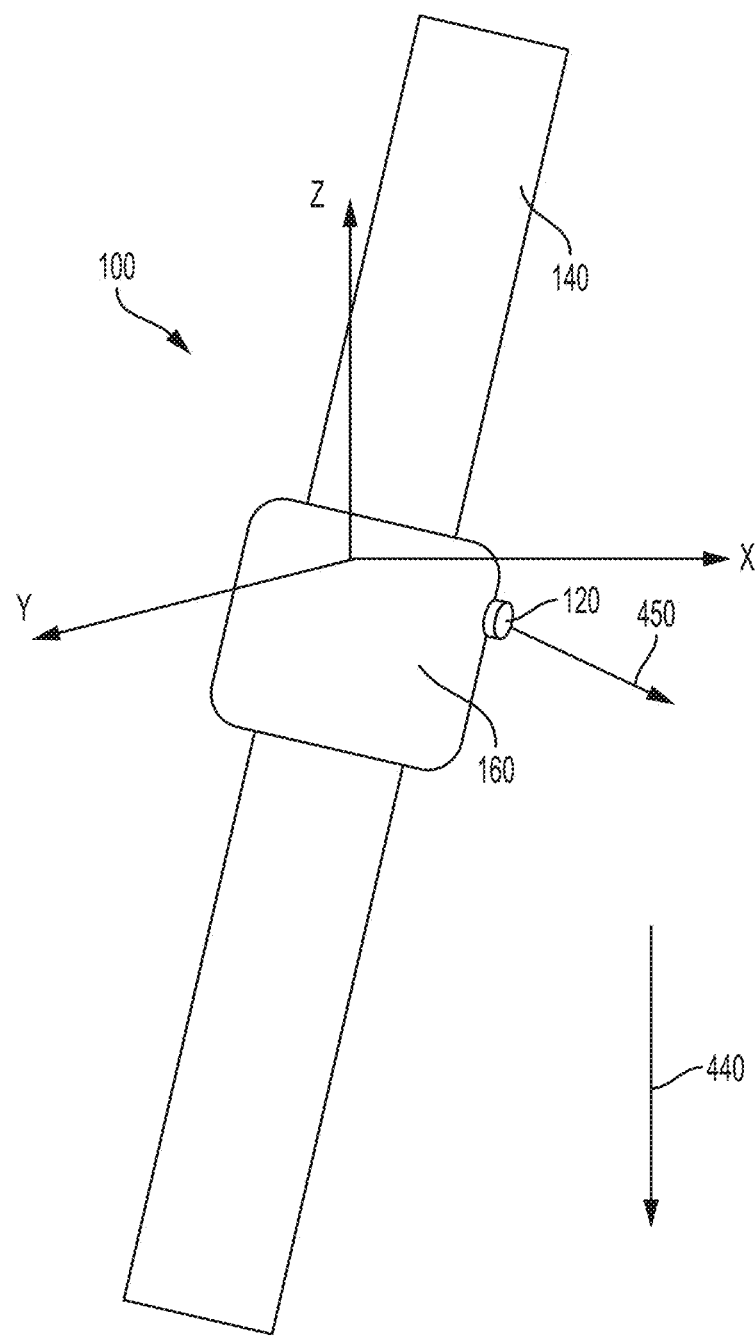

FIGS. 7C and 7D illustrate how same orientations in FIGS. 4C and 4D can be expressed differently in inertial frame of reference 700. In FIG. 7C, wearable device 100 is held vertically, which is the same as FIG. 4C. As discussed earlier, the z-axis is based on the gravity in inertial frame of reference 700. In FIG. 7C, the positive z-axis is chosen as the direct opposite position of gravity, the x-axis is perpendicular to the z-axis and pointing right horizontally, and the y-axis is perpendicular to both x-axis and y-axis and pointing "out" of FIG. 7C. Direction 450 in FIG. 7C represents the direction pointed by crown 120, so the angle ($\varphi$) between direction 450 and the positive x-axis is 0-degree; the angle ($\theta$) between direction 450 and the positive y-axis is 90-degree; and the angle ($\psi$) between direction 450 and the positive z-axis is 90-degree. Therefore, direction 450 can be expressed as [cos(0), cos(90), cos(90)], which is [1, 0, 0]. As another example, direction 440 represents direction of gravity in FIG. 7C and is parallel with and pointing toward the negative z-axis, so the angle ($\varphi$) between direction 440 and the positive x-axis is 90-degree; the angle ($\theta$) between direction 440 and the positive y-axis is 90-degree; and the angle ($\psi$) between direction 440 and the positive z-axis is 180-degree. Therefore, direction 440 in FIG. 7C can be expressed as [cos(90), cos(90), cos(180)], which is [0, 0, −1].

In FIG. 7D, wearable device 100 is rotated 45-degree clockwise compared with FIG. 7C. Because the three axes are based on gravity, they can remain the same as FIG. 7C. Direction 450 in FIG. 7D represents the direction pointed by crown 120, and the angle ($\varphi$) between direction 450 and the positive x-axis is 45-degree; the angle ($\theta$) between direction 450 and the positive y-axis is 90-degree; and the angle ($\psi$) between direction 450 and the positive z-axis is 135-degree. Therefore, direction 450 can be expressed as [cos(45), cos(90), cos(135)], which is [0.707, 0, −0.707]. As another example, direction 440 represents direction of gravity in FIG. 7D. The angle ($\varphi$) between direction 440 and the positive x-axis is 90-degree; the angle ($\theta$) between direction 440 and the positive y-axis is 90-degree; and the angle ($\psi$) between direction 440 and the positive z-axis is 180-degree. Therefore, direction 440 in FIG. 7D can be expressed as [cos(90), cos(90), cos(180)], which is [0, 0, −1].

It is noted that the expression of gravity direction 440 is the same in FIG. 7C and FIG. 7D even though wearable device 100 has rotated. This is because the inertial frame of reference 700 is always fixed with respect to gravity. As a result, when position of wearable device 100 changes, the three axes in inertial frame of reference 700 do not move along. On the other hand, the direction 450 does move with respect to the three axes, so the expression of direction 450 can be changed in the inertial frame of reference 400 even though it is fixed in body-fixed frame of reference 400.

Figure 8:
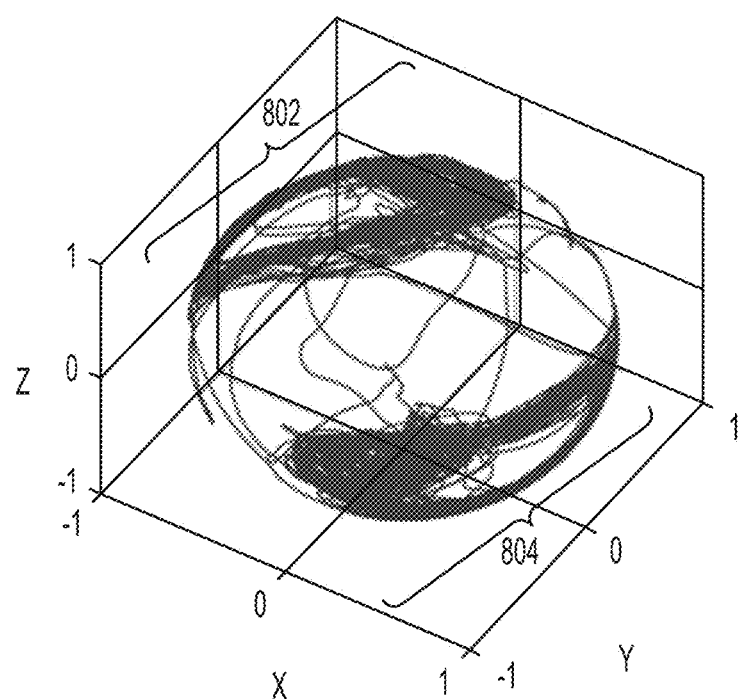
FIG. 8 illustrates a set of rotational data of a wearable device in an inertial frame of reference according to some embodiments of the present disclosure.

FIG. 8 illustrates a first set of rotational data of wearable device 100 according to some embodiments of the present disclosure. Specifically, FIG. 8 illustrates estimation of crown direction in the inertial frame of reference 700 while a user is swimming laps. The x-axis shows cos*, where (I) is the angle between crown direction and the positive x-axis in the inertial frame of reference 700. The y-axis shows cos(θ), where θ is the angle between crown direction and the positive y-axis in the inertial frame of reference 700. The z-axis shows cos(ψ), where ψ is the angle between crown direction and the positive z-axis in the inertial frame of reference 700. For example, if at a moment wearable device 100 is facing up toward the sky, display surface is parallel with the ground, and crown is toward the positive x-axis, then the crown direction can be expressed as [1, 0, 0]; if wearable device 100 is making a yaw movements, and crown is toward the negative x-axis, then the crown direction can be expressed as [−1, 0, 0]. As another example, if crown is pointed towards the ground, then the crown direction can be expressed as [0, 0, 1]. The rotational data in FIG. 8 are largely divided into two clusters, 802 and 804, because every time the user makes a turn, the angle φ between crown direction and the positive x-axis in the inertial frame of reference 700 changes substantially around 180-degree. Therefore, rotational data expressed in FIG. 8 can indicate wearable device 100 undergoes a steady-state change in heading when the data are switching from cluster 802 to cluster 804, or vice versa.

Figure 9:
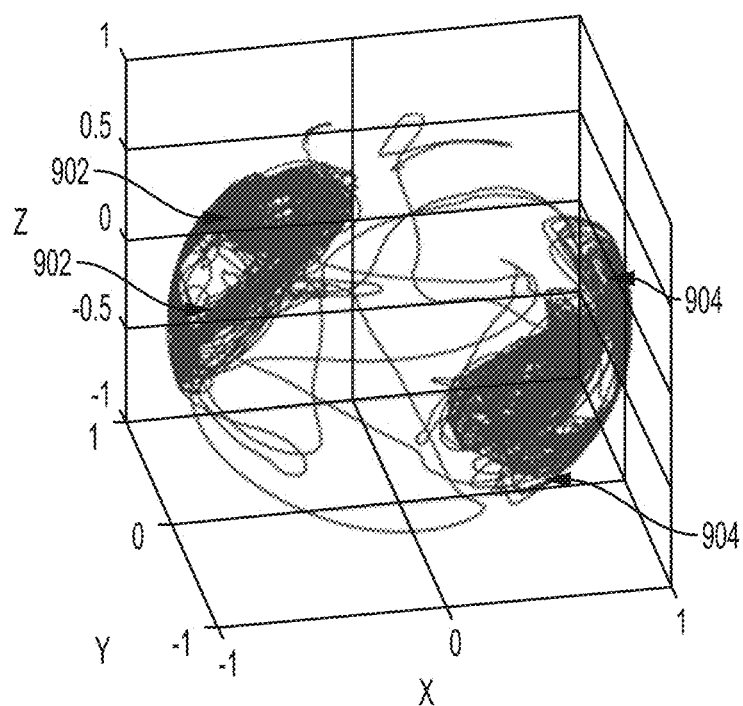
FIG. 9 illustrates another set of rotational data of a wearable device in an inertial frame of reference according to some embodiments of the present disclosure.

FIG. 9 shows rotational data of wearable device 100 during a swimming session, where the rotational data are expressed in an inertial frame of reference. The rotational data in FIG. 9 is largely distributed within two clusters—clusters 902 and 904 in FIG. 9; when the traces of the rotational data switch from one cluster to the other cluster, the switch indicates that the yaw rotational data are changing significantly, which implies the user is making a turn. In some embodiments, to more clearly indicate the user is making a turn from the rotational data, the rotational data can be filtered to remove the "disturbance" caused by the user's regular strokes. In some embodiments, the rotational data can be low-pass filtered based on a time constant that is proportional to a period that the user needs to complete a stroke. In some embodiments, the time constant can be set by a user. In some embodiments, wearable device 100 can dynamically set the time constant based on average duration between strokes detected by wearable device 100. For example, if it takes a user three seconds to finish a stroke, then the time constant can be set around or above three seconds so any rotational changes that are frequent (e.g., happen once and more between two consecutive strokes) can be filtered out or attenuated. On the other hand, a user generally makes a turn much less frequent than making a stroke (e.g., if it takes a user 30 seconds to swim a lap, which is a single length of a pool, then the user makes a turn around every 30 seconds), and the less frequent rotational changes will be passed through a low-pass filter. As a result, the filtered rotational data show the more steady-state change of the user's movements.

Figure 10:
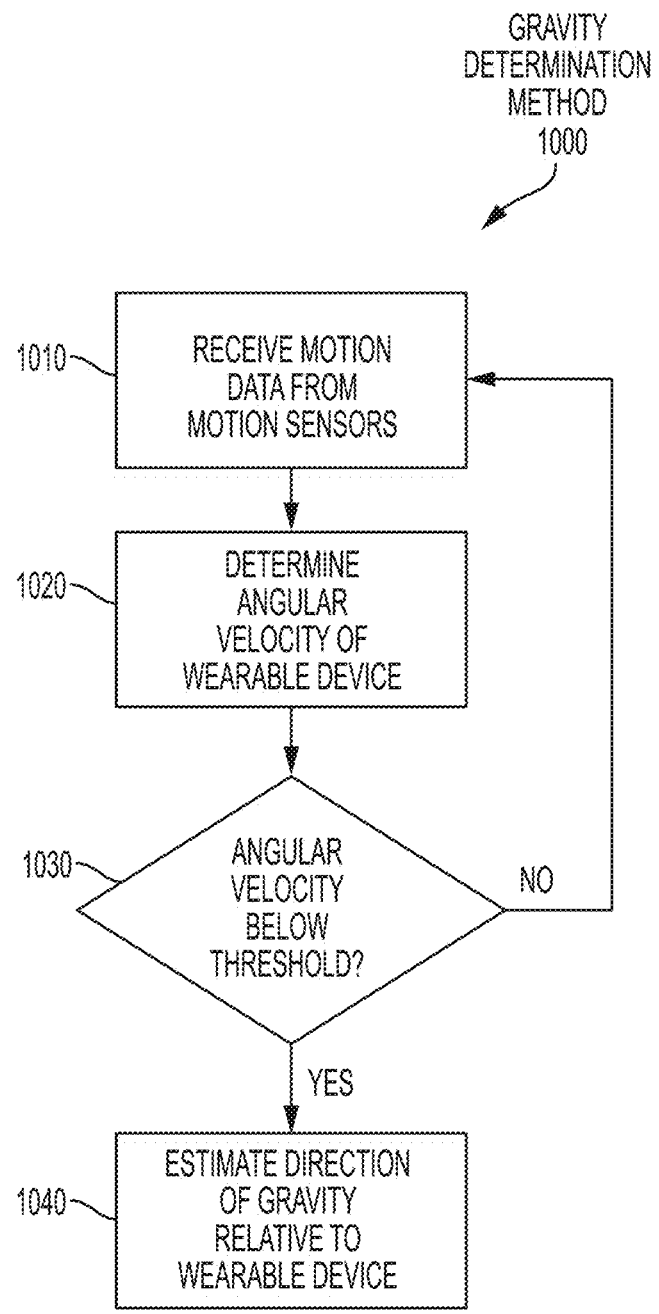
FIG. 10 illustrates a method of determining a direction of gravity according to some embodiments of the present disclosure.

FIG. 10 shows a method 1000 for determining a direction of gravity according to some embodiments of the present disclosure. Knowing the direction of gravity is important to determine a frame of reference for motion information, such as rotational data, of wearable device 100. In some embodiments, method 1000 can be modified by, for example, having steps combined, divided, rearranged, changed, added, and/or removed. Gravity determination method 1000 may begin at step 1010

At step 1010, motion information may be received from the one or more motion sensors 240 on a wearable device (e.g., wearable device 100) of a user. In some embodiments, motion information may include three-dimensional rotational information from one or more sensors 240 such as gyroscope 250 and three-dimensional acceleration information from one or more sensors 240 such as accelerometer 260. In some embodiments, motion information may be filtered such as by a low-pass filter to remove unwanted noise from the ambient.

At step 1020, the angular velocity of wearable device 100 may be determined with respect to a frame of reference such as a body-fixed frame of reference or an inertial frame of reference.

At step 1030, the gravity determination method 1000 may determine whether the angular velocity of wearable device 100 determined at step 1020 is below a threshold. For example, the threshold may be approximately 0.05 radians per second, 0.2 radians per second, or 0.5 radians per second, etc. If the angular velocity exceeds the threshold (e.g., when the user is doing exercise), the gravity determination method 1000 may return to step 1010. In some embodiments, the gravity determination method 1000 may pause or wait for a period of time (e.g., 1 second, 5 seconds, 1 minute, etc.) before proceeding at step 1010.

If the angular velocity is below the threshold (e.g., when the user is relatively still), the gravity determination method 1000 may proceed to step 1040. In some embodiments, at step 1030 wearable device 100 also determines if the magnitude of forces acting on wearable device 100 are approximately equal to the normal force of gravity (1 g) before proceeding to step 1040. If the magnitude is not approximately the normal magnitude, the gravity determination method 1000 may also return to block 1010. Estimating direction of gravity when the angular velocity is below the threshold (e.g., when the user is relatively still) is important because in that way wearable device 100 will not be interfered or confused by acceleration due to other movements. Hypothetically, if wearable device 100 is having a 1 g acceleration along x-axis, then wearable device 100 may be mistaken the direction of gravity.

At step 1040, the direction of gravity relative to wearable device 100 may be estimated. For example, in some embodiments, when wearable device 100 is held relatively still, accelerometer 260 within wearable device 100 may provide data about the direction of forces acting on wearable device 100, which may be attributable primarily to gravity. In some embodiments, gravity determination method 1000 may also determine whether the user wearing wearable device 100 is accelerating (e.g., speeding up or slowing down) or traveling at an approximately constant velocity so as to further improve the estimate of the direction of gravity.

In some embodiments, gravity determination method 1000 may end after outputting the estimated direction of gravity. In other embodiments, the gravity determination method 1000 may return to step 1010 to refine or otherwise repeat the method of estimating the direction of gravity relative to the wearable device.

Figure 11:
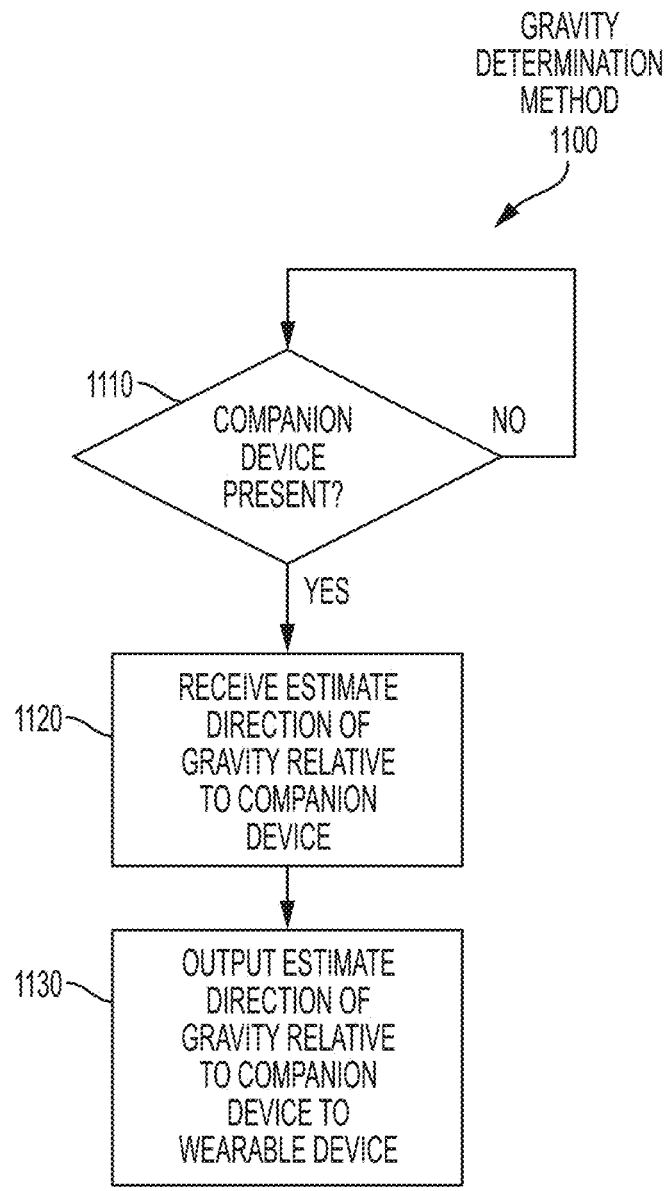
FIG. 11 illustrates a method of determining a direction of gravity according to some embodiments of the present disclosure.

FIG. 11 shows a method 1100 for determining a direction of gravity according to some embodiments of the present disclosure. In some embodiments, the method 1100 can be modified by, for example, having steps combined, divided, rearranged, changed, added, and/or removed. Gravity determination method 1100 can be used when the user has companion device 300 and may begin at step 1110.

At step 1110, gravity determination method 1100 may periodically or continuously check for the presence of a companion device (e.g., companion device 300). For example, in some embodiments, wearable device 100 may determine whether a connection (e.g., Bluetooth, IEEE 802.11 Wi-Fi, or other wireless or wired communication channel) has been established or may be established with companion device 300. If the companion device 300 is present, gravity determination method 1100 may proceed to step 1120.

At step 1120, the direction of gravity relative to companion device 300 may be estimated. In some embodiments, in contrast to the gravity determination method 1100, it may not be necessary to check whether the angular velocity of companion device 300 is below a threshold because most or all of rotation of the angular velocity of companion device 300 may be orthogonal to the direction of gravity.

At step 1130, the direction of gravity relative to companion device 300 may be outputted. In some embodiments, the direction of gravity relative to companion device 300 may be combined or otherwise compared with the direction of gravity relative to wearable device 100. In some embodiments, companion device 300 may further determine a rotation rate around the direction of gravity relative to the companion device and output the rotation rate instead of or in addition to the direction of gravity relative to companion device 300.

In some embodiments, gravity determination method 1100 may end after outputting the estimated direction of gravity. In other embodiments, gravity determination method 1100 may return to step 1110 to refine or otherwise repeat the method of estimating the direction of gravity relative to the wearable device.

Detecting Turns

Figure 12:
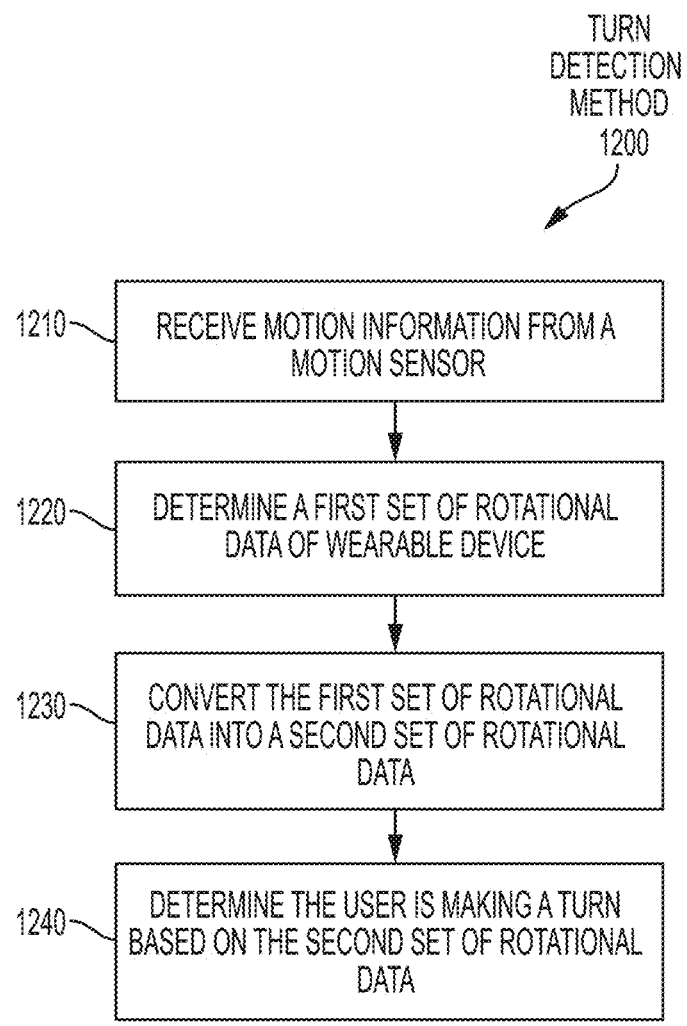
FIG. 12 illustrates a method of determining one or more turns made by a user during a movement according to some embodiments of the present disclosure.

FIG. 12 shows a flow chart illustrating a process 1200 of determining one or more turns made by a user during movements according to some embodiments of the present disclosure. In some embodiments, the process 1200 can be modified by, for example, having steps combined, divided, rearranged, changed, added, and/or removed. As described in more details below, in some embodiments, the process 1200 can include four steps. At step 1210, wearable device 100 receives motion information from one or more motion sensors 240. At step 1220, wearable device 100 determines a first set of rotational data of wearable device 100. At step 1230, wearable device 100 converts the first set of rational data into a second set of rotational data. At step 1240, wearable device 100 determines the user is making a turn based on the second set of rotational data.

At step 1210, motion information may be received from one or more motion sensors 240 on wearable device 100. In some embodiments, motion information may include three-dimensional rotational data of wearable device 100 from gyroscope 250. In some embodiments, motion information may include three-dimensional accelerations of wearable device 100 from accelerometer 260.

At step 1220, wearable device 100 determines a first set of rotational data of wearable device 100 based on the motion information received from one or more motion sensors 240. In some embodiments, the rotational data of wearable device 100 include how wearable device 100 rotates, such as angular velocities of wearable device 100, with respect to a frame of reference. In some embodiments, the first set of rotational data is received from gyroscope 250 and is expressed in a body-fixed frame of reference with respect to wearable device 100.

At step 1230, wearable device 100 converts the first set of rotational data into a second set of rotational data. As described above, rotational data in the body-fixed frame of reference cannot readily indicate whether or not wearable device 100 undergoes movements with respect to external references. To address this issue, wearable device 100 converts the rotational data in the body-fixed frame of reference into rotational data in an inertial frame of reference using techniques appreciated by people skilled in the art such as the one discussed in "Kalman-filter-based orientation determination using inertial/magnetic sensors: observability analysis and performance evaluation," Angelo Maria Sabatini, published Sep. 27, 2011, Sensors 2011, 11, 9182-9206.

At step 1240, wearable device 100 determines that the user wearing wearable device 100 is making a turn based on the set of rotational data expressed in the inertial frame of reference.

Figure 13:
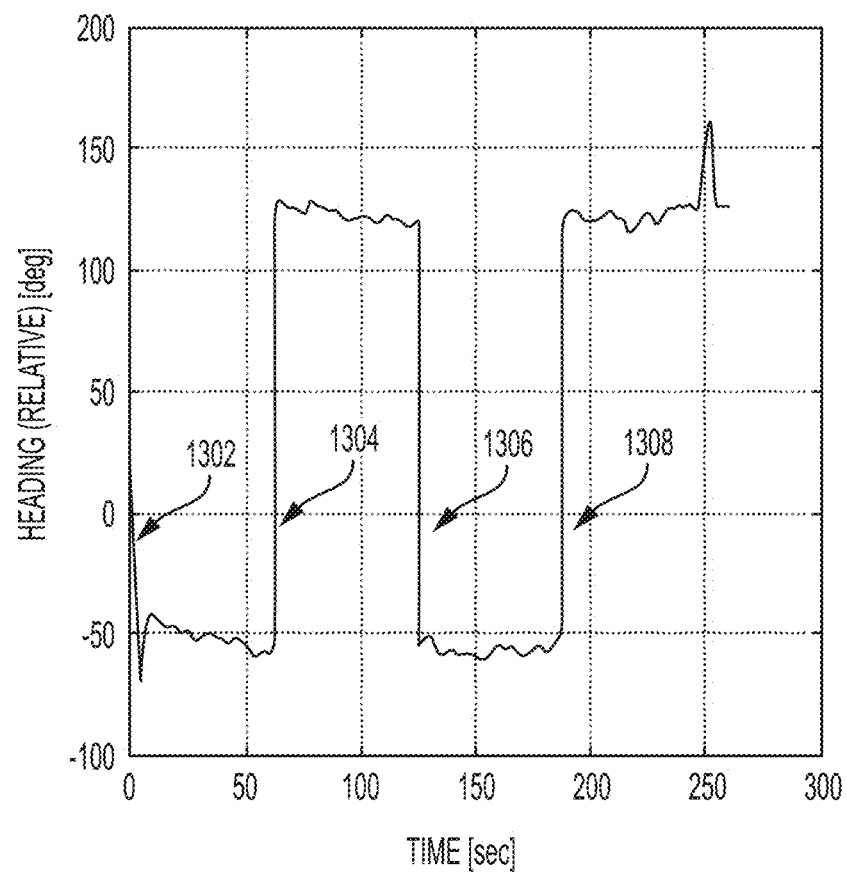
FIG. 13 illustrates filtered yaw data of a wearable device according to some embodiments of the present disclosure.

FIG. 13 illustrates filtered yaw data of a wearable device according to some embodiments of the present disclosure. In some embodiments, the yaw data shown in FIG. 13 are obtained by first projecting the rotational data shown in FIG. 9 into a 2D vector and then filtering the 2D vector. For example, the data in FIG. 9 is a 3D vector that moves in time and can be represented as $i(t)=(x(t), y(t), z(t))$. Then, in some embodiments, $i(t)$ can be projected onto the x-y plane using the gravity vector, and the resulting 2D vector can be represented as $j(t)=(x(t), y(t))$. The x-component and y-component of $j(t)$ are each individually filtered by a low-pass filter as described above. Then the angle plotted in FIG. 13 can be the angle between $j(t)$ at adjacent times to show how $j(t)$ is progressing in time. For example, suppose at $t=0$, $(x=1, y=0)$, and then at $t=1$, $(x=0, y=1)$, then the angle change would be 90 degrees. FIG. 13 shows the yaw data of wearable device 100 worn by a user who completes 4 laps in breaststroke. As described earlier, in an inertial frame of reference, the x-axis and y-axis can be chosen relatively arbitrarily as long as the three axes are perpendicular to each other. Therefore, the filtered yaw data of wearable device 100 in one direction can be around a relatively arbitrary value. For example, FIG. 13 shows the filtered raw data oscillates between two steady-state values, which are roughly 130 degree and −50 degree. The absolute values of the two steady-state yaw data (e.g., 130 degree and −50 degree) are not important; what is more important is that the two steady-state yaw data differ by approximately 180 degree, which implies the user is making a turn. In FIG. 13, the filtered raw data changes abruptly at 1302, 1304, 1306, and 1308 (for example, from 130 degree to −50 degree and/or from −50 degree to 130 degree) when the user is making a turn, and wearable device 100 can detect this abrupt change and determine that the user is making a turn. In some embodiments, the abrupt change can be measured as having at least a threshold change within a threshold period. For example, in some embodiments, if the filtered raw data changes more than 150 degrees per eight seconds, then wearable device 100 can determine that the user is making a turn. In some embodiments, other suitable threshold changes and/or threshold periods can be used.

Detecting Breaths

Figure 14:
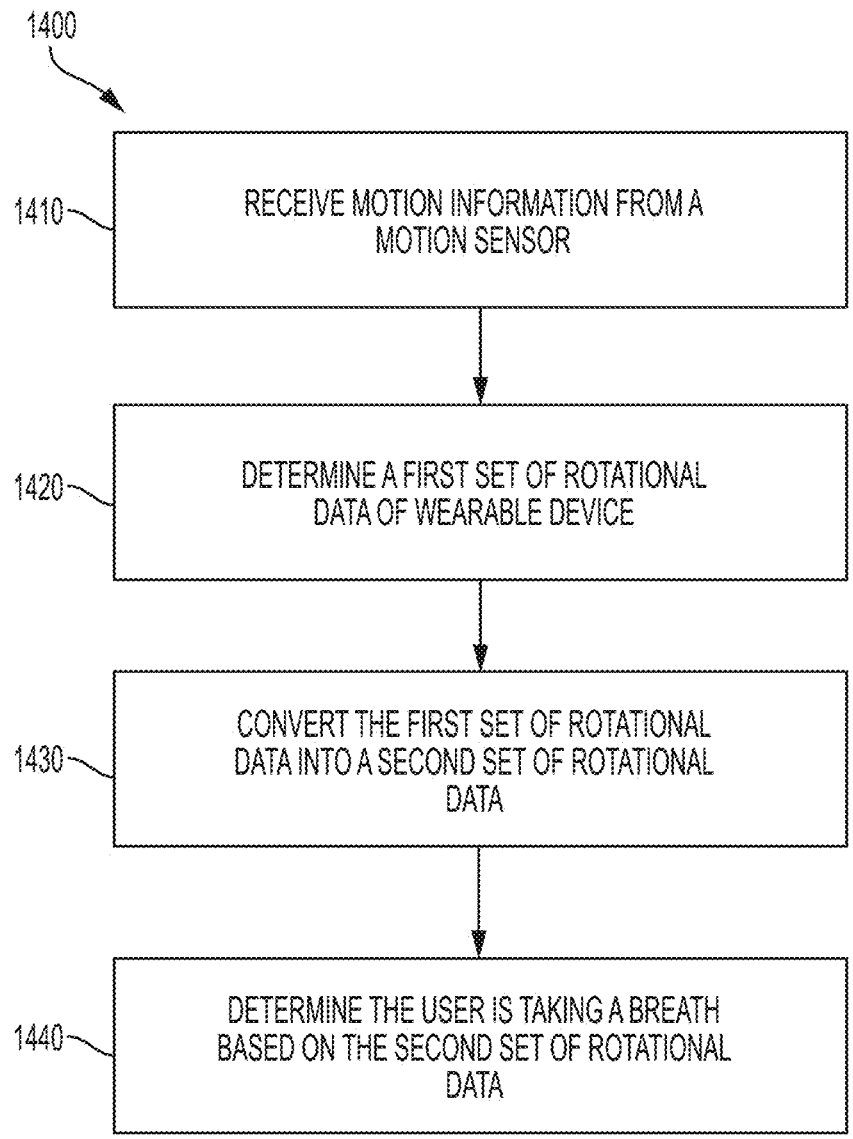
FIG. 14 illustrates a method of determining one or more breaths taken by a user while swimming according to some embodiments of the present disclosure.

FIG. 14 shows a flow chart illustrating a process 1400 of determining one or more breaths taken by a user while swimming according to some embodiments of the present disclosure. In some embodiments, the process 1400 can be modified by, for example, having steps combined, divided, rearranged, changed, added, and/or removed. As described in more details below, in some embodiments, the process 1400 can include four steps. At step 1410, wearable device 100 receives motion information from one or more motion sensors 240. At step 1420, wearable device 100 determines a first set of rotational data of wearable device 100. At step 1430, wearable device 100 converts the first set of rotational data into a second set of rotational data, where the second set of rotational data include pitch rotational data. At step 1440, wearable device 100 determines the user is taking a breath based on the second set of rotational data by monitoring the pitch rotational data exceeding a threshold.

At step 1410, motion information may be received from one or more motion sensors 240 on wearable device 100. In some embodiments, motion information may include three-dimensional rotational data of wearable device 100 from gyroscope 250. In some embodiments, motion information may include three-dimensional accelerations of wearable device 100 from accelerometer 260.

At step 1420, wearable device 100 determines a first set of rotational data of wearable device 100 based on the motion information received from one or more motion sensors 240. In some embodiments, the rotational data of wearable device 100 include how wearable device 100 rotates, such as angular position, angular velocity, and/or angular acceleration of wearable device 100, with respect to a frame of reference. In some embodiments, if the rotational data of wearable device 100 is angular acceleration, then angular velocity and/or angular position can be obtained by integrating the angular acceleration over time. Likewise, if the rotational data of wearable device 100 is angular velocity, then angular position can be obtained by integrating the angular velocity over time. In some embodiments, the first set of rotational data is received from gyroscope 250 and is expressed in a body-fixed frame of reference with respect to wearable device 100.

At step 1430, wearable device 100 converts the first set of rotational data into a second set of rotational data. As described above, rotational data in the body-fixed frame of reference cannot readily indicate whether or not wearable device 100 undergoes movements with respect to external references. To address this issue, wearable device 100 converts the rotational data in the body-fixed frame of reference into rotational data in an inertial frame of reference using techniques appreciated by people skilled in the art such as the one discussed in "Kalman-filter-based orientation determination using inertial/magnetic sensors: observability analysis and performance evaluation," Angelo Maria Sabatini, published Sep. 27, 2011, Sensors 2011, 11, 9182-9206.

At step 1440, wearable device 100 determines that the user wearing wearable device 100 is taking a breath based on the second set of rotational data by monitoring the pitch rotational data exceeding a threshold. When the user is swimming in freestyle, breast stroke, or butterfly, the user's breaths are often associated with upward movements of arm/wrist. Accordingly, wearable device 100 can determine that the user takes a breath when the user's arm/wrist is making moving upward.

Figure 15:
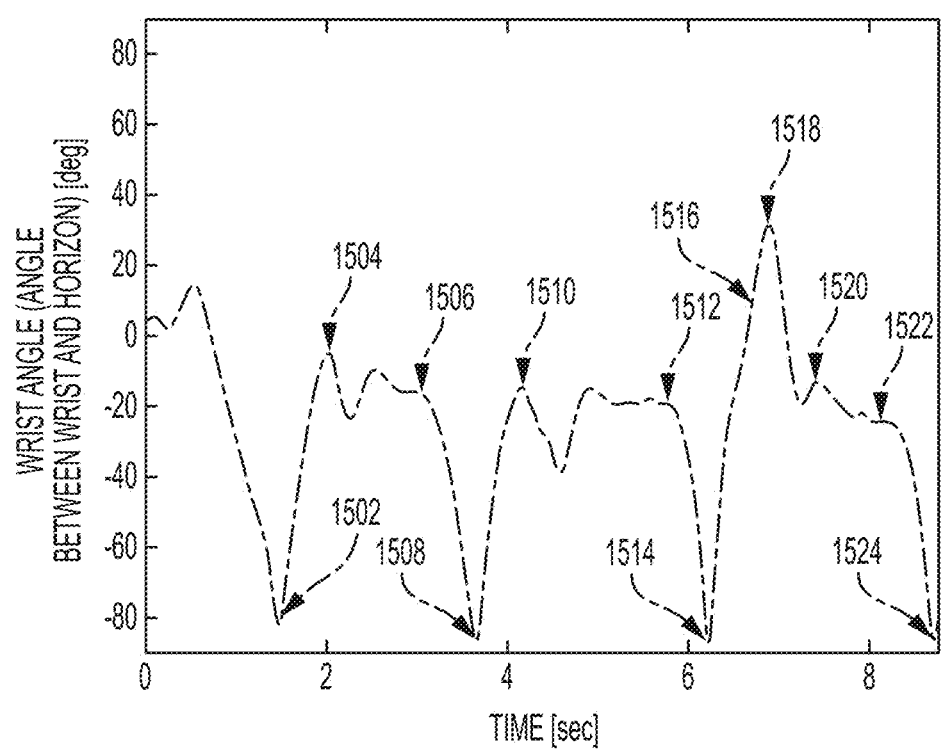
FIG. 15 illustrates wrist angle of a wearable device according to some embodiments of the present disclosure.

FIG. 15 illustrates wrist angle of a wearable device according to some embodiments of the present disclosure. In FIG. 15, the wrist angle is an angle between a user's wrist (the wrist wearing wearable device 100) and horizon while the user is swimming in freestyle. For example, in FIG. 15, the wrist angle at 1502 has about −80 degrees, and this corresponds to the user's arm (the arm with the wrist wearing wearable device 100) in a freestyle motion with the fingers pointing towards the ground during the pull motion in the water. From 1502 to 1504, the wrist angle gradually increases from −80 degrees to 0 degrees, and this corresponds to the user's arm gradually pulling toward the swimmer's hip and eventually leaving the water. From 1504 to 1506, the wrist angle roughly settles between 0 degrees and −20 degrees, and this corresponds to the user's arm gliding. From 1506 to 1508, the wrist angle gradually decreases from roughly −20 degrees to −80 degrees, and this corresponds to the user's arm is pulling toward the ground. The user is then repeating the same stroke phases from 1508 to 1514 as the user did from 1502 to 1508. From 1514 to 1516, the wrist angle gradually increases from −80 degrees to 0 degrees, and this again corresponds to the user's arm is gradually pulling toward the swimmer's hip and eventually leaves the water. Unlike the previous two phases shown in FIG. 15, from 1516 to 1518, the wrist angle continues to increase from 0 degrees to about 30 degrees, and this corresponds to the user's arm spikes towards the sky, which indicates the user's nose and/or mouth is above the water to take a breath. From 1518 to 1520, the user's arm is back to the water level. From 1520 to 1522, the user's arm is gliding. And from 1522 to 1524, the user's arm is again pulling toward the ground. Therefore, in some embodiments, by monitoring the wrist angle, one can deduce the user's stroke phase. For example, when the user is taking a breath in styles such as freestyle or butterfly, the user will have his or her head above the water, and during this time, it is likely that the user's wrist is also above the water with a positive wrist angle or less negative wrist angle. When the user is taking a breath in breaststroke, the user may push his or her wrist further down, and the wrist angle can be more negative than stroke periods without taking a breath. Based on the range of the user's wrist angle and the user's swimming style, a threshold can be chosen to indicate when the user is taking a breath. For example, when the user is swimming freestyle or butterfly, and the range of the user's wrist angle is between −80-degree and 20-degree, the threshold can be selected as top 10% because the user's taking breath is associated with a high wrist angle. That means when the wrist angle is entering the region between 10-degree and 20-degree, the user will be estimated to take a breath. In some embodiments, any other suitable percentage can be selected. As another example, when the user is swimming breaststroke, and the range of the user's wrist angle is between −80-degree and 0-degree, the threshold can be selected as bottom 10% because the user's taking breath is associated with a low wrist angle. That means when the wrist angle is entering the region between −80-degree and −72-degree, the user will be estimated to take a breath. In some embodiments, any other suitable percentage can be selected. In some embodiments, the threshold for determining the user is taking a breath can be dynamically set. For example, by forming a range of angles that a stroke takes, and then using statistical methods to decide if a current stroke looks sufficiently aberrant from the typical stroke.

Counting Swim Strokes

Figure 16:
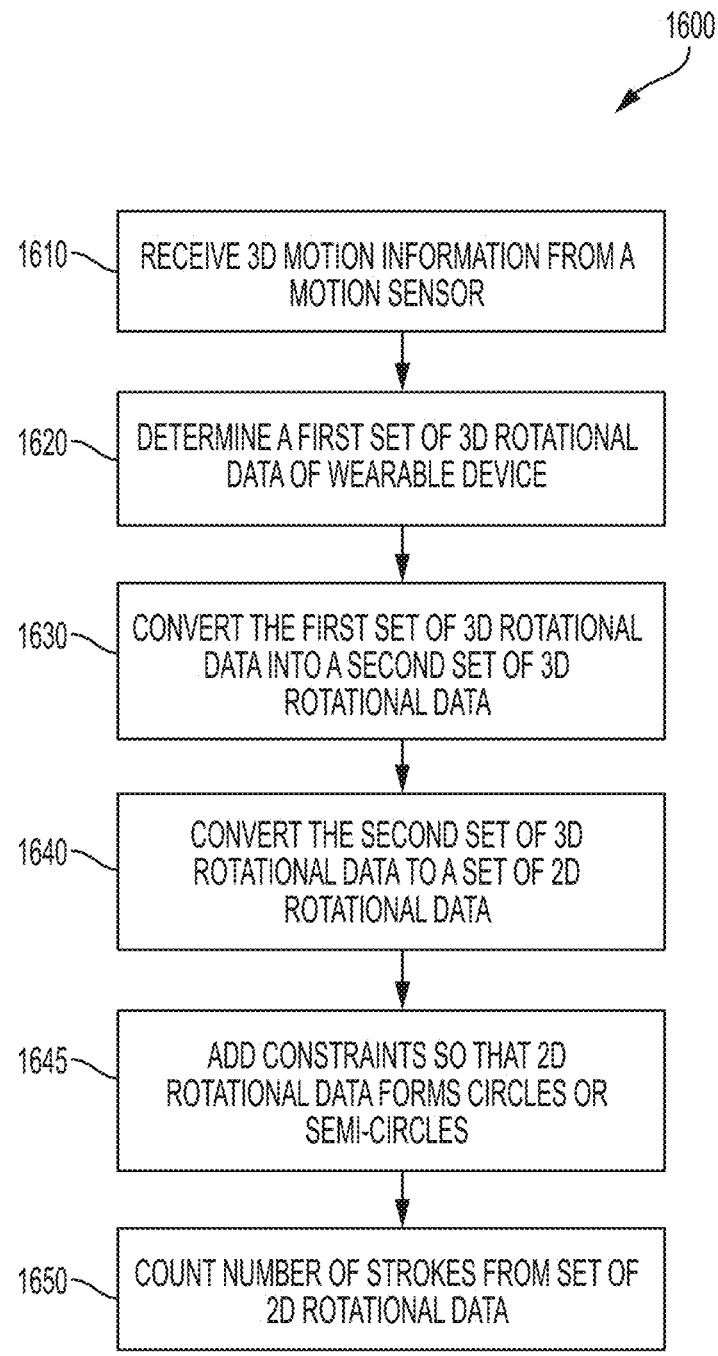
FIG. 16 illustrates a flow chart of a method for counting swim strokes, according to some embodiments of the present disclosure.

FIG. 16 is a flow chart of a method for counting swim strokes 1600, according to some embodiments of the present disclosure. In some embodiments, the method includes the steps of receiving three dimensional motion information from a motion sensor 1610; determining a first set of three dimensional rotational data of a wearable device 1620; converting the first set of three dimensional rotational data into a second set of three dimensional rotational data 1630; converting the second set of three dimensional rotational data to a set of two dimensional rotational data 1640; adding constraints to 2D rotational data to form circles or semi-circles 1645; and counting the number of strokes from the set of two dimensional rotational data 1650.

At step 1610, wearable device 100 receives three dimensional motion information from a motion sensor 240.

At step 1620, the wearable device 100 determines a first set of three dimensional rotational data of the wearable device 100.

At step 1630, wearable device 100 converts the first set of three dimensional rotational data into a second set of three dimensional rotational data. As described above, the three dimensional rotational data in the body-fixed frame of reference cannot readily indicate whether or not wearable device 100 undergoes movements with respect to external references. To address this issue, wearable device 100 converts the three dimensional rotational data in the body-fixed frame of reference into three dimensional rotational data in an inertial frame of reference using techniques appreciated by people skilled in the art such as the one discussed in "Kalman-filter-based orientation determination using inertial/magnetic sensors: observability analysis and performance evaluation," Angelo Maria Sabatini, published Sep. 27, 2011, Sensors 2011, 11, 9182-9206.

When the motion data is transformed to the inertial frame, the data appears as repetitive motion orbits as the user swims. Once it has been determined that the user is swimming, the 3D orbits can be examined in the inertial reference frame using a principal component analysis. For example, the plane that includes the most data points (corresponding to the plane in which the swimmer demonstrates the greatest stroke energy) define the first and second principal component vectors. The third vector that is perpendicular to the first two vectors defines the primary axis of rotation (i.e., the third principal component vector). Once the planes and axis of rotation are determined, the second set of three dimensional rotational data can be projected onto a 2D space (step 1640). The equation for the projection can be expressed as: $R^T(I-ww^T)$ equation (1), where R=rotation, T=matrix transpose, I is the 3×3 identity matrix and w is the third component vector of the PCA.

At step 1645, additional constraints can be added to the 2D rotational data to project rotational data with cleaner orbits and facilitate more reliable stroke counting. In some embodiments, these constraints can be accelerometer energy, moment arm calculations, and/or rotational direction (e.g., clockwise and counterclockwise).

At step 1650, the revolutions of the circles or semi-circles shown in the constrained 2D rotational data can be counted to determine a stroke number.

Figure 17:
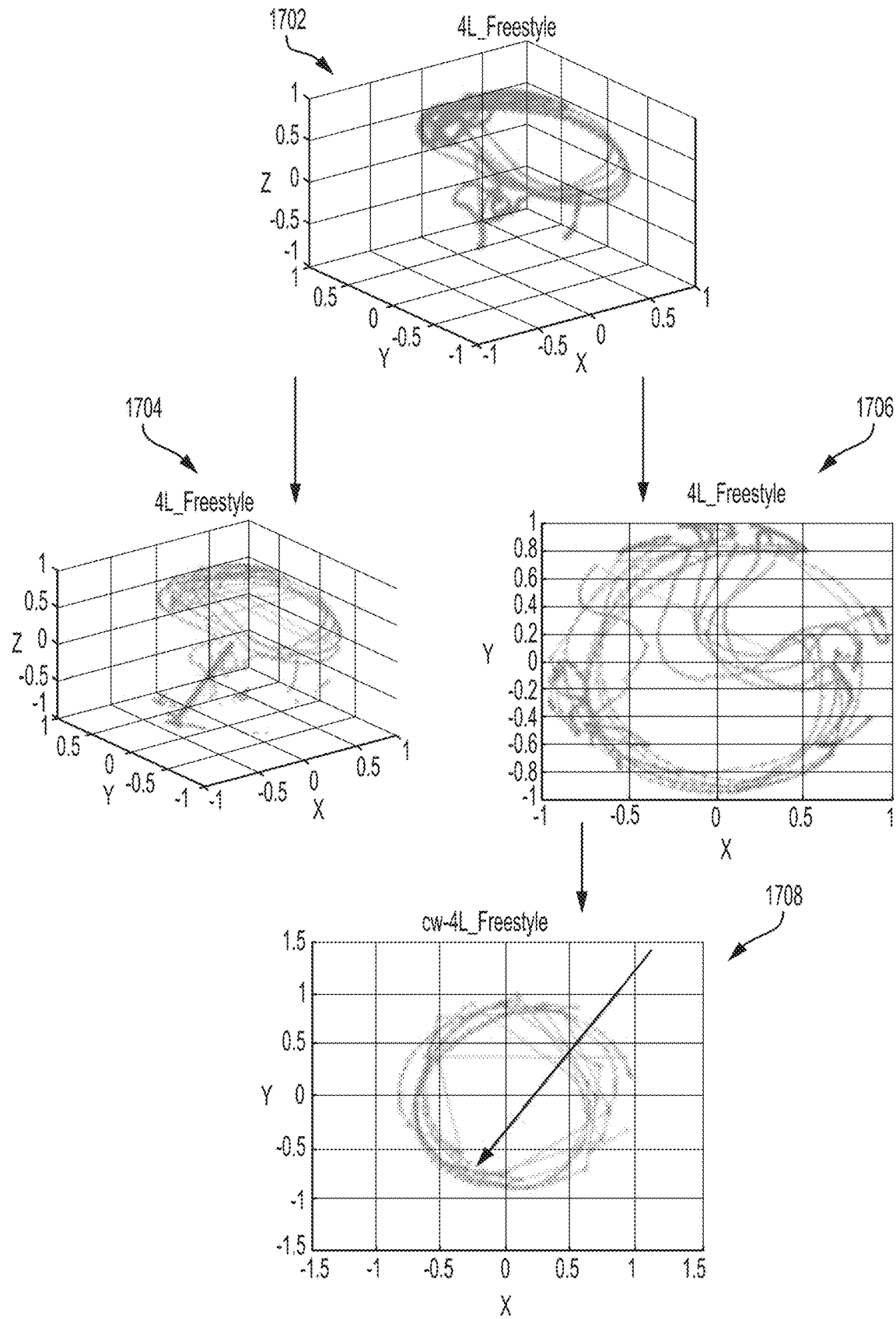
FIG. 17 is a series of graphical representations of the data collected with respect to systems and methods described herein.

FIG. 17 are a series of graphical representations of the data collected with respect to systems and methods described herein. For example, inertial frame data 1702 is shown in three dimensions x, y, z for a freestyle swimmer with time domain sampling. Constrained space domain sampling 1704 of the same three dimensional freestyle data is also shown. Space domain sampling refers to constructing a signal from samples that are a minimum distance apart. For 3D spatial sampling, for example, the distance is specified in a norm-2 manner, where each consecutive sample has a minimum norm-2 distance between them. The three dimensional time and space domain data 1702, 1704 can be converted to a two-dimensional projection 1706 based on a principal component analysis of the 3D data of 1704. In this example, only x and y are shown in the data, the z axis is used as the axis of rotation to transform the data from a three dimensional projection to a two dimensional projection. By adding additional constraints to two dimensional projection 1706, a second two dimensional projection 1708 can be generated that projects a cleaner orbit and facilitates more reliable counting. In some embodiments, these constraints can be accelerometer energy, moment arm calculations, and/or rotational direction (e.g., clockwise and counterclockwise).

In some embodiments, data captured for arm motions that do not show sufficient energy (as measured by the accelerometer) or sufficient extension (as measured by the moment arm calculations) to be considered true swim strokes can be eliminated from the 2D projection.

Figure 18:
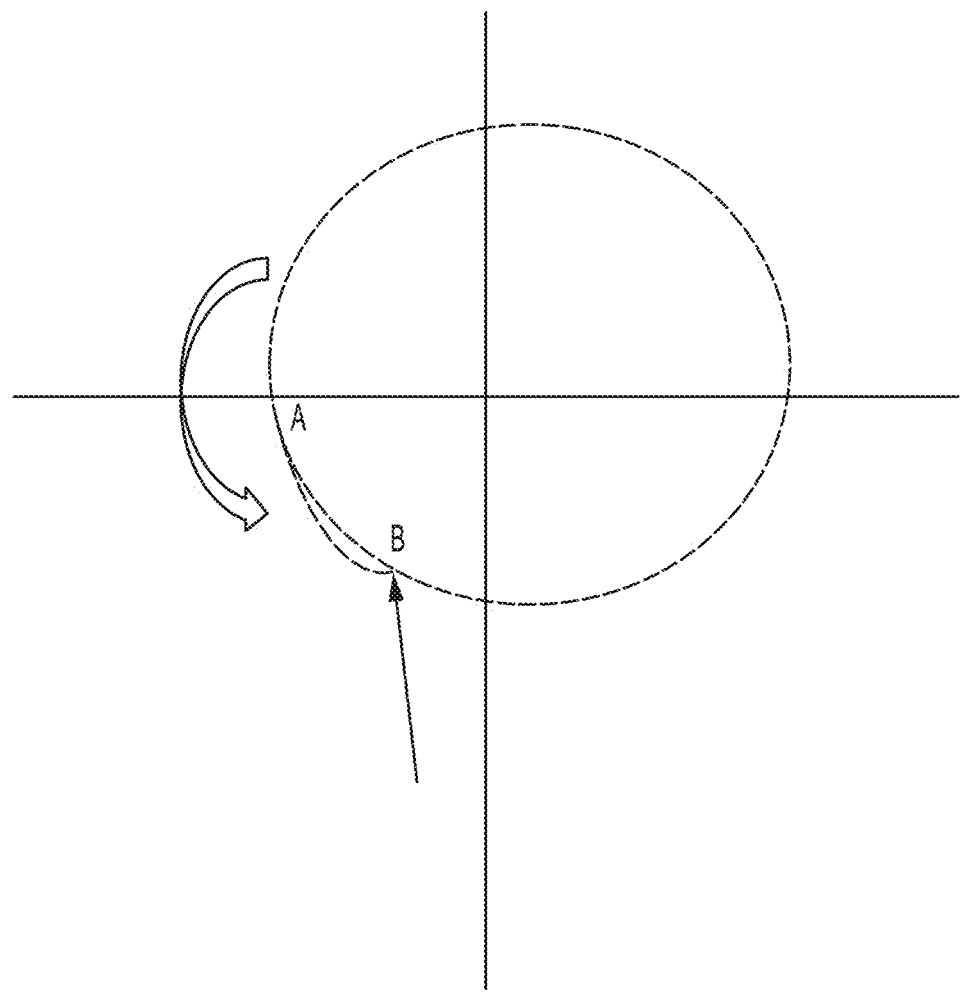
FIG. 18 depicts a sample constraint, according to some embodiments of the present disclosure.

In some embodiments, clockwise and counterclockwise rotational direction data can be used as constraints to eliminate certain data points from the projection. For example, only the clockwise rotational direction data (e.g., for freestyle and butterfly strokes) or the counter clockwise rotational direction data (e.g., for backstroke) can be considered when counting strokes, to eliminate any unintentional gyroscope drift when executing a stroke. For example, FIG. 18 depicts counter clockwise rotational data for a backstroke that includes some drift in the opposite rotational direction between points A and B. At point B, the backstroke starts going off course and exhibits a clockwise motion. The clockwise motion is not considered for stroke counting, and once the stroke resumes its counterclockwise motion, stroke counting picks up again at point B, the last point before the stroke started going off course.

It is from the representation of the data shown in 2D projection 1708 that the number of revolutions can be counted and can be equated with a number of strokes. In order to determine the number of revolutions, a threshold or a number of thresholds can be established along the path of revolution. For example, if the stroke style yields a full rotation (e.g., backstroke, butterfly and freestyle), then a single threshold can be established along the rotational path. Each time the threshold is crossed, another revolution (which represents a stroke) is counted. A threshold is crossed when there is a data point before and after the threshold line.

In some embodiments, when a stroke style only exhibits a partial revolution, instead of a full revolution (e.g., breaststroke), multiple thresholds can be established along a rotational path (e.g., at 45° intervals) to capture the stroke somewhere along its semi-rotational path. When the motion that exhibits a partial rotation crosses one of the established thresholds, the partial rotation can be counted.

Figure 19:
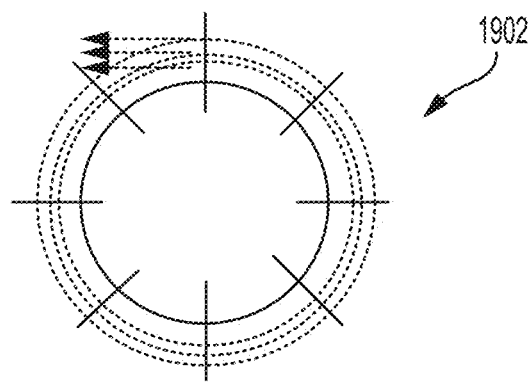
FIG. 19 depicts sample stroke counts, according to some embodiments of the present disclosure.
Figure 19:
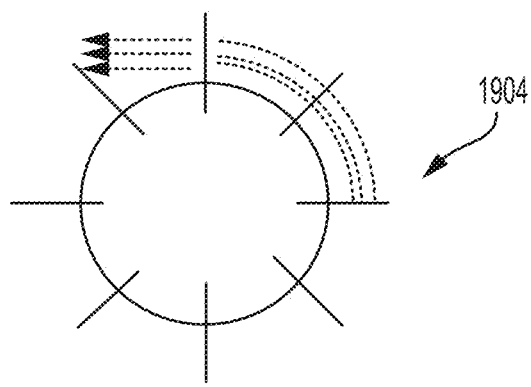
Figure 19:
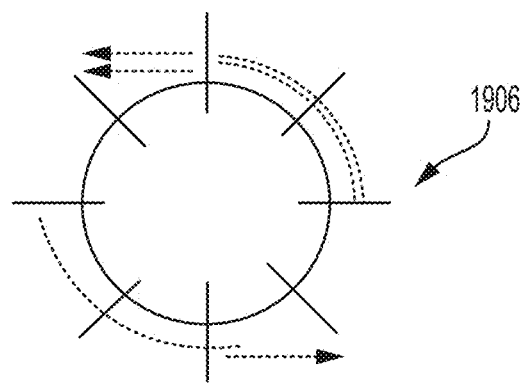

FIG. 19 depicts sample stroke counts, according to some embodiments of the present disclosure. For example, stroke count 1902 represents three full circles, which represents three strokes of a stroke such as backstroke. Stroke count 1904, represents three semi-circles, which could equate to three strokes of breast stroke. Stroke count 1906 can represent three strokes or semi-circles, which can correspond to breaststroke with either a lap change (showing the change in direction) or the change could also be associated with gyroscope drift.

In some embodiments, the system and method can include a spurious stroke check module to eliminate arm motions that are not true strokes. For example, the system and method of the present disclosure can include a voting mechanism module that only counts strokes when they are not too far spread out in time, before committing these strokes as real strokes.

Counting Laps

The present disclosure describes ways to determine the number of laps a swimmer swims in a swimming session. Generally, when a swimmer reaches an end of a swimming lap, he or she will turn to continue to swim. Therefore, finishing a lap is typically associated with a turn made by the swimmer.

In reality, however, a swimmer may be detected to make a turn sometimes even if he or she has not finished a lap. For example, the swimmer may take a goggle break, take an out-of-pool break, make a turn in the middle of the lap, and/or any other activities that may cause the swimmer to intentionally or unintentionally make a turn without reaching the end of a lap. Therefore, a swimmer may be detected to make more than one turn per lap.

Figure 20:
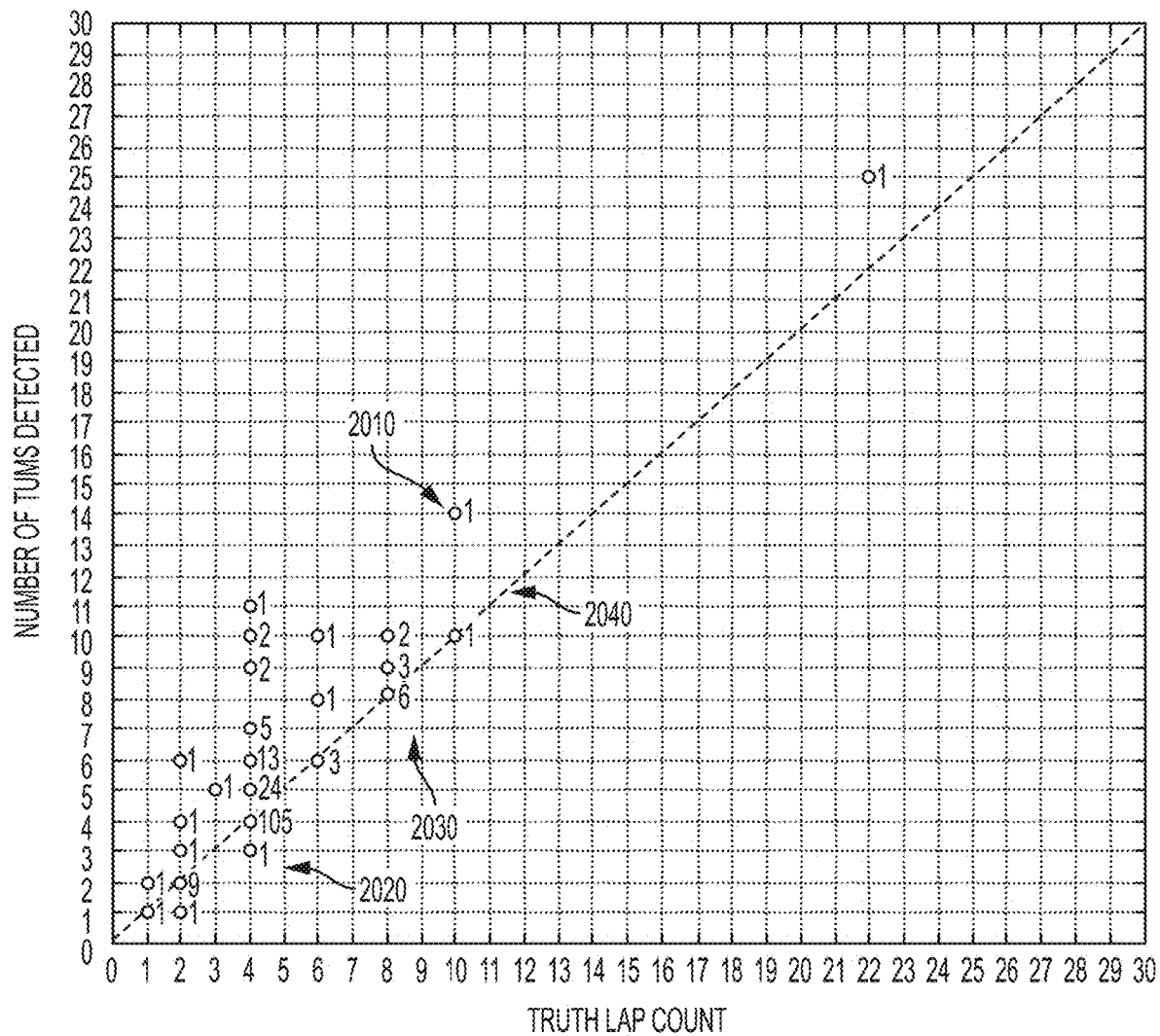
FIG. 20 illustrates a case study comparing the number of turns detected to a truth lap count.

For example, FIG. 20 illustrates a case study associated with 188 swimming sessions. In FIG. 20, the x-axis indicates the number of laps, and the y-axis indicates the number of turns detected. Each point in FIG. 20 represents a swimming session with the number of truth lap count indicated by the corresponding x-axis and the number of turns detected indicated by the corresponding y-axis. And the number next to each point indicates the number of the swimming sessions that has the same associated truth lap count and number of turns detected. For example, 2010 indicates that there is one swimming session that the swimmer swims for 10 laps and is detected to make 14 turns. As another example, 2020 indicates that there is one swimming session that the swimmer swims for four laps and is detected to make three turns. As yet another example, 2030 indicates that there are five swimming sessions that the swimmer swims for eight laps and is detected to make eight turns. The dotted line 2040 has a slope of one in FIG. 20, and it means that any point on the dotted line 2040 has the same number of lap count and turns detected. Because generally each lap should be associated with one turn, the data points above the dotted line 2040 generally indicate false positive of lap count inferred by the number of turns detected, i.e., there are one or more turns that are not associated with turns at the end of a lap. On the other hand, the data points below the dotted line 2040 generally indicate false negative of lap count inferred by the number of turns detected, i.e., there are one or more laps that are not associated with a turn detected. This can be the case when the swimmer continues to another lap without making a turn—for example, the swimmer can first swim in freestyle, and when the swimmer reaches the end of the swimming pool, the swimmer can switch to backstroke without making a turn.

Figure 21:
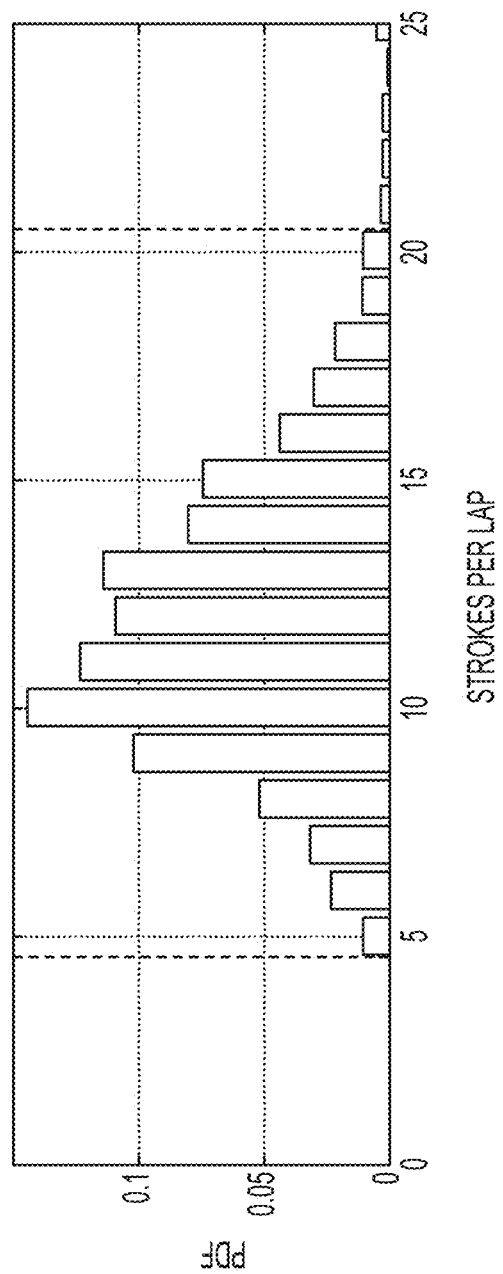
FIG. 21 illustrates a probability distribution function of the number of strokes per lap according to a case study.
Figure 22:
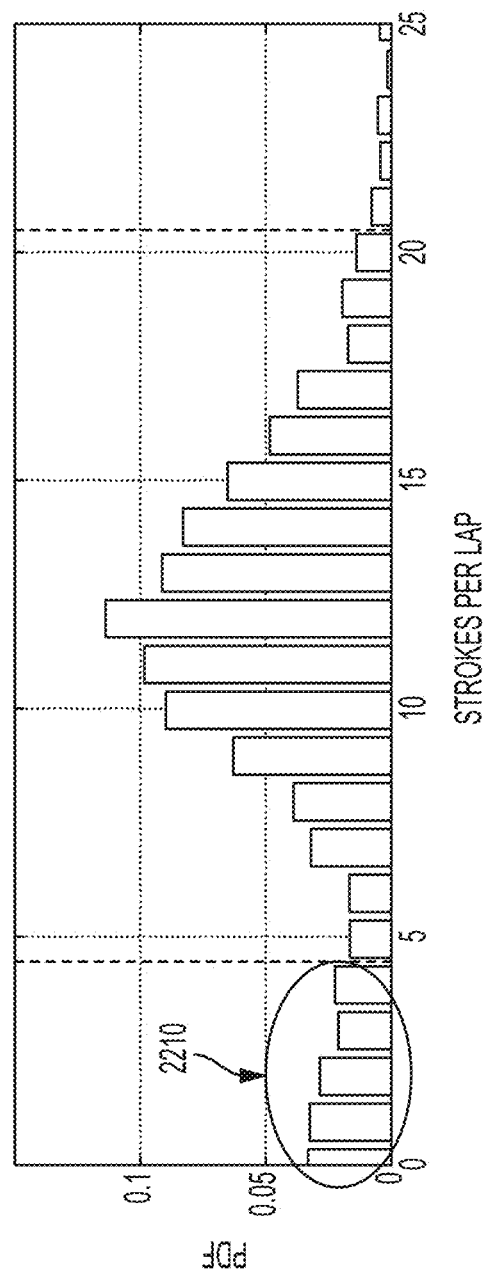
FIG. 22 illustrates a probability distribution function of the number of strokes per lap according to a case study.

When the swimmer makes a turn without finishing a lap, the turn can be referred to as a false or premature turn in that the turn does not correspond to the finish of a lap. One way to determine the false turns is to look at the number of strokes between two consecutive turns. For example, if it generally takes a swimmer 15 to 20 strokes to finish a lap, and if there is only eight strokes between two turns, then at least one turn is a false turn. For example, FIG. 21 shows the probability distribution function of half of the number of strokes per lap according to a case study. In FIG. 21, the x-axis indicates half of the number of strokes per lap in a 25 yards pool, and the y-axis indicates the probability distribution function. FIG. 21 shows half of the number of strokes per lap because FIG. 21 will be compared to FIG. 22, which shows the probability distribution function of the number of detected strokes per lap. Because wearable device 100 can observe only those strokes by the arm wearing wearable device 100, FIG. 21 only shows half of the number of true strokes counted per true lap in order to be consistent. FIG. 21 shows that to finish a lap, the half of the number of strokes can be from five to 25, and it is more likely to be around nine to 15. In FIG. 21, the half of the number of strokes per lap is recorded by a proctor during the swimming session. FIG. 22 also shows the probability distribution function of the number of detected strokes per lap according to the same case study. Unlike FIG. 21, in FIG. 22, a lap is indicated by a turn detected. Comparing to FIG. 21, FIG. 22 shows that sometimes there are less than 5 detected strokes between two consecutive turns, as indicated by 2210. As discussed earlier, these turns are considered false turns in the sense that they do not indicate a true lap because it is generally not very likely for a not highly skilled swimmer to finish a 25-yard lap with less than five detected strokes.

Figure 23:
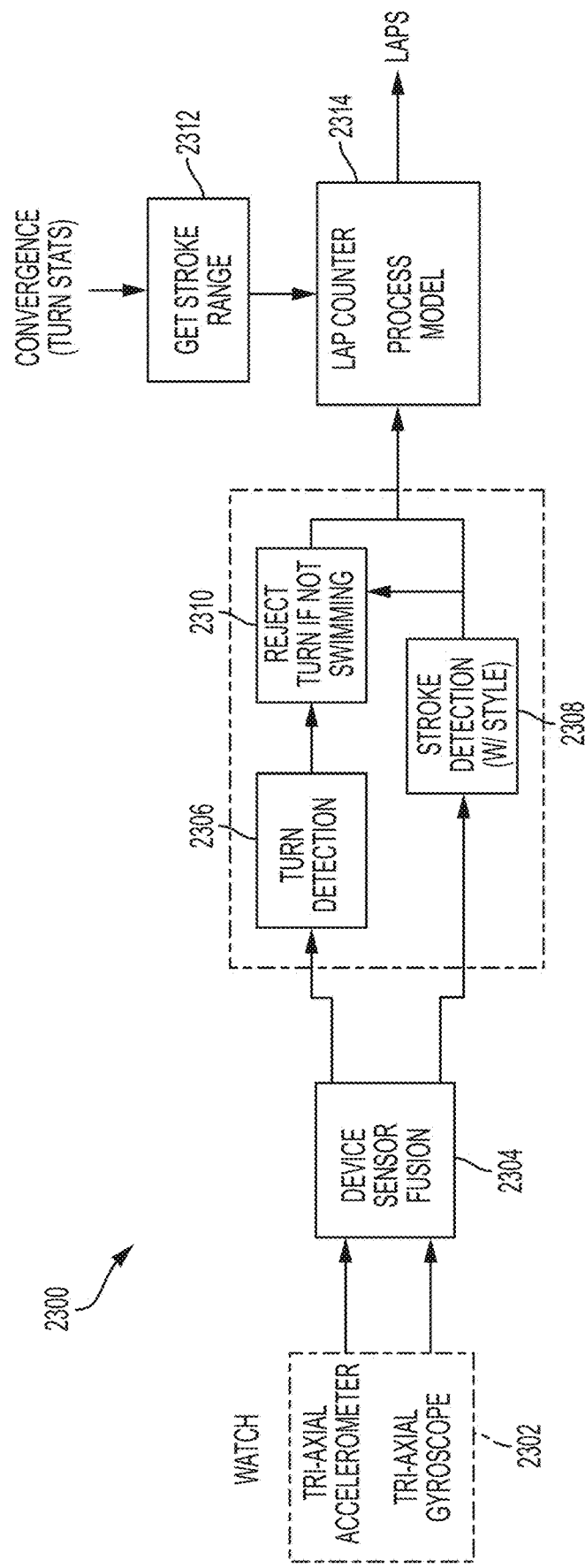
FIG. 23 illustrates a flow chart illustrating a computerized process of determining a number of laps a user swims during a swimming session according to some embodiments of the present disclosure.

FIG. 23 illustrates a flow chart illustrating a computerized process 2300 of determining a number of laps a user swims during a swimming session according to certain embodiments of the present disclosure. In some embodiments, the computerized process 2300 can be modified by, for example, having steps combined, divided, rearranged, changed, added, and/or removed.

At step 2302, motion information may be received from one or more motion sensors 240 on wearable device 100. In some embodiments, motion information may include three-dimensional rotational data of wearable device 100 from gyroscope 250. In some embodiments, motion information may include three-dimensional accelerations of wearable device 100 from accelerometer 260.

At step 2304, wearable device 100 determines rotational data of wearable device 100 expressed in an inertial frame of reference as described above. In some embodiments, wearable device 100 can, additionally or alternatively, include rotational data expressed in a body-fixed frame of reference.

At step 2306, wearable device 100 detects each time the user makes a turn during the swimming session based on the rotational data. In some embodiments, wearable device 100 can detect the user makes a turn.

At step 2308, wearable device 100 detects each time the user makes a stroke and the swimming style associated with the stroke. In some embodiments, wearable device 100 can detect whether or not the user makes a stroke. In some embodiments, wearable device 100 can only detect strokes of the arm wearing wearable device 100. Therefore, in these embodiments, throughout the application, the strokes can be meant strokes detected by wearable device 100 and can be approximately half of the true strokes made by the user. For example, in these embodiments, the number of strokes between turns is the number of strokes detected by wearable device 100 between turns.

At step 2310, wearable device 100 rejects certain turns that are detected at step 2306 based on one or more criteria. One purpose of this step is to reject the turns made by the user while the user is not swimming. In some embodiments, wearable device 100 evaluates a turn based on the stroke, turn, and swimming style detected at steps 2306 and 2308. For example, in some embodiments, when wearable device 100 detects a turn, it will reject the turn unless both of the following two criteria are met. One of the criteria is the stroke rate between two consecutive turns needs to be greater than a minimum stroke rate. The stroke rate can be defined as the number of strokes per minute. In some embodiments, the minimum stroke rate can be eight strokes per minute. In some embodiments, other suitable values can be used as the minimum stroke rate. The other criteria is the number of the strokes with a known style between two consecutive turns needs to be greater than a minimum stroke count. In some embodiments, the minimum stroke count can be three strokes. In some embodiments, other suitable values can be used as the minimum stroke count. In some embodiments, wearable device 100 can reject a turn detected based on less, other, or more criteria. In some embodiments, even if a turn is rejected, the detected turn will still be stored for later adjustment.

At step 2312, wearable device 100 determines a stroke range per lap. In some embodiments, the range is determined based on whether or not the number of the user's strokes converges in the current swimming session or in the historical session. Generally, the number of the user's strokes converges when the variation among the number of strokes per lap is less than a threshold. The details of step 2312 can be further described in connection with FIG. 24 below.

Figure 24:
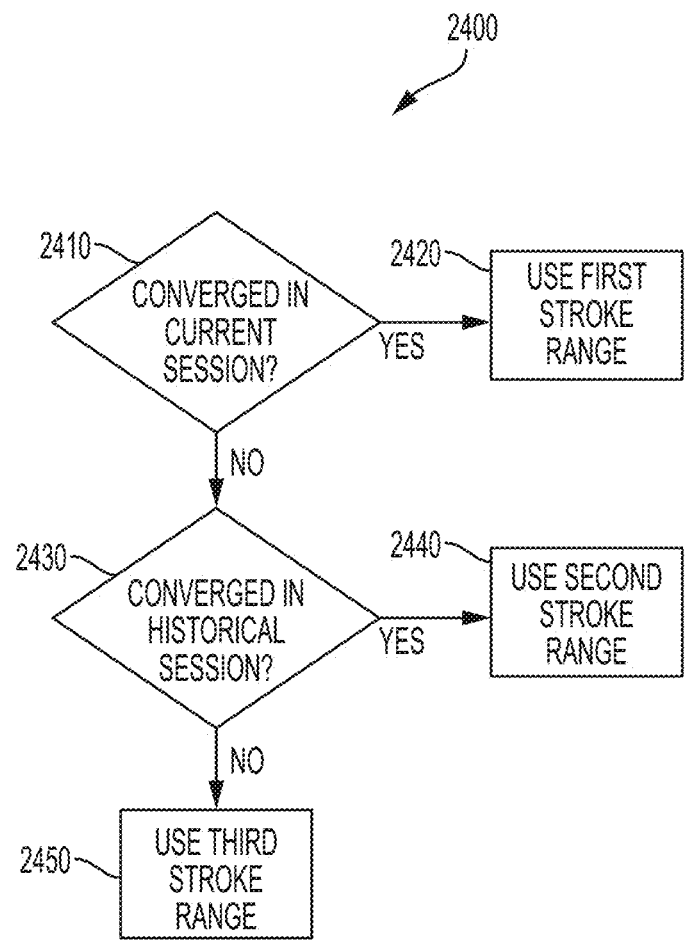
FIG. 24 illustrates a flow chart illustrating a computerized process of determining a stroke range per lap according to some embodiments of the present disclosure.

FIG. 24 illustrates a flow chart illustrating a computerized process 2400 of determining a stroke range per lap according to certain embodiments of the present disclosure. In some embodiments, the computerized process 2400 can be modified by, for example, having steps combined, divided, rearranged, changed, added, and/or removed.

At step 2410, wearable device 100 determines whether the number of the user's strokes converges in the current swimming session. In some embodiments, wearable device 100 checks six consecutive turns and evaluates the number of strokes among the six consecutive turns. For example, the first number of strokes S1 is the stroke count between the user starts to swim and the user makes a first turn detected by wearable device 100; the second number of strokes S2 is the stroke count between the user makes a first turn detected by wearable device 100 and the user makes a second turn detected by wearable device 100; and S3-S6 can be calculated in a similar way. In some embodiments, if the standard deviation of the number of strokes among the six consecutive turns (e.g., S1-S6) is less than a threshold, such as 1.5, wearable device 100 can determine that the number of the user's strokes converges in the current swimming session. In some embodiments, other number of consecutive turns and/or other thresholds of standard deviation can be used to determine whether or not the number of the user's strokes converges in the current swimming session. If the number of the user's strokes converges in the current swimming session, the process 2400 proceeds to step 2420. If the number of the user's strokes does not converge in the current swimming session, the process 2400 proceeds to step 2430.

At step 2420, wearable device 100 determines a stroke range given the number of the user's strokes converges in the current swimming session. In some embodiments, the stroke range can be determined based on the mean value of the number of strokes per lap in the current converged swimming session. For example, if the mean value of the number of strokes per lap in the current converged swimming session is 20 strokes per lap, the range can be +/−6 from the range, i.e., from 14 to 26 strokes per lap. In some embodiments, other suitable ranges can be used.

At step 2430, wearable device 100 determines whether the number of the user's strokes converges in a historical swimming session. In some embodiments, the factor(s) to determine whether or not the number of the user's strokes converges in a historical swimming session can be the same factor(s) used at step 2410. If the number of the user's strokes converges in the historical swimming session, the process 2400 proceeds to step 2440. If the number of the user's strokes does not converge in the historical swimming session, the process 2400 proceeds to step 2450.

At step 2440, wearable device 100 determines a stroke range given the number of the user's strokes converges in the historical swimming session. In some embodiments, the stroke range can be determined based on the mean value of the number of strokes per lap in the historical converged swimming session. For example, if the mean value of the number of strokes per lap in the historical converged swimming session is 16 strokes per lap, the range can be +/−6 from the range, i.e., from 10 to 22 strokes per lap. In some embodiments, the range can be increased for a larger mean value and/or decreased for a smaller mean value. For example, if the mean value of the number of strokes per lap in the historical converged swimming session is 24 strokes per lap, the range can be +/−8 from the range, i.e., from 16 to 32 strokes per lap. In some embodiments, the lower bound of the range can be set at other numbers to take into account the possibility that the current session and the historical session are not associated with the same pool length. For example, in some embodiments, the lower bound can be set at 3 and the upper bound remains at 6 strokes over the mean value. For example, if the mean value of the number of strokes per lap in the historical converged swimming session is 16 strokes per lap, the range can be from 3 to 22 strokes per lap. In some embodiments, other suitable ranges can be used.

At step 2450, wearable device 100 determines a stroke range given the number of the user's strokes does not converge in the current swimming session or in the historical swimming session. In some embodiments, the stroke range can be wider than the ranges determined at step 2320 or 2340 because the number of the user's strokes has not converged yet. In addition, the range can be varied based on the user's swimming style. For example, in some embodiments, if the user is detected to swim in breast stroke, then the range can be from 3 to 72 strokes per lap. In some embodiments, if the user is detected to swim in other styles, then the range can be from 3 to 40 strokes per lap.

As mentioned above, the parameters used in process 1600 can be changed to other suitable values. In addition, in some embodiments, if wearable device 100 first determines the number of the user's strokes does not converge and then later determines the number of the user's strokes converges eventually, then wearable device 100 can adjust the stroke range accordingly.

Now referring back to FIG. 23. At step 2314, wearable device 100 determines lap count of the user during the current swimming session. The details of step 2314 can be further described below in connection with FIG. 25.

Figure 25:
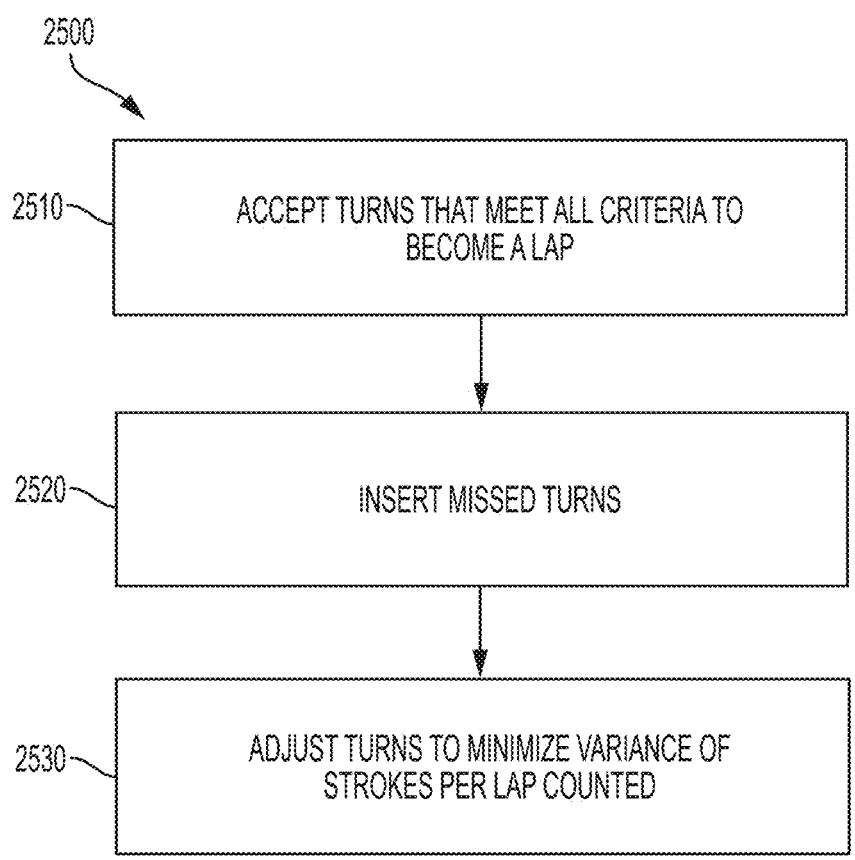
FIG. 25 illustrates a flow chart illustrating a computerized process of determining lap count of the user accordingly to some embodiments of the present disclosure.

FIG. 25 illustrates a flow chart illustrating a computerized process 2500 of determining lap count of the user accordingly to certain embodiments of the present disclosure. In some embodiments, the computerized process 2500 can be modified by, for example, having steps combined, divided, rearranged, changed, added, and/or removed.

At step 2510, wearable device 100 accepts the turns that meet all criteria to become a lap. At step 2510, wearable device 100 has already rejected certain turns. At step 2510, wearable device further rejects a turn if the number of the strokes between the current detected turn and the previous detected turn is outside the stroke range determined at step 1512. In some embodiments, all detected turns, both accepted and rejected, will be kept at a storage for potential adjustment at step 2530.

At step 2520, wearable device 100 inserts a turn if it determines that a turn is not detected. For example, sometimes the user makes a turn with a relatively small change in yaw angle, and wearable device 100 missed detecting this turn. Sometimes if the user reaches the end of the pool using a style other than backstroke and then switches to backstroke to continue, then wearable device 100 may not detect a turn because there may not be much change of yaw angle.

In some embodiments, wearable device 100 can determine there is a missed turn if the number of strokes between two consecutive turns is too large. For example, if in previous turns, the average number of strokes between two consecutive turns is 20, and the number of strokes between the current detected turn and previous detected turn is 40, it is likely that a turn is missed. In some embodiments, wearable device 100 can determine there is a missed turn if the number of the strokes between two turns is greater than a threshold. For example, the threshold can be 1.8 times of the average number of strokes between consecutive turns. In some embodiments, wearable device 100 can also require the threshold is greater than the upper bound of the stroke range. For example, if the average stroke count is 15, and the stroke range is between 9 and 21, then if there are 30 strokes between the current detected turn and the previous turn, wearable device 100 will determine there is a missed turn because 30 is both greater than the upper bound of the stroke range (21) and 1.8 times of the mean value (1.8*15=27). In some embodiments, other suitable parameters can be used to determine whether a turn is missed. In some embodiments, step 2520 is limited to only insert one lap. In some embodiments, step 2520 can insert more than one lap.

At step 2530, wearable device 100 adjusts turns detected to reduce variance of strokes per lap counted. For example, when wearable device 100 rejects a turn, it will consider if accepting the current turn and rejecting the previous accepted turn will reduce variance of strokes per lap counted. Table I shows an example of turns detected by wearable device 100 and the number of strokes associated with two consecutive turns detected. Wearable device 100 would normally reject the fourth turn since it only associated with 3 strokes. In that case, six turns (turns #1, #2, #3, #5, #6, and #7) will be accepted, and the numbers of strokes between two consecutive accepted turns will be 15, 15, 12, 18, 14, and 15. The mean value of the stroke count will be 14.83, and the standard deviation will be 1.94. As discussed above, at step 2530, when wearable device 100 rejects a turn, it will also compare to the previous accepted turn and determine if accepting the current turn and rejecting the previous accepted turn will reduce variance of strokes per lap counted. For example, if wearable device 100 rejected the previously accepted turn #3 and accepted instead turn #4, then the numbers of strokes between two consecutive accepted turns will be 15, 15, 15, 15, 14, and 15. The mean value of the stroke count will be around 14.83, and the standard deviation will be around 0.41. Since the variance of the number of strokes per lap counted will be smaller after adjustment, wearable device 100 will accept turn #4 but reject turn #3.

TABLE I

Turns Detected and the Number of Strokes Detected between Consecutive Turns

| | Turns Detected | | | | | | |
|---|---|---|---|---|---|---|---|
| | 1 | 2 | 3 | 4 | 5 | 6 | 7 |
| number of strokes between consecutive turns | 15 | 15 | 12 | 3 | 15 | 14 | 15 |

Figure 26:
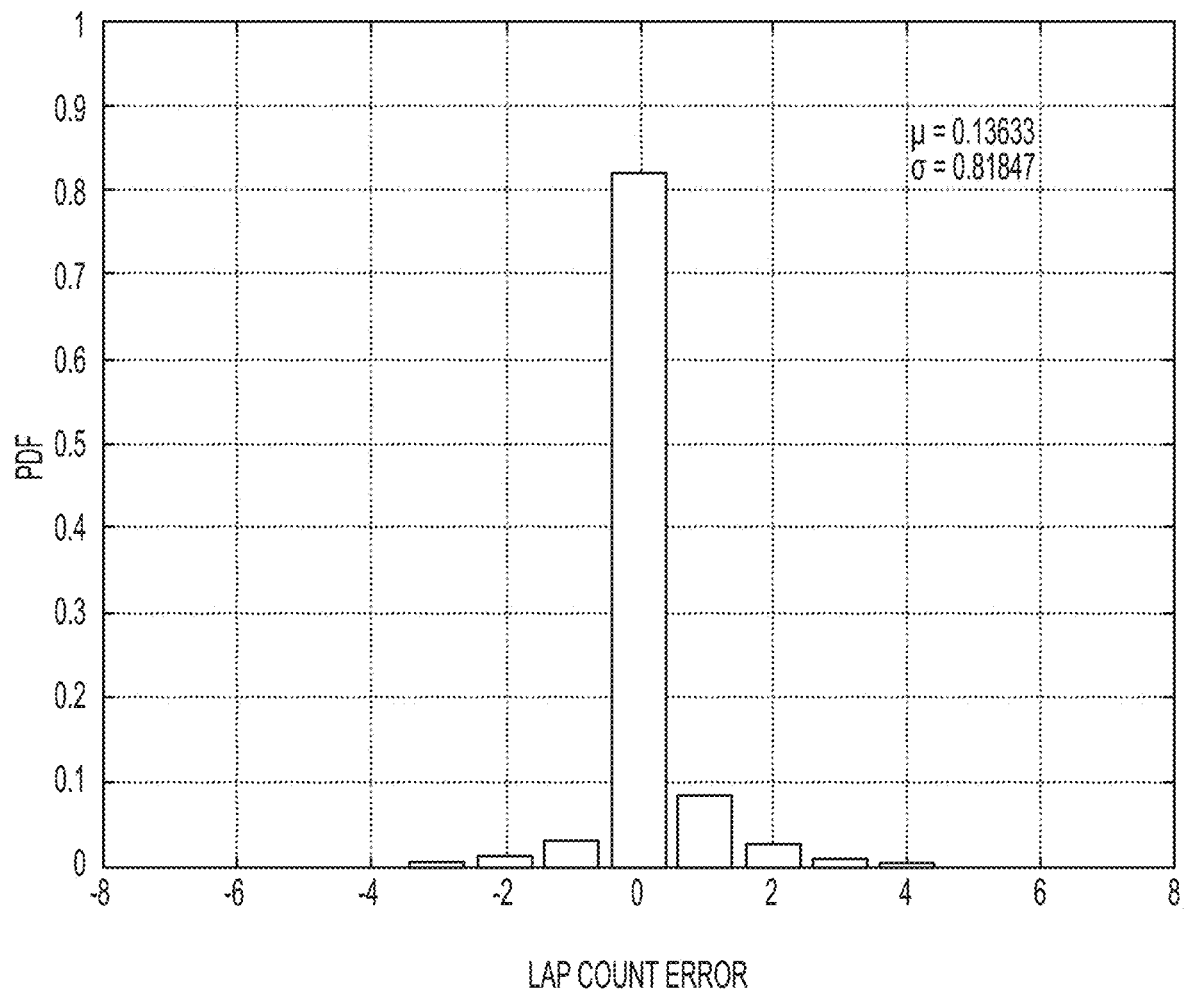
FIG. 26 illustrates a probability distribution function of lap count error using techniques according to some embodiments of the present disclosure.

FIG. 26 illustrates a probability distribution function of lap count error using techniques according to certain embodiments of the present disclosure. In FIG. 26, the x-axis is the difference between the lap count determined by the current invention and the truth lap count. The y-axis is the probability distribution function of different lap count error, where the lap count error can be defined as the laps counted minus the truth lap count. FIG. 26 records results for 1269 session. FIG. 26 illustrates that the techniques described in the present disclosure render a low error between laps counted by wearable device 100 and truth lap count—the mean value of the error is around 0.13633 and standard deviation is around 0.81847.

Figure 27:
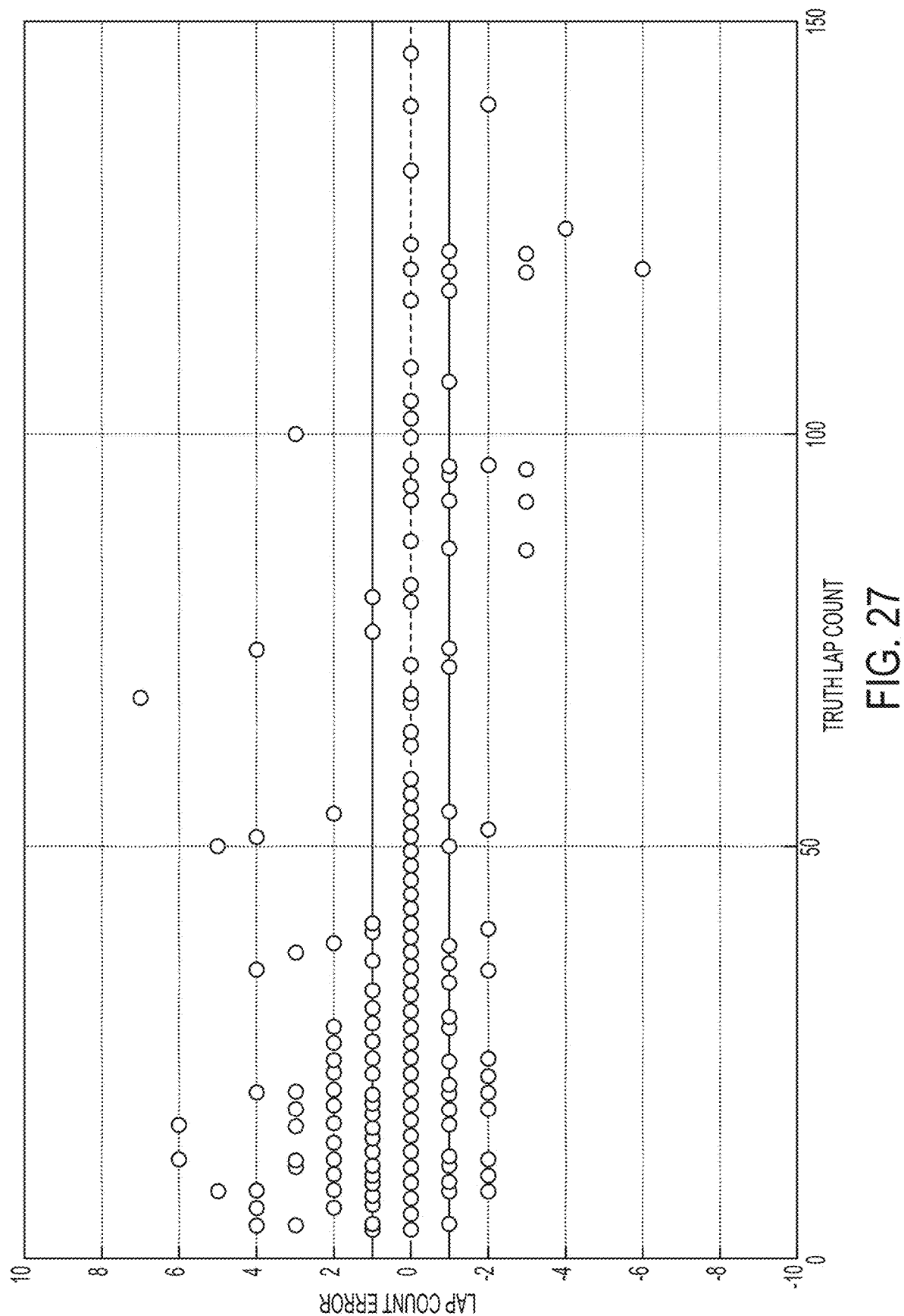
FIG. 27 illustrates lap count error using techniques according to some embodiments of the present disclosure.

FIG. 27 illustrates lap count error using techniques according to certain embodiments of the present disclosure. FIG. 27 records results for 1269 sessions with 24079 total laps. The x-axis is the truth lap count. The y-axis the lap count error. FIG. 27 shows the lap count error is well bounded even for large truth lap count. In other words, the lap count error does not scale with the truth lap count using techniques described in the present disclosure.

Detecting Swim Activity

Figure 28:
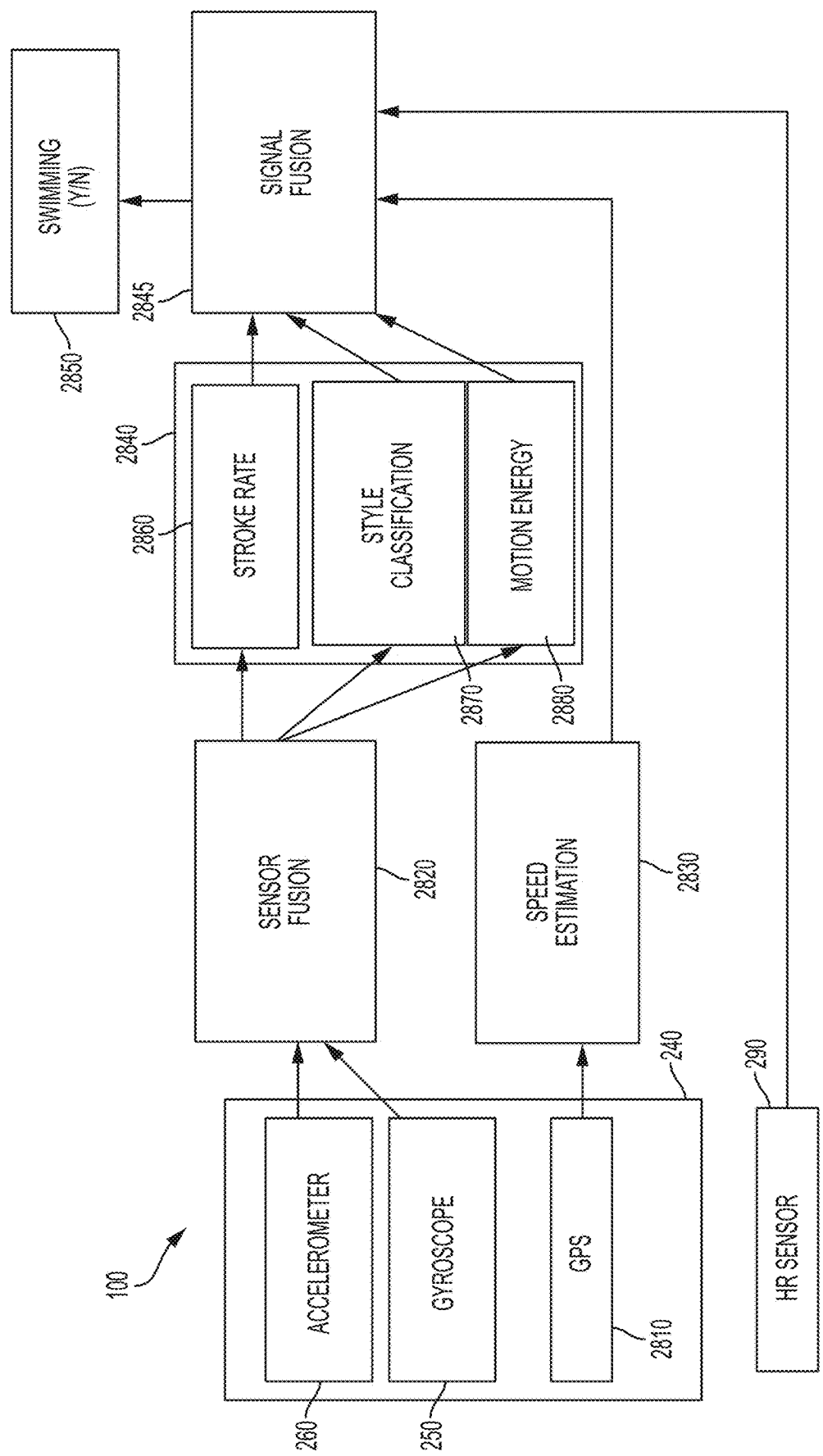
FIG. 28 illustrates exemplary components for detecting swim activity, according to some embodiments of the present disclosure.

FIG. 28 depicts in further detail the components that may be found within wearable device 100 according to some embodiments of the present disclosure for detecting swim activity. In some embodiments, wearable device 100 can include motion sensors 240, including an accelerometer 240, gyroscope 250, and GPS 410; a sensor fusion module 2820, a speed estimation module 2830, a heart rate sensor 290, a sensor processing module 2840, a signal fusion module 2845, and a swimming detection output 2850. Sensor data is collected by the three axis accelerometer 260 and three axis gyroscope 250 in epochs. Each epoch can range from about 1 second to about 10 seconds, an exemplary epoch being 2.56 seconds. The samples are collected in X, Y, and Z axes. The data from motion sensors 240 can be used to determine a stroke rate 2860, stroke classification 2870 and various motion signatures 2880 characteristic of swimming.

Figure 29:
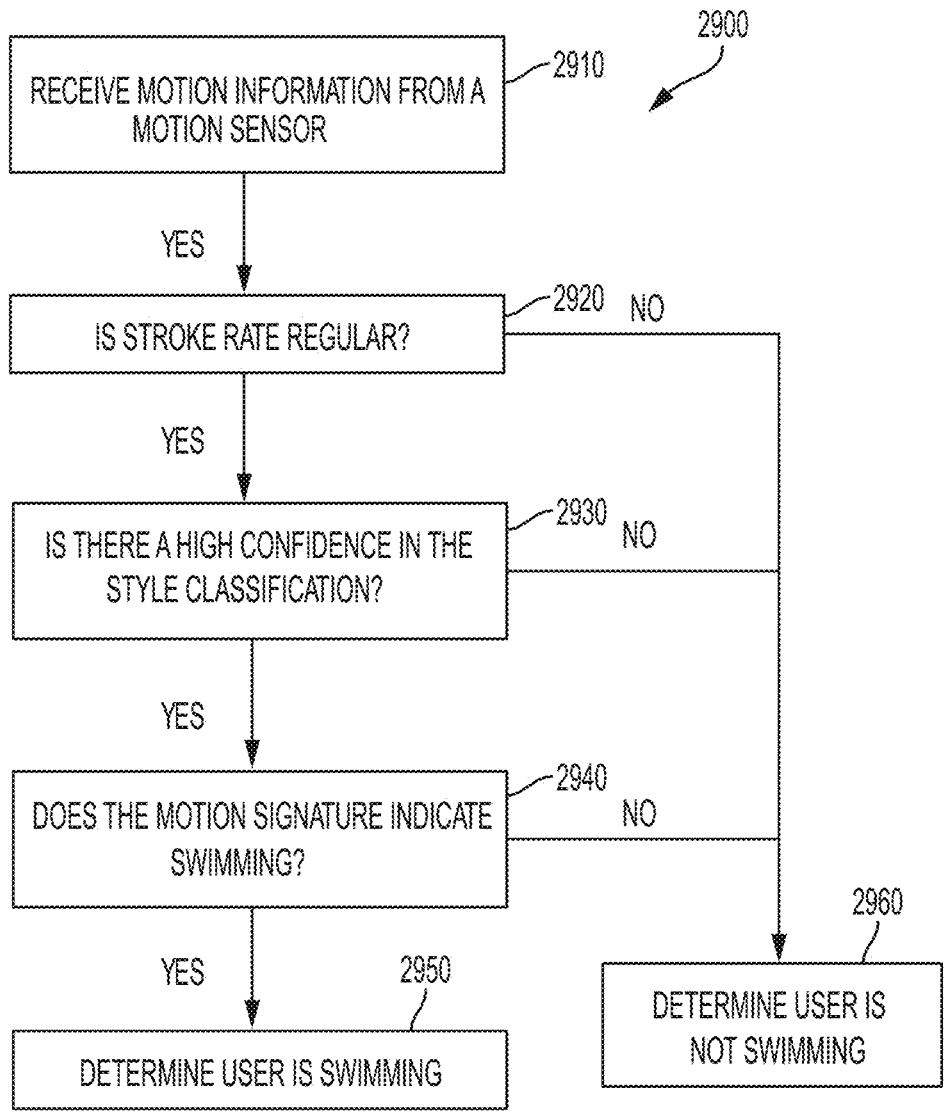
FIG. 29 is a flowchart of a method for detecting swim activity, according to some embodiments of the present disclosure.

FIG. 29 is a flowchart of a method for detecting swim activity, according to embodiments of the present disclosure. In some embodiments, method 2900 includes the step of receive motion information from a motion sensor 2910. Based on that information the method makes the following determinations: is the stroke rate regular 2920, is there a high confidence in the style classification 2930, does the motion signature indicate swimming 2940. If the answer to all of these determinations is yes, then it is determined that the user is swimming 2950. If the answer to any of these questions is no, then it is determined that the user is not swimming 2960.

For example, stroke rate can be used to detect swimming. While a user is swimming, the user will generally have a regular, periodic stroke rate/count. For example, the stroke period (e.g., the time between strokes) will have a low variance when averaged over a reasonable time window, for example, ten seconds. Conversely, when the user is not swimming, but is instead taking a break, the stroke period will be sporadic. Accordingly, the motion sensors detecting a consistent stroke period over a period of time would indicate swimming. In some embodiments, the default stroke rate for detecting swimming can be eight strokes per minute or above, corresponding to a beginner/very unskilled swimmer. If a user's stroke rate falls below the default stroke rate, then the stroke rate counter will not detect swimming.

In some embodiments, wearable device 100 can receive training data based on a user's observed stroke rate when the user wears wearable device 100. The default stroke rate to detect swimming can then be personalized to be calculated based on the user's observed stroke rate. For example, the default stroke rate can be set to the inverse of the median stroke rate of a user that was observed for at least three consecutive stroke periods.

In some embodiments, the motion sensor data also can be used for style classification, which can also provide an indication as to whether a user is swimming. Each stroke is expected to be classified as one of the common four styles: freestyle, backstroke, breaststroke, and butterfly. With popular classifiers used in pattern recognition, such as support vector machines and logistic regression, an additional notion of confidence in a classification determination can be determined. Stroke classification uses a two-tiered decision tree classifier, with logistic regression classifier at each level. In some embodiments, a range [0,1] can be assigned to each stroke classification determination, which indicates the confidence level in the classification decision, e.g., a value closer to 0 implies low confidence in the classification output, and high otherwise, as apparent in logistic regression. Alternately, confidence level can be inferred from a correlated metric such as the number of strokes with known style (i.e. not classified as Unknown) in a pre-defined time-window. Low confidence in a classification style can be a useful indicator of non-steady state swim behavior, whereas high confidence in a classification style can be a useful indicator of swimming activity. For example, low confidence can be interpreted as any value in the range [0, 0.2], while the corresponding high confidence range can be [0.2, 1.0].

Stroke rate and style classification can capture differences between steady and non-steady state swimming. However, sometimes, user arm movement while not swimming can trigger a stroke count and/or a valid style classification. For these scenarios, accelerometer energy and gyroscope signal variance can be investigated to correctly determine a motion signature that indicates swim activity.

Figure 30:
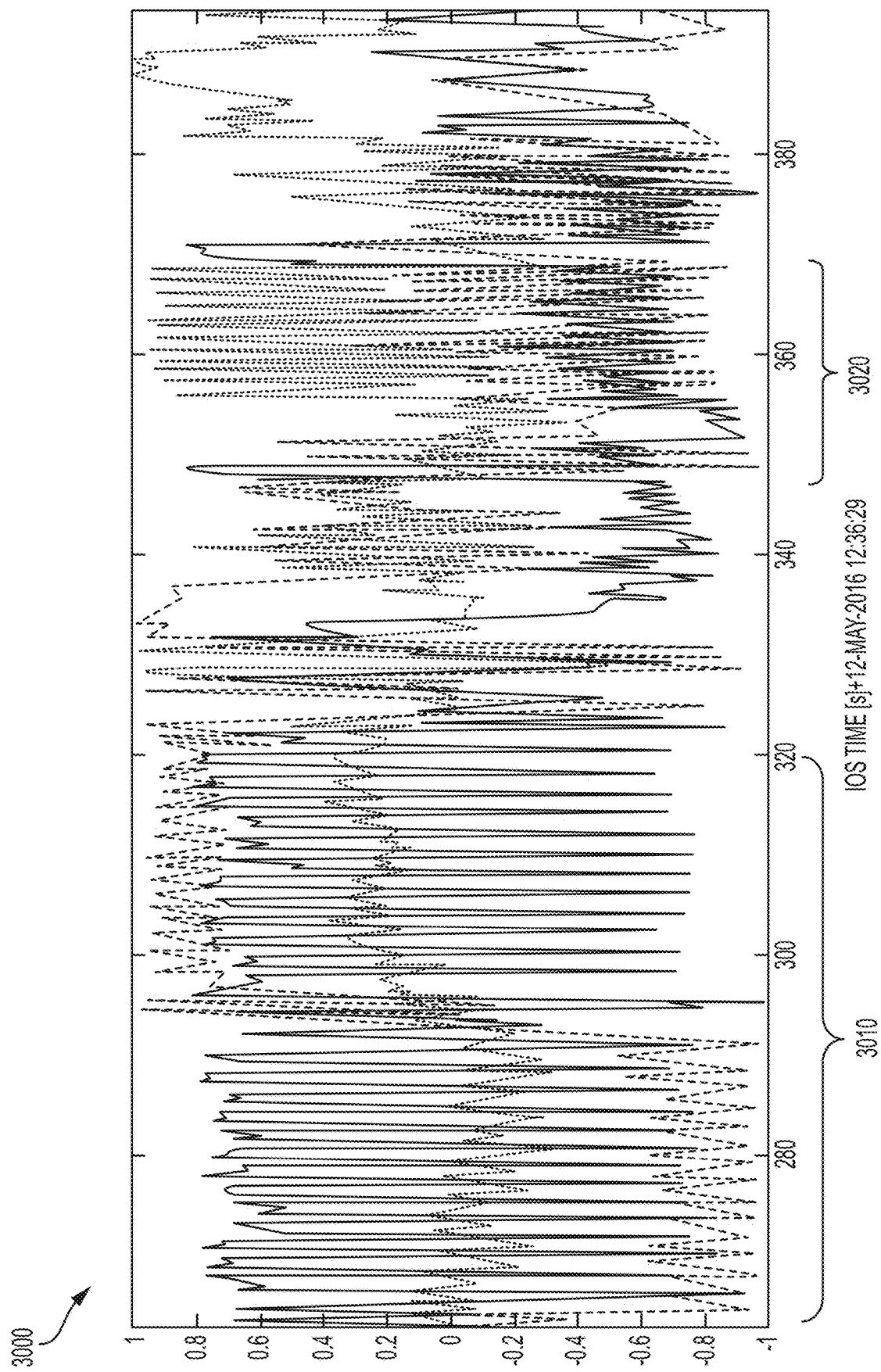
FIG. 30 is a graph illustrating exemplary discriminative information to detect swimming, according to some embodiments of the present disclosure.

Discriminative information in accelerometer and gyroscope energy (based on the accelerometer and gyroscope signals from the device sensor fusion) can be mined for swim activity detection. As discussed above, in some embodiments, the accelerometer and gyroscope signals are converted from the body fixed frame of reference to the inertial frame of reference. Referring to FIG. 30, graph 3000 depicts the crown orientation of wearable device 100. Specifically, graph 3000 includes a y axis ranging from −1 to 1, which represents upward direction towards the sky (+1) and downward direction towards the earth (−1), and an x axis, which represents time (t) from 260 seconds to 320 seconds. The graph also includes three curved lines: a bold solid line corresponding to a first inertial axis indicating crown orientation, a regular solid line corresponding to a second inertial axis perpendicular to the first inertial axis, and a dotted line corresponding to a third inertial axis perpendicular to the first and second inertial axes. Specifically, the bold solid line in graph 3000 fluctuates between −1 and 1 during t=260 to t=320 seconds (shown in the graph at 3010), indicating that the crown is pointing in various directions, as would typically occur during different stages of a user's swims strokes when he/she is swimming. In contrast, during t=350 to t=370 seconds (shown in the graph at 3020), the bold solid line is mostly negative, which indicates that the crown is pointing downwards. This consistent downward direction is typical of a user walking, not swimming.

The above considerations can be combined using a decision tree classifier with the appropriate thresholds to decide if a given epoch corresponds to swim activity or not. Decisions on successive epochs can be chained together, for example of ten seconds or more, to improve the accuracy of detection. The specific choice of threshold values is usually tied to the discriminating feature used for classification and the hierarchical order in the decision tree. A typical threshold in logistic regression is 0.5. For example, feature values greater than or equal to 0.5 represent one style, while feature values less than 0.5 represent the others. This value can be adjusted to bias the accuracy in terms of either improving true positive detection or false positive rejection.

In some embodiments, additional sensory input, for example, heart rate measurements using, for example, a PPG sensor, can be used to improve the accuracy of the swimming determination. Further, speed estimation from GPS 410 also can be used to verify the swimming determination.

The swimming determination can be used by other features of wearable device 100. For example, if wearable device 100 knows that the user is swimming, the wearable device 100 can accurately count laps, strokes, calories, and distance, as discussed in the respective applications referred to above, and incorporated by reference herein in their entirety. If the device knows that the user is not swimming, the device can disregard data from those time periods where the user is not swimming. Accordingly, the final workout data for a particular user will be more accurate, because it will reflect only those instances and periods where the user is actually swimming and will not include spurious strokes or laps where the user was not swimming, but was instead resting, or walking around the pool.

Determining Swimming Pool Length

Figure 31:
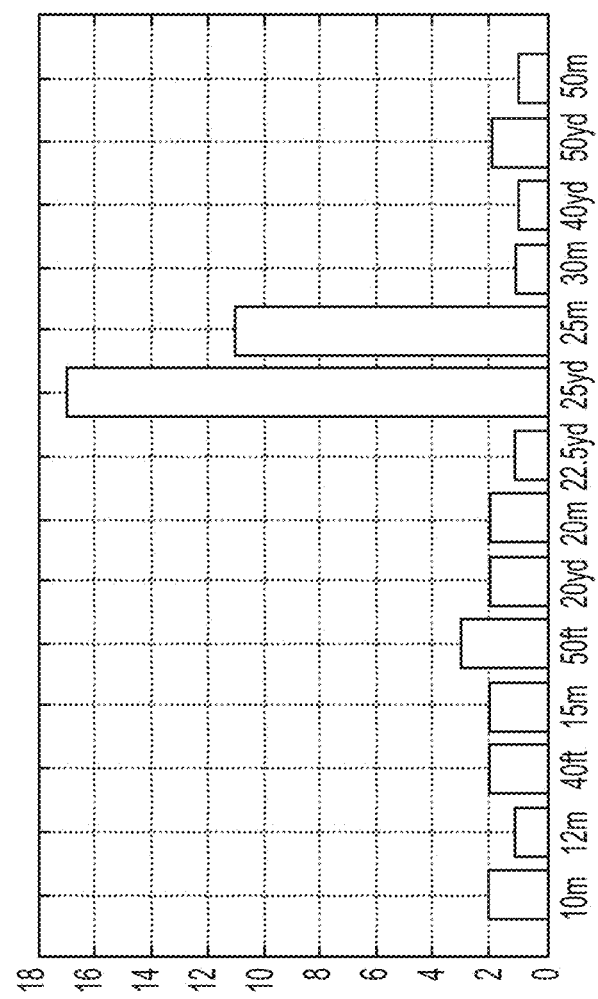
FIG. 31 illustrates an example of users' estimation of the length of a swimming pool according to some embodiments of the present disclosure.

When a user is swimming in a pool, there is often a need to know the length of the swimming pool. Information of the swimming pool length can be used to calculate the total distance a user swims and the energy expenditure associated with a swimming session. The pool length information, however, is not always readily available to users. Additionally, users may not be able to accurately estimate the pool length. FIG. 31 illustrates an example of users' estimation of a swimming pool length according to some embodiments of the present disclosure. In FIG. 31, 48 users are asked to estimate the length of a 25-yard swimming pool, and only 17 users, or 35.4% of the 48 users, have the correct estimation. FIG. 31 also shows that there is a large range between the user's responses. Two users estimate as low as 10-meter, and one user estimates as high as 50-meter.

Figure 32A:
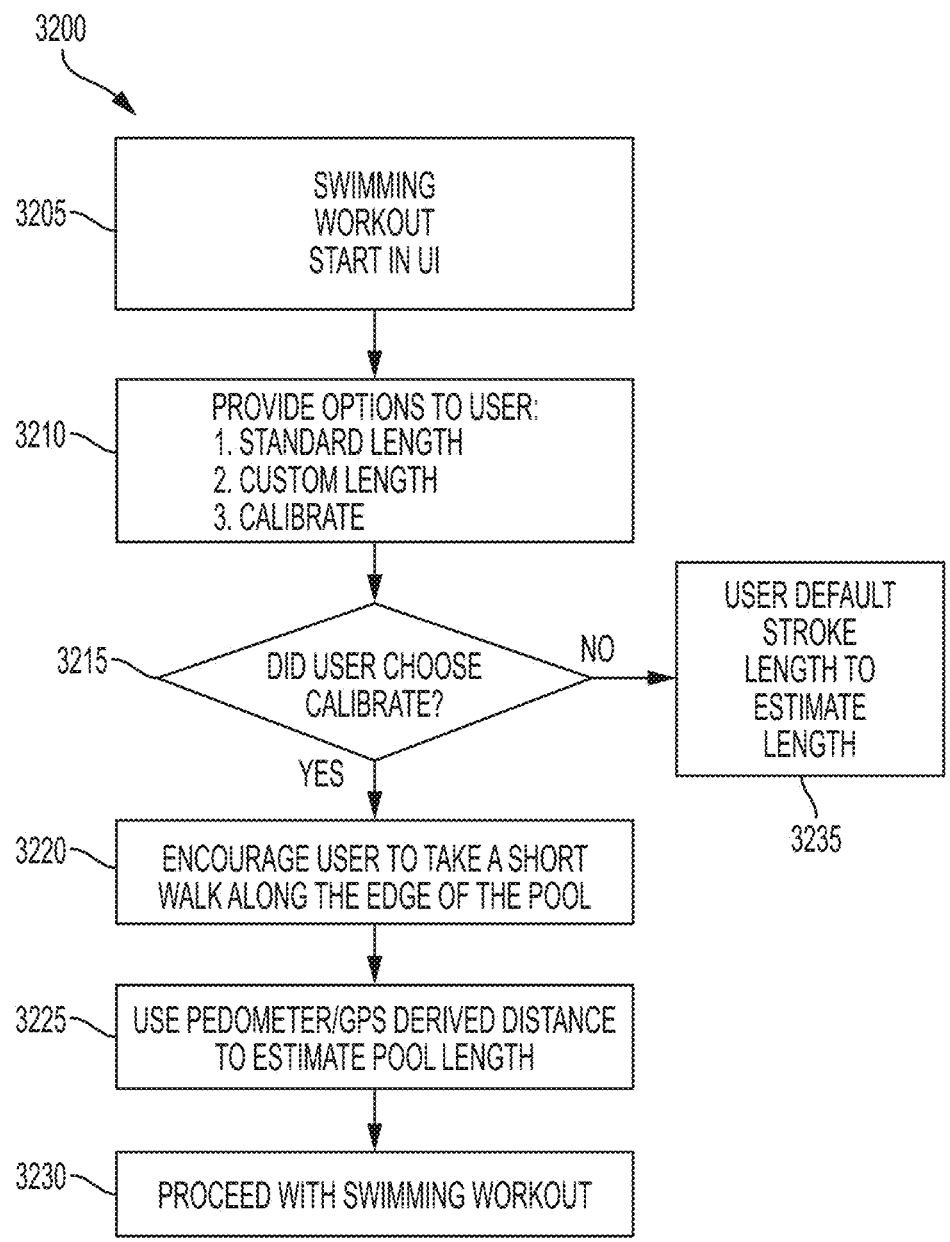
FIGS. 32A and 32B illustrate a method of determining a length of a swimming pool according to some embodiments of the present disclosure.
Figure 32B:
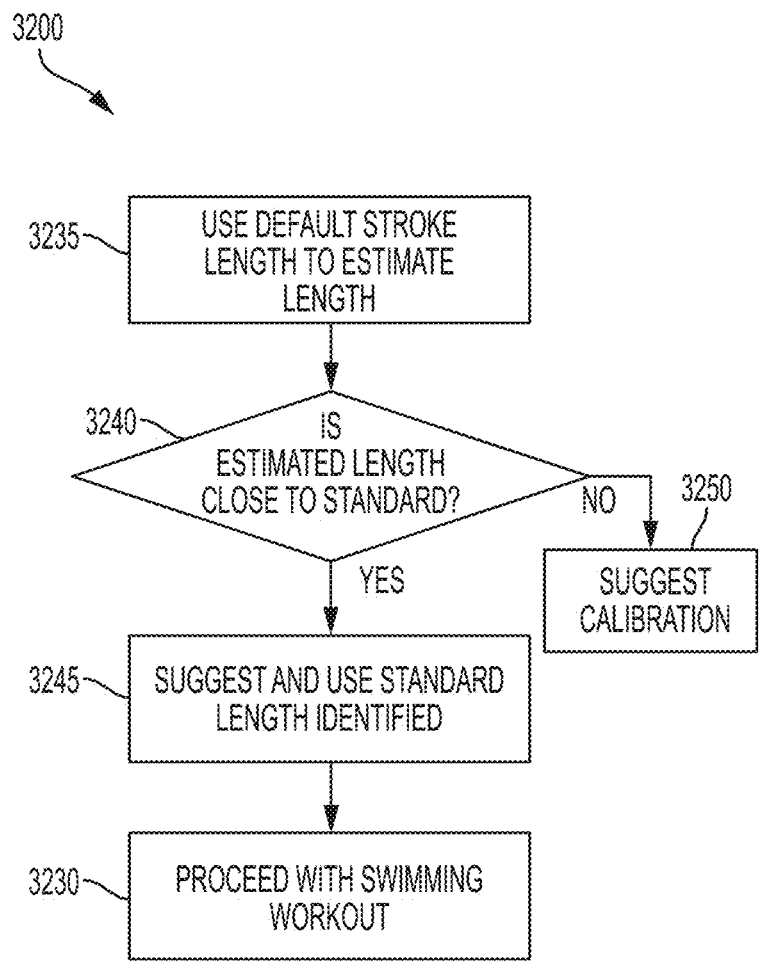

FIGS. 32A and 32B illustrate a process 3200 of determining a length of a swimming pool according to some embodiments of the present disclosure. In some embodiments, the process 3200 can be modified by, for example, having steps combined, divided, rearranged, changed, added, and/or removed.

The process 3200 starts at step 3205. At step 3205, a user can use wearable device 100 to indicate that he or she is about to start a swimming workout session at a swimming pool. The process 3200 then proceeds to step 3210.

At step 3210, wearable device 100 provides the user with one or more options to indicate the length of the swimming pool. In some embodiments, the user can choose among three options: standard length, custom length, and calibrate. In some embodiments, other suitable options can also be used. If the user chooses the standard length option, wearable device 100 can provide one or more lengths of a standard pool. Non-limiting examples of the standard length can include 25-yard, 25-meter, 33⅓-meter, or 50-meter. Other suitable standard length can also be used. In some embodiments, the user can choose to enter a standard length of the swimming pool. If the user chooses the custom length option, then the user can choose to enter a length of the swimming pool. The length can be based on information the user possesses or based on the user's estimation. If the user chooses the calibration option, then wearable device can prompt more options/instructions as described in following steps. The process 3200 then proceeds to step 3215.

At step 3215, wearable device 100 determines whether or not the user chooses the calibration option. If the user chooses the calibration option, the process 3200 proceeds to step 3220. If the user does not choose the calibration option, the process 3200 proceeds to step 3235.

At step 3220, wearable device 100 encourages the user to take a short walk along the edge of the pool, where the edge of the pool is parallel with the swimming direction of the pool. In some embodiments, the user can choose to run, jump, or any other suitable activity along the edge of the pool. The process 3200 then proceeds to step 3225.

At step 3225, wearable device 100 can use pedometer 265 and GPS sensor 295 to estimate the length associated with the user's activity at step 3220, and further estimate the length of the swimming pool. In some embodiments, pedometer 265 can count number of steps the user takes. The total distance of the user's activity can be calculated by multiplying the number of steps with a step length. In some embodiments, the step length can be a default value, a value previous customized for the user, or a value determined by GPS sensor 295. In some embodiments, the total distance of the user's activity can be directly estimated by GPS sensor 295. Once the total distance of the user's activity is estimated, the length of the swimming pool can be estimated based on a ratio between the length of the swimming pool and the length associated with the user's activity. For example, if the length associated with the user's activity at step 3220 is estimated to be 10-yard, and GPS sensor 295 further estimates the length of the swimming pool is 2.5 times of the length associated with the user's activity at step 3220, then the length of the swimming pool can be estimated to be 25-yard. The process 3200 then proceeds to step 3230.

At step 3230, once a length of the swimming pool is identified, the user can proceed with the swimming workout session.

If the user does not choose to calibrate the length of the swimming pool, the user can start to swim, and wearable device 100 can still passively estimate the length of the swimming pool. At step 3235, wearable device 100 can use default stroke length to estimate the length of the swimming pool. When the user is swimming, wearable device 100 can count the number of strokes the user has had within a short period. In some embodiments, wearable device 100 can only detect the strokes made by the arm wearing the wearable device 100. In these embodiments, for every stroke detected, the user may make two strokes, and the stroke length can sometimes be adjusted accordingly. The total distance of the user's swimming activity within a short period can be calculated by multiplying the number of strokes with a stroke length. In some embodiments, the stroke length can be a default value, a value previous customized for the user, or a value determined by GPS sensor 295. Once the total distance of the user's swimming activity within the short period is estimated, the length of the swimming pool can be estimated based on a ratio between the length of the swimming pool and the length associated with the user's swimming activity within the short period. For example, if the length associated with the user's swimming activity with the short period is estimated to be 10-yard, and GPS sensor 295 further estimates the length of the swimming pool is 2.5 times of the length associated with the user's swimming activity within the short period, then the length of the swimming pool can be estimated to be 25-yard. The process 3200 then proceeds to step 3240.

At step 3240, wearable device 100 determines whether or not the length estimated at step 3235 is close to a standard length of a swimming pool. In some embodiments, wearable device 100 can determine that an estimated length is close to a standard length if the difference is within 10% of the standard length. In some embodiments, other suitable threshold can be used. For example, if the pool length estimated at step 3240 is 20-yard, and the standard pool length is 25-yard, then wearable device 100 can determine whether or not the estimated length is close to the standard length based on the threshold. If the threshold is selected to be within 10% of the standard length, then an estimated length between 22.5-yard and 27.5-yard would be considered to be close enough, and the estimated 20-yard length would not be considered to be close enough. If the threshold is selected to be within 20% of the standard length, then an estimated length between 20-yard and 30-yard would be considered to be close enough, and the estimated 20-yard estimation would be considered to be close enough. If the estimated length is close to the standard length, the process 3200 proceeds to step 3245. If the estimated length is not close to the standard length, the process 3200 proceeds to step 3250.

At step 3245, wearable device 100 suggests that the user uses the standard length identified to be close to the length of the swimming pool. For example, if the estimated length is 24.3-yard, then wearable device 100 may suggest that the pool length is actually 25-yard, which is a length of a standard pool. The process 3200 then proceeds to step 3230.

At step 3250, because the estimated length of the swimming pool is not close to a standard swimming pool, wearable device 100 suggests that the user uses calibration to get an estimation of the length of the swimming pool. If the user chooses to calibrate, then the process 3200 proceeds to step 3220 to start the calibration process.

Figure 33:
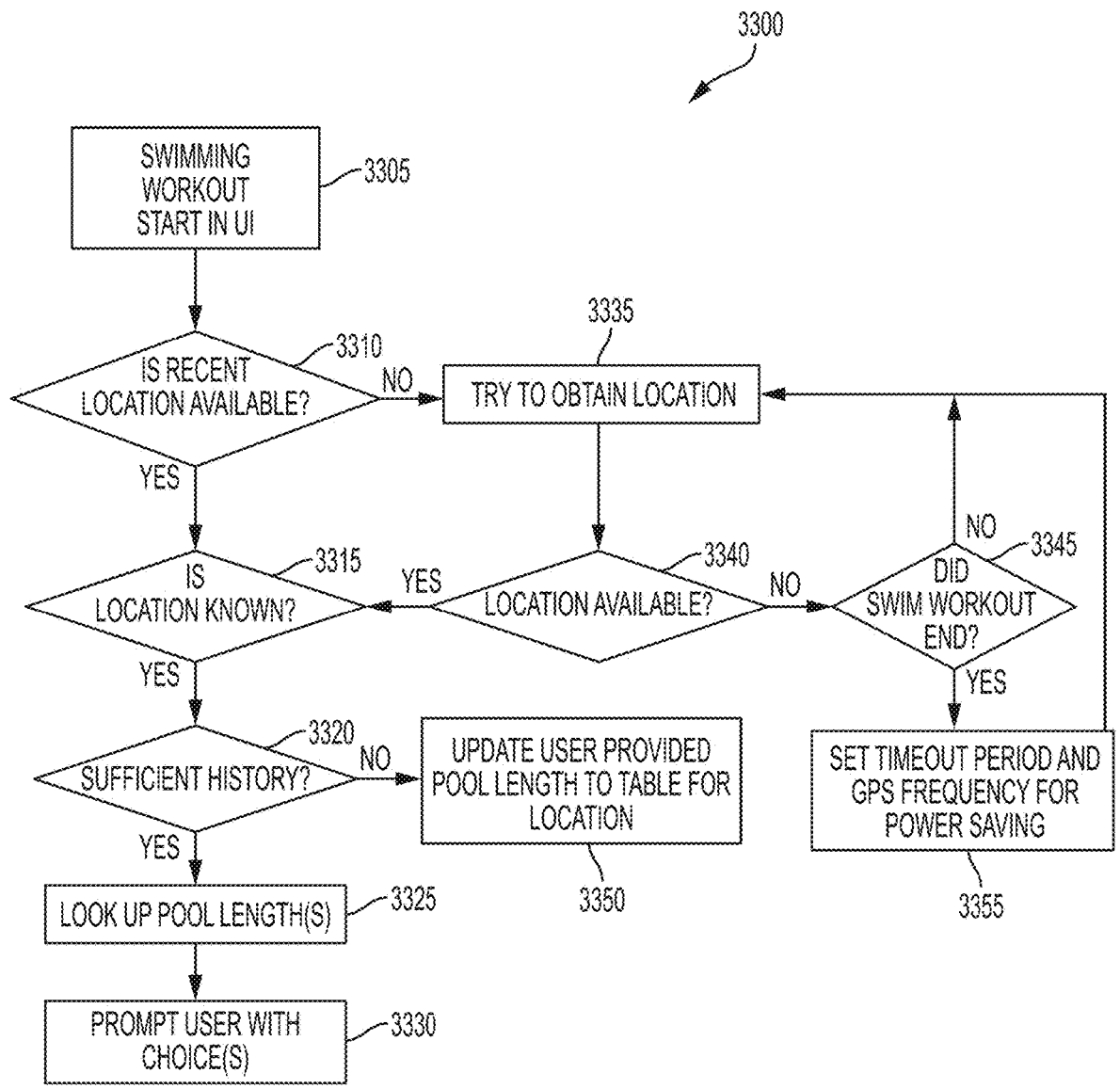
FIG. 33 illustrates a method of determining a length of a swimming pool according to some embodiments of the present disclosure.

FIG. 33 illustrates a process 3300 of determining a length of a swimming pool according to some embodiments of the present disclosure. In some embodiments, the process 3300 can be modified by, for example, having steps combined, divided, rearranged, changed, added, and/or removed.

The process 3300 starts at step 3305. At step 3305, a user can use wearable device 100 to indicate that he or she is about to start a swimming workout session at a swimming pool. The process 3300 then proceeds to step 3310.

At step 3310, wearable device 100 determines whether or not there is recent location information related to the swimming pool. In some embodiments, the location information includes a length of the swimming pool identified by other users. In some embodiments, wearable device 100 searches for the recent location information from storage media local at wearable device 100. In some embodiments, wearable device 100 searches for the recent location information from a remote storage media. If there is recent location information available, the process 3300 proceeds to step 3315. If there is no recent location information available, the process 3300 proceeds to step 3335.

At step 3315, wearable device 100 determines if the location of the swimming pool is known. If the location is known, the process 3300 proceeds to step 3320.

At step 3320, wearable device 100 determines whether or not there is sufficient history of the identified location of the swimming pool. In some embodiments, history can be pool lengths identified by other users. The threshold to determine the sufficiency of the history can be any suitable number. For example, if the threshold is set at 5, then if the length of the swimming pool has been identified by 5 or more users, then there would be sufficient history of the identified location of the swimming pool; if the length of the swimming pool has been identified by less than 5 users, then there would not be sufficient history of the identified location of the swimming pool. If there is sufficient history of the identified location of the swimming pool, the process 3300 proceeds to step 3325. If there is no sufficient history of the identified location of the swimming pool, the process 3300 proceeds to step 3350.

At step 3350, wearable device 100 prompts the user to provide an estimation of the swimming pool, and the user's estimation will be added to the pool length table.

At step 3325, since there is sufficient history of the identified location of the swimming pool, wearable device 100 looks up previously identified pool lengths associated with the swimming pool. The process 3300 then proceeds to step 3330.

At step 3330, wearable device 100 prompts the user with one or more choices of the length of the swimming pool. For example, if the swimming pool has been identified by 10 users as 25-yard and 3 users as 50-yard, then wearable device 100 can provide both choices to the user. In some embodiments, wearable device 100 can provide the length option identified by most users. In some embodiments, for each length option, wearable device 100 can also provide number of users identified such a length.

At step 3335, wearable device 100 attempts to obtain location information of the swimming pool. In some embodiments, wearable device 100 obtains location information through GPS sensor 295.

At step 3340, wearable device 100 determines whether or not location information of the swimming pool is available. If the information is available, the process 3300 proceeds to step 3315. If the information is not available, the process 3300 proceeds to step 3345.

At step 3345, wearable device 100 determines whether or not the user's swimming workout session has ended. If the user's swimming session has ended, the process 3300 proceeds to step 3355. If the user's swimming session has not ended, the process 3300 proceeds to step 3335 to continue to obtain location information.

At step 3355, since the user has already ended the swimming workout, wearable device 100 can adjust the timeout period and/or GPS frequency to save power.

Although the present disclosure has been described and illustrated in the foregoing exemplary embodiments, it is understood that the present disclosure has been made only by way of example, and that numerous changes in the details of implementation of the present disclosure may be made without departing from the spirit and scope of the present disclosure, which is limited only by the claims which follow.

What is claimed is:

1. A method for improving an accuracy of a wearable device while determining swimming metrics of a user during a swimming session, the method comprising:
   receiving, by a processor circuit of the wearable device, motion data from one or more motion sensors of the wearable device;
   determining, by the processor circuit using the motion data, a first set of rotational data of the wearable device, wherein the first set of rotational data is expressed in a first frame of reference;
   converting, by the processor circuit, the first set of rotational data into a second set of rotational data, wherein the second set of rotational data is expressed in a second frame of reference;
   determining, by the processor circuit, one or more swimming metrics of the user based on the second set of rotational data, where determining the one or more swimming metrics includes:
      detecting a number of turns and a number of strokes of the user during the swimming session based on the received motion data;
      determining a number of strokes per lap based on the number of turns and the number of strokes;
      determining a variance of the number of strokes per lap;
      adjusting the number of turns to reduce the variance of the number of strokes per lap;
      determining a lap count of the user based on the adjusted number of turns; and
   outputting, by the processor circuit, the one or more swimming metrics of the user.

2. The method of claim 1, wherein detecting a number of turns further comprises:
   determining whether a turn is not detected; and
   inserting a missing turn in the number of turns in response to a determination that a turn is not detected.

3. The method of claim 2, wherein determining whether a turn is not detected comprises:
   determining a stroke range per lap; and
   comparing the number of strokes between two consecutive turns with the determined stroke range per lap.

4. The method of claim 2, wherein determining whether a turn is not detected comprises:
   comparing the number of strokes between two consecutive turns with a threshold, wherein the threshold is determined by multiplying a mean value of the number of strokes per lap with a ratio.

5. The method of claim 1, further comprising:
   determining whether the number of strokes made by the user converges in the swimming session; or
   determining whether the number of strokes made by the user converges in a historical swimming session.

6. The method of claim 5, wherein determining whether the number of strokes made by the user converges in the swimming session comprises:
   determining a standard deviation of the number of strokes among consecutive turns; and
   comparing the standard deviation with a threshold.

7. The method of claim 6, wherein the threshold is 1.5 strokes.

8. The method of claim 1, wherein the first frame of reference comprises a body-fixed frame of reference with respect to the wearable device.

9. The method of claim 1, wherein the second frame of reference comprises an inertial frame of reference.

10. A method comprising:
   receiving, by a processor circuit of a wearable device worn on a wrist of a user during a swimming session, motion data from one or more motion sensors of the wearable device;
   determining, by the processor circuit using the motion data, a first set of rotational data of the wearable device, wherein the first set of rotational data is expressed in a first frame of reference;
   converting, by the processor circuit, the first set of rotational data into a second set of rotational data, wherein the second set of rotational data is expressed in a second frame of reference, and wherein the second set of rotational data includes data indicative of the user's arm or wrist movements;
   determining, by the processor circuit, one or more swimming metrics of the user based on the second set of rotational data, where determining the one or more swimming metrics includes:
      detecting a number of turns and a number of strokes of the user during the swimming session based on the received motion data;
      determining a number of strokes per lap based on the number of turns and the number of strokes;
      determining a variance of the number of strokes per lap;
      adjusting the number of turns to reduce the variance of the number of strokes per lap;
      determining a lap count of the user based on the adjusted number of turns; and outputting, by the processor circuit, the one or more swimming metrics of the user.

11. The method of claim 10, further comprising:
determining whether the number of strokes of the user converges in the swimming session; or
determining whether the number of strokes made by the user converges in a historical swimming session.

12. The method of claim 11, wherein determining whether the number of strokes of the user converges in the swimming session comprises:
determining a standard deviation of the number of strokes among consecutive turns; and
comparing the standard deviation with a threshold.

13. The method of claim 12, wherein the threshold is 1.5 strokes.

14. The method of claim 11, wherein determining whether a turn is not detected comprises:
determining a stroke range per lap; and
comparing the number of strokes between two consecutive turns with the determined stroke range per lap.

15. The method of claim 11, wherein determining whether a turn is not detected comprises:
comparing the number of strokes between two consecutive turns with a threshold, wherein the threshold is determined by multiplying a mean value of the number of strokes per lap with a ratio.

16. The method of claim 10, wherein the first frame of reference comprises a body-fixed frame of reference with respect to the wearable device.

17. The method of claim 10, wherein the second frame of reference comprises an inertial frame of reference.

18. The method of claim 10, wherein detecting a number of turns further comprises:
determining whether a turn is not detected; and
inserting a missing turn in the number of turns in response to a determination that a turn is not detected.

19. A system for improving an accuracy of a wearable device while determining one or more swimming metrics of a user during a swimming session, the system comprising:
one or more motion sensors configured to collect motion data; and
a processor circuit coupled to the one or more motion sensors and configured to execute instructions causing the processor to:
determine a first set of rotational data, wherein the first set of rotational data is expressed in a first frame of reference;
convert the first set of rotational data into a second set of rotational data, wherein the second set of rotational data is expressed in a second frame of reference;
determine one or more swimming metrics of the user based on the second set of rotational data, where determining the one or more swimming metrics includes:
detecting a number of turns and a number of strokes of the user during the swimming session based on the received motion data;
determine a number of strokes per lap based on the number of turns and the number of strokes;
determine a variance of the number of strokes per lap;
adjust the number of turns to reduce the variance of the number of strokes per lap;
determine a lap count of the user based on the adjusted number of turns; and
output the one or more swimming metrics of the user.

20. A system comprising:
one or more motion sensors configured to collect motion data, the one or more sensors included in or coupled to a wearable device worn on a wrist of a user during a swimming session;
a processor circuit coupled to the one or more motion sensors and configured to execute instructions causing the processor to:
receive motion data from one or more motion sensors of the wearable device;
determine, using the motion data, a first set of rotational data of the wearable device, wherein the first set of rotational data is expressed in a first frame of reference;
convert the first set of rotational data into a second set of rotational data, wherein the second set of rotational data is expressed in a second frame of reference, and wherein the second set of rotational data includes data indicative of the user's arm or wrist movements;
determine one or more swimming metrics of the user based on the second set of rotational data, where the instructed are further executed to:
detect a number of turns and a number of strokes of the user during the swimming session based on the received motion data;
determine a number of strokes per lap based on the number of turns and the number of strokes;
determine a variance of the number of strokes per lap;
adjust the number of turns to reduce the variance of the number of strokes per lap;
determine a lap count of the user based on the adjusted number of turns; and
output the one or more swimming metrics of the user.

* * * * *